(12) United States Patent
Kishawi et al.

(10) Patent No.: US 9,409,021 B2
(45) Date of Patent: Aug. 9, 2016

(54) SELECTIVE STIMULATION SYSTEMS AND SIGNAL PARAMETERS FOR MEDICAL CONDITIONS

(71) Applicant: Eyad Kishawi, San Carlos, CA (US)

(72) Inventors: Eyad Kishawi, San Carlos, CA (US);
Mir A. Imran, Los Altos, CA (US);
Brian J. Mossop, San Francisco, CA (US); Jeffery M. Kramer, San Francisco, CA (US); Richard W. O'Connor, Redwood City, CA (US)

(73) Assignee: St. Jude Medical Luxembourg Holdings SMI S.A.R.L., Luxembourg (LU)

( * ) Notice: Subject to any disclaimer, the term of this patent is extended or adjusted under 35 U.S.C. 154(b) by 0 days.

(21) Appl. No.: 14/726,359

(22) Filed: May 29, 2015

(65) Prior Publication Data
US 2015/0258338 A1    Sep. 17, 2015

Related U.S. Application Data

(62) Division of application No. 12/607,009, filed on Oct. 27, 2009, now Pat. No. 9,056,197.

(60) Provisional application No. 61/108,836, filed on Oct. 27, 2008.

(51) Int. Cl.
*A61N 1/36* (2006.01)
*A61N 1/05* (2006.01)
*A61N 1/372* (2006.01)

(52) U.S. Cl.
CPC .......... *A61N 1/36071* (2013.01); *A61N 1/0551* (2013.01); *A61N 1/36157* (2013.01); *A61N 1/37247* (2013.01)

(58) Field of Classification Search
None
See application file for complete search history.

(56) References Cited

U.S. PATENT DOCUMENTS

| 525,891 | A | 9/1894 | Fricke |
| 3,724,467 | A | 4/1973 | Avery et al. |
| 3,845,770 | A | 11/1974 | Theeuwes et al. |
| 3,916,899 | A | 11/1975 | Theeuwes et al. |
| 4,141,367 | A | 2/1979 | Ferreira |

(Continued)

FOREIGN PATENT DOCUMENTS

| CN | 2401143 Y | 10/2000 |
| CN | 101594907 A | 12/2009 |

(Continued)

OTHER PUBLICATIONS

Kishawi et al.; U.S. Appl. No. 13/753,326 entitled "Pain management with stimulation subthreshold to parasthesia," filed Jan. 29, 2013.

(Continued)

*Primary Examiner* — Brian T Gedeon

(57) ABSTRACT

Devices, systems and methods are provided for targeted treatment of a variety of conditions, particularly conditions that are associated with or influenced by the nervous system, such as pain. Targeted treatment of such conditions is provided with minimal deleterious side effects, such as undesired motor responses or undesired stimulation of unaffected body regions. This is achieved by directly neuromodulating a target anatomy associated with the condition while minimizing or excluding undesired neuromodulation of other anatomies.

9 Claims, 26 Drawing Sheets

(56) References Cited

U.S. PATENT DOCUMENTS

| | | |
|---|---|---|
| 4,232,679 A | 11/1980 | Schulman |
| 4,298,003 A | 11/1981 | Theeuwes et al. |
| 4,313,448 A | 2/1982 | Stokes |
| 4,374,527 A | 2/1983 | Iversen |
| 4,479,491 A | 10/1984 | Martin |
| 4,549,556 A | 10/1985 | Tarjan et al. |
| 4,573,481 A | 3/1986 | Bullara |
| 4,577,642 A | 3/1986 | Stokes |
| 4,590,946 A | 5/1986 | Loeb |
| 4,607,639 A | 8/1986 | Tanagho et al. |
| 4,739,764 A | 4/1988 | Lue et al. |
| 4,786,155 A | 11/1988 | Fantone et al. |
| 4,803,988 A | 2/1989 | Thomson |
| 4,920,979 A | 5/1990 | Bullara |
| 4,940,065 A | 7/1990 | Tanagho et al. |
| 4,950,270 A | 8/1990 | Bowman et al. |
| 4,976,711 A | 12/1990 | Parins et al. |
| 5,135,525 A | 8/1992 | Biscoping et al. |
| 5,270,099 A | 12/1993 | Kamiyama et al. |
| 5,299,569 A | 4/1994 | Wernicke et al. |
| 5,330,515 A * | 7/1994 | Rutecki .............. A61N 1/36071 607/46 |
| 5,344,438 A | 9/1994 | Testerman et al. |
| 5,358,514 A | 10/1994 | Schulman et al. |
| 5,370,644 A | 12/1994 | Langberg |
| 5,411,537 A | 5/1995 | Munshi et al. |
| 5,411,540 A | 5/1995 | Edell et al. |
| 5,417,719 A | 5/1995 | Hull et al. |
| 5,419,763 A | 5/1995 | Hildebrand |
| 5,458,626 A | 10/1995 | Krause |
| 5,489,294 A | 2/1996 | McVenes et al. |
| 5,505,201 A | 4/1996 | Grill et al. |
| 5,514,175 A | 5/1996 | Kim et al. |
| 5,584,835 A | 12/1996 | Greenfield |
| 5,634,462 A | 6/1997 | Tyler et al. |
| 5,643,330 A | 7/1997 | Holsheimer et al. |
| 5,702,429 A | 12/1997 | King |
| 5,711,316 A | 1/1998 | Elsberry et al. |
| 5,713,922 A | 2/1998 | King |
| 5,733,322 A | 3/1998 | Starkebaum |
| 5,741,319 A | 4/1998 | Woloszko et al. |
| 5,755,750 A | 5/1998 | Petruska et al. |
| 5,776,170 A | 7/1998 | MacDonald et al. |
| 5,807,339 A | 9/1998 | Bostrom et al. |
| 5,824,021 A | 10/1998 | Rise |
| 5,865,843 A | 2/1999 | Baudino |
| 5,871,531 A | 2/1999 | Struble |
| 5,885,290 A | 3/1999 | Guerrero et al. |
| 5,938,690 A | 8/1999 | Law et al. |
| 5,948,007 A | 9/1999 | Starkebaum et al. |
| 5,957,965 A | 9/1999 | Moumane et al. |
| 5,983,141 A | 11/1999 | Sluijter et al. |
| 5,984,896 A | 11/1999 | Boyd |
| 6,002,964 A | 12/1999 | Feler et al. |
| 6,044,297 A | 3/2000 | Sheldon et al. |
| 6,045,532 A | 4/2000 | Eggers et al. |
| 6,051,017 A | 4/2000 | Loeb et al. |
| 6,104,957 A | 8/2000 | Alo et al. |
| 6,120,467 A | 9/2000 | Schallhorn |
| 6,161,048 A | 12/2000 | Sluijter et al. |
| 6,175,764 B1 | 1/2001 | Loeb et al. |
| 6,181,965 B1 | 1/2001 | Loeb et al. |
| 6,185,455 B1 | 2/2001 | Loeb et al. |
| 6,205,359 B1 | 3/2001 | Boveja |
| 6,208,902 B1 | 3/2001 | Boveja |
| 6,214,016 B1 | 4/2001 | Williams et al. |
| 6,259,952 B1 | 7/2001 | Sluijter et al. |
| 6,298,256 B1 | 10/2001 | Meyer |
| 6,314,325 B1 | 11/2001 | Fitz |
| 6,319,241 B1 | 11/2001 | King et al. |
| 6,349,233 B1 | 2/2002 | Adams |
| 6,353,762 B1 | 3/2002 | Baudino et al. |
| 6,356,786 B1 | 3/2002 | Rezai et al. |
| 6,360,750 B1 | 3/2002 | Gerber et al. |
| 6,366,814 B1 | 4/2002 | Boveja et al. |
| 6,393,325 B1 | 5/2002 | Mann et al. |
| 6,413,255 B1 | 7/2002 | Stern |
| 6,425,887 B1 | 7/2002 | McGuckin et al. |
| 6,438,423 B1 | 8/2002 | Rezai et al. |
| 6,440,090 B1 | 8/2002 | Schallhorn |
| 6,466,821 B1 | 10/2002 | Pianca et al. |
| 6,493,588 B1 | 12/2002 | Malaney et al. |
| 6,510,347 B2 | 1/2003 | Borkan |
| 6,512,958 B1 | 1/2003 | Swoyer et al. |
| 6,516,227 B1 | 2/2003 | Meadows et al. |
| 6,517,542 B1 | 2/2003 | Papay et al. |
| 6,522,926 B1 | 2/2003 | Kieval et al. |
| 6,535,767 B1 | 3/2003 | Kronberg |
| 6,582,441 B1 | 6/2003 | He et al. |
| 6,587,725 B1 | 7/2003 | Durand et al. |
| 6,605,094 B1 | 8/2003 | Mann et al. |
| 6,606,521 B2 | 8/2003 | Paspa et al. |
| 6,611,715 B1 | 8/2003 | Boveja |
| 6,625,496 B1 | 9/2003 | Ollivier |
| 6,638,276 B2 | 10/2003 | Sharkey et al. |
| 6,658,302 B1 | 12/2003 | Kuzma et al. |
| 6,714,822 B2 | 3/2004 | King et al. |
| 6,748,276 B1 | 6/2004 | Daignault, Jr. et al. |
| 6,754,539 B1 | 6/2004 | Erickson et al. |
| 6,788,975 B1 | 9/2004 | Whitehurst et al. |
| 6,792,318 B2 | 9/2004 | Chitre et al. |
| 6,832,115 B2 | 12/2004 | Borkan |
| 6,835,194 B2 | 12/2004 | Johnson et al. |
| 6,839,588 B1 | 1/2005 | Rudy |
| 6,849,075 B2 | 2/2005 | Bertolero et al. |
| 6,862,479 B1 | 3/2005 | Whitehurst et al. |
| 6,871,099 B1 | 3/2005 | Whitehurst et al. |
| 6,873,342 B2 | 3/2005 | Perry et al. |
| 6,889,094 B1 | 5/2005 | Kuzma et al. |
| 6,901,287 B2 | 5/2005 | Davis et al. |
| 6,902,547 B2 | 6/2005 | Aves et al. |
| 6,909,917 B2 | 6/2005 | Woods et al. |
| 6,928,320 B2 | 8/2005 | King |
| 6,971,391 B1 | 12/2005 | Wang et al. |
| 6,978,180 B2 | 12/2005 | Tadlock |
| 7,047,082 B1 | 5/2006 | Schrom et al. |
| 7,096,070 B1 | 8/2006 | Jenkins et al. |
| 7,127,287 B2 | 10/2006 | Duncan et al. |
| 7,181,289 B2 | 2/2007 | Pflueger et al. |
| 7,333,857 B2 | 2/2008 | Campbell |
| 7,337,005 B2 | 2/2008 | Kim et al. |
| 7,337,006 B2 | 2/2008 | Kim et al. |
| 7,447,546 B2 | 11/2008 | Kim et al. |
| 7,450,993 B2 | 11/2008 | Kim et al. |
| 7,502,651 B2 | 3/2009 | Kim et al. |
| 7,580,753 B2 | 8/2009 | Kim et al. |
| 8,082,039 B2 | 12/2011 | Kim et al. |
| 8,229,565 B2 | 7/2012 | Kim et al. |
| 8,380,318 B2 | 2/2013 | Kishawi et al. |
| 8,518,092 B2 | 8/2013 | Burdulis |
| 8,712,546 B2 | 4/2014 | Kim et al. |
| 8,983,624 B2 | 3/2015 | Imran |
| 9,044,592 B2 | 6/2015 | Imran et al. |
| 9,056,197 B2 | 6/2015 | Imran et al. |
| 2001/0003799 A1 | 6/2001 | Boveja |
| 2001/0006967 A1 | 7/2001 | Crain et al. |
| 2002/0064841 A1 | 5/2002 | Klemic et al. |
| 2002/0077684 A1 | 6/2002 | Clemens et al. |
| 2002/0087113 A1 | 7/2002 | Hartlaub |
| 2002/0099430 A1 | 7/2002 | Verness |
| 2002/0116030 A1 | 8/2002 | Rezai |
| 2002/0128694 A1 | 9/2002 | Holsheimer |
| 2002/0147486 A1 | 10/2002 | Soukup et al. |
| 2002/0198527 A1 | 12/2002 | Muckter |
| 2003/0018367 A1 | 1/2003 | Dilorenzo |
| 2003/0023241 A1 | 1/2003 | Drewry et al. |
| 2003/0045919 A1 | 3/2003 | Swoyer et al. |
| 2003/0069569 A1 | 4/2003 | Burdette et al. |
| 2003/0078633 A1 | 4/2003 | Firlik et al. |
| 2003/0088301 A1 | 5/2003 | King |
| 2003/0100933 A1 | 5/2003 | Ayal et al. |
| 2003/0114905 A1 | 6/2003 | Kuzma |
| 2003/0130577 A1 | 7/2003 | Purdy et al. |
| 2003/0144657 A1 | 7/2003 | Bowe et al. |

(56) References Cited

U.S. PATENT DOCUMENTS

| | | |
|---|---|---|
| 2003/0144709 A1 | 7/2003 | Zabara et al. |
| 2003/0181958 A1 | 9/2003 | Dobak, III |
| 2003/0187490 A1 | 10/2003 | Gliner |
| 2003/0195602 A1 | 10/2003 | Boling |
| 2003/0220677 A1 | 11/2003 | Doan et al. |
| 2004/0015202 A1 | 1/2004 | Chandler et al. |
| 2004/0019359 A1 | 1/2004 | Worley et al. |
| 2004/0019369 A1 | 1/2004 | Duncan et al. |
| 2004/0059404 A1 | 3/2004 | Bjorklund et al. |
| 2004/0116977 A1 | 6/2004 | Finch et al. |
| 2004/0122360 A1 | 6/2004 | Waldhauser et al. |
| 2004/0122477 A1 | 6/2004 | Whitehurst et al. |
| 2004/0122497 A1 | 6/2004 | Zhang et al. |
| 2004/0122498 A1 | 6/2004 | Zhang et al. |
| 2004/0147992 A1 | 7/2004 | Bluger et al. |
| 2004/0210290 A1 | 10/2004 | Omar-Pasha |
| 2004/0215286 A1 | 10/2004 | Stypulkowski |
| 2004/0230273 A1 | 11/2004 | Cates et al. |
| 2004/0230280 A1 | 11/2004 | Cates et al. |
| 2004/0243210 A1 | 12/2004 | Morgan et al. |
| 2005/0027338 A1 | 2/2005 | Hill |
| 2005/0033295 A1 | 2/2005 | Wisnewski |
| 2005/0033393 A1 | 2/2005 | Daglow |
| 2005/0038489 A1 | 2/2005 | Grill |
| 2005/0070982 A1 | 3/2005 | Heruth et al. |
| 2005/0080325 A1 | 4/2005 | Erickson |
| 2005/0090885 A1 | 4/2005 | Harris et al. |
| 2005/0096718 A1 | 5/2005 | Gerber et al. |
| 2005/0149154 A1 | 7/2005 | Cohen et al. |
| 2005/0154437 A1 | 7/2005 | Williams |
| 2005/0159799 A1 | 7/2005 | Daglow et al. |
| 2005/0203599 A1 | 9/2005 | Garabedian et al. |
| 2005/0222647 A1 | 10/2005 | Wahlstrand et al. |
| 2005/0251237 A1 | 11/2005 | Kuzma et al. |
| 2006/0004364 A1 | 1/2006 | Green et al. |
| 2006/0009820 A1 | 1/2006 | Royle |
| 2006/0041295 A1 | 2/2006 | Osypka |
| 2006/0052836 A1 | 3/2006 | Kim et al. |
| 2006/0052856 A1 | 3/2006 | Kim et al. |
| 2006/0064150 A1 | 3/2006 | Heist et al. |
| 2006/0089609 A1 | 4/2006 | Bleich et al. |
| 2006/0089696 A1 | 4/2006 | Olsen et al. |
| 2006/0094976 A1 | 5/2006 | Bleich |
| 2006/0095088 A1 | 5/2006 | DeRidder |
| 2006/0155344 A1 | 7/2006 | Rezai et al. |
| 2006/0161235 A1 | 7/2006 | King |
| 2006/0167525 A1 | 7/2006 | King |
| 2006/0195169 A1 | 8/2006 | Gross et al. |
| 2006/0200121 A1 | 9/2006 | Mowery |
| 2006/0206118 A1 | 9/2006 | Kim et al. |
| 2006/0241716 A1 | 10/2006 | Finch et al. |
| 2006/0247750 A1 | 11/2006 | Seifert et al. |
| 2007/0043400 A1 | 2/2007 | Donders et al. |
| 2007/0060954 A1 | 3/2007 | Cameron et al. |
| 2007/0123954 A1 | 5/2007 | Gielen et al. |
| 2007/0179579 A1 | 8/2007 | Feler et al. |
| 2007/0213671 A1 | 9/2007 | Hiatt |
| 2007/0255366 A1 | 11/2007 | Gerber et al. |
| 2007/0270928 A1 | 11/2007 | Erlebacher |
| 2007/0276319 A1 | 11/2007 | Betts |
| 2008/0009927 A1 | 1/2008 | Vilims |
| 2008/0033431 A1 | 2/2008 | Jung et al. |
| 2008/0039916 A1 | 2/2008 | Colliou et al. |
| 2008/0103572 A1 | 5/2008 | Gerber |
| 2008/0103579 A1 | 5/2008 | Gerber |
| 2008/0103580 A1 | 5/2008 | Gerber |
| 2008/0119711 A1 | 5/2008 | Nikumb et al. |
| 2008/0140152 A1 | 6/2008 | Imran et al. |
| 2008/0140153 A1 | 6/2008 | Burdulis |
| 2008/0147156 A1 | 6/2008 | Imran |
| 2008/0154349 A1 | 6/2008 | Rossing et al. |
| 2008/0183221 A1 | 7/2008 | Burdulis |
| 2008/0188916 A1 | 8/2008 | Jones et al. |
| 2009/0204173 A1 | 8/2009 | Fang et al. |
| 2009/0248095 A1 | 10/2009 | Schleicher et al. |
| 2009/0270960 A1 | 10/2009 | Zhao et al. |
| 2009/0299444 A1 | 12/2009 | Boling |
| 2010/0121408 A1 | 5/2010 | Imran et al. |
| 2010/0179562 A1 | 7/2010 | Linker et al. |
| 2010/0191307 A1 | 7/2010 | Fang et al. |
| 2010/0292769 A1 | 11/2010 | Brounstein et al. |
| 2011/0184486 A1 | 7/2011 | De Ridder |
| 2011/0276056 A1 | 11/2011 | Grigsby et al. |
| 2012/0158094 A1 | 6/2012 | Kramer et al. |
| 2012/0197370 A1 | 8/2012 | Kim et al. |
| 2012/0277839 A1 | 11/2012 | Kramer et al. |
| 2012/0283697 A1 | 11/2012 | Kim et al. |
| 2012/0310140 A1 | 12/2012 | Kramer et al. |
| 2013/0165991 A1 | 6/2013 | Kim et al. |
| 2013/0345783 A1 | 12/2013 | Burdulis |
| 2014/0200625 A1 | 7/2014 | Kim et al. |
| 2014/0343624 A1 | 11/2014 | Kramer |
| 2015/0151126 A1 | 6/2015 | Kishawi et al. |
| 2015/0165193 A1 | 6/2015 | Imran |

FOREIGN PATENT DOCUMENTS

| | | |
|---|---|---|
| CN | 101678204 A | 3/2010 |
| EP | 0779080 A | 6/1997 |
| EP | 1304135 A2 | 4/2003 |
| EP | 2756864 A1 | 7/2014 |
| JP | 03041191 B2 | 6/1991 |
| JP | H06-218064 A | 8/1994 |
| JP | 8500996 A | 2/1996 |
| JP | 8080353 A | 3/1996 |
| JP | 10243954 A | 9/1998 |
| JP | 2004512105 | 4/2004 |
| JP | 2006523215 | 10/2004 |
| JP | 2005516697 | 6/2005 |
| JP | 2006508768 | 3/2006 |
| JP | 2008526299 | 7/2008 |
| JP | 2009539425 A | 11/2009 |
| JP | 2009539426 A | 11/2009 |
| WO | WO 02/096512 A1 | 12/2002 |
| WO | WO 03/018113 A1 | 3/2003 |
| WO | WO 03/043690 A1 | 5/2003 |
| WO | WO 03/063692 A2 | 8/2003 |
| WO | WO 03/066154 A2 | 8/2003 |
| WO | WO 03/084433 A2 | 10/2003 |
| WO | WO 03/090599 A2 | 11/2003 |
| WO | WO 2005/092432 A1 | 10/2005 |
| WO | WO 2006/029257 A2 | 3/2006 |
| WO | WO 2006/033039 A1 | 3/2006 |
| WO | WO 2006/084635 A2 | 8/2006 |
| WO | WO 2008/070804 A2 | 6/2008 |
| WO | WO 2008/070807 A2 | 6/2008 |
| WO | WO 2008/070809 A2 | 6/2008 |
| WO | WO 2009/134350 A2 | 11/2009 |

OTHER PUBLICATIONS

Burdulis; U.S. Appl. No. 14/633,060 entitled "Hard tissue anchors and delivery devices," filed Feb. 26, 2015.

Imran et al.; U.S. Appl. No. 14/719,076 entitled "Sutureless lead retention features," filed May 21, 2015.

Abdulla et al.; Axotomy- and autotomy-induced changes in the excitability of off rat dorsal root ganglion neurons; J Neurophysical; 85(2); pp. 630-643; Feb. 2001.

Advanced Neuromodulation Systems, Inc. (ANSI) Research Briefing dated Aug. 20, 2004 by Stephens Inc. Investment Bankers pp. 1-4.

Advanced Neuromodulation Systems, Inc. (ANSI) Research Bulletin dated Jul. 2, 2004 by Stephens Inc. Investment Bankers pp. 1-7.

Advanced Neuromodulation Systems, Inc. (ANSI) Research Bulletin dated Jul. 27, 2004 by Stephens Inc. Investment Bankers pp. 1-9.

Advanced Neuromodulation Systems, Inc. Equity Research dated Jan. 16, 2003 by Pacific Growth Equities pp. 1-8.

Alo, Kenneth M. New Trends in Neuromodulation for the Management of Neuropathic Pain. Neurosurgery. 50 (4): 690-703. Apr. 2002.

Aoki, Yasuchika et al. Distribution and Immunocytochemical Characterization of Dorsal Root Ganglion Neurons Innervating the Lumbar Intervertebral Disc in Rats: A Review. Life Sciences. 74 (21): 2627-2642. Apr. 2004.

(56) References Cited

OTHER PUBLICATIONS

Askar, Zahid, et al. Scott Wiring for Direct Repair of Lumbar Spondylolysis. Spine. . 28 (4): 354-357. Feb. 2003.
Baba, Hiroshi et al. Peripheral Inflammation Facilitates A? Fiber-Mediated Synaptic Input to the Substantia Gelatinosa of the Adult Rat Spinal Cord. The Journal of Neuroscience. 19 (2): 859-867. Jan. 1999.
Bajwa, Zahid H. et al. Herpetic Neuralgia: Use of Combination Therapy for Pain Relief in Acute and Chronic Herpes Zoster. Geriatrics. 56 (12): 18-24. Dec. 2001.
Barendse, G.A. et al. Randomized Controlled Trial of Percutaneous Intradiscal Radiofrequency Thermocoagulation for Chronic Discogenic Back Pain: Lack of Effect From a 90-Second 70 C Lesion. Spine. 26 (3): 287-92. (Abstract Only). Feb. 1, 2001.
Barlocher, C.B. et al. Kryorhizotomy: An Alternative Technique for Lumbar Medial Branch Rhizotomy in Lumbar Facet Syndrome. J Neurosurg. 98 (1): 14-20. (Abstract Only). Jan. 2003.
Blau, A. et al. Characterization and Optimization of Microelectrode Arrays for in Vivo Nerve Signal Recording and Stimulation. Biosens Bioelectron. 12 (9-10): 883-92. (Abstract Only). Nov. 1997.
Boston Scientific a Neuromodulation Primer dated Jun. 9, 2004 in Medical Supplies and Devices, published by Susquehanna Financial Group, LLLP pp. 1-17.
Brammah, T.B. et al. . Syringomyelia as a Complication of Spinal Arachnoiditis. Spine. 19 (22): 2603-5. (Abstract Only). Nov. 15, 1994.
Braverman D.L. et al. Using Gabapentin to Treat Failed Back Surgery Syndrome Caused by Epidural Fibrosis: A Report of 2 Cases. Arch Phys Med Rehabil. 82 (5): 691-3. (Abstract Only). May 2001.
Burton et al.; The organization of the seventh lumbar spinal ganglion of the cat; J Comp Neurol.; 149(2); pp. 215-232; May 15, 1973.
Carlton, Susan M. et al. Tonic Control of Peripheral Cutaneous Nociceptors by Somatostatin Receptors. Journal of Neuroscience. 21 (11): 4042-4049. Jun. 1, 2001.
Chaplan, S.R. et al. Quantitative Assessment of Tactile Allodynia in the Rat Paw. Journal of Neuroscience Methods. 53 (1): 55-63. Jul. 1994.
Cho, J. Percutaneo Radiofrequency Lumbar Facet Rhizotomy in Mechanical Low Back Pain Syndrome. Stereotact Funct Neurosurg. 68 (1-4): 212-7. (Abstract Only). (year of pub. sufficiently earlier than effective US filing date and any foreign priority date) 1997.
Cipolla—The Cerebral Circulation,Chap. 3-Perivascular Innervation ; Morgan & Claypool Life Sciences; San Rafael, Ca.; 1(1):pp. 3; Jan. 2009.
Clark, Robert K. "Anatomy and physiology: understanding the human body"; Jones & Bartlett Publishers; Sudbury, MA; ISBN 0-7637-4816-6; Chapter 12; pp. 213-215; Feb. 28, 2005.
Crampon, M.-A. et al. Nerve Cuff Electrode With Shape Memory Alloy Armature: Design and Fabrication. Bio-Medical Materials and Engineering. 12 (4): 397-410. (year of pub. sufficiently earlier than effective US filing date and any foreign priority date) 2002.
Cuoco, Jr., Frank A. et al. Measurement of External Pressures Generated by Nerve Cuff Electrodes. IEEE Transactions on Rehabilitation Engineering. 8 (1): 35-41. Mar. 2000.
Cyberonics, Inc. Equity Research dated Jan. 16, 2003 by Pacific Growth Equities pp. 1-14.
Denny, N. M. et al. Evaluation of an Insulated Tuohy Needle System for the Placement of Interscalene Brachial Plex Catheters. Anaesthesia. 58 (6): 554-7. (Abstract Only). Jun. 2003.
Dorsal Root Ganglion; www.biology-online.org/dDorsal_root_ganglion; downloaded Nov. 5, 2013; 4 pgs.
Dreyfuss, Paul et al. Efficacy and Validity of Radiofrequency Neurotomy for Chronic Lumbar Zygapophysial Joint Pain. Spine. 25 (10): 1270-1277. May 15, 2000.
Dubuisson, D. Treatment of Occipital Neuralgia by Partial Posterior Rhizotomy at C1-3. J Neurosurg. 82 (4): 581-6. (Abstract Only). Apr. 1995.
Eschenfelder, Sebastian et al. Dorsal Root Section Elicits Signs of Neuropathic Pain Rather than Reversing Them in Rats With L5 Spinal Nerve Injury. Pain. 87 (2): 213-219. Aug. 2000.
Firth, Ava et al. Development of a Scale to Evaluate Postoperative Pain in Dogs. J Am Vet Med Assoc. 214 (5): 651-659. Mar. 1, 1999.
Garcia Cosamalon, P.J. et al. Dorsal Percutaneo Radiofrequency Rhizotomy Guided With CT Scan in Intercostal Neuralgias. Technical note. Acta Neurochir (Wien). 109(3-4): 140-1. (year of pub. Sufficiently earlier than effective US filing date and any foreign priority date) 1991.
Giorgi, C. et al. Surgical Treatment of Glossopharyngeal Neuralgia and Pain From Cancer of the Nasopharynx. A 20-Year Experience. J Neurosurg. 61 (5): 952-5. (Abs. Only). Nov. 1984.
Gocer, A.I. et al. Percutaneous Radiofrequency Rhizotomy of Lumbar Spinal Facets the Results of 46 cases. Neurosurg Rev. 20 (2): 114-6. (Abstract Only). (year of pub. sufficiently earlier than effective US filing date and any foreign priority date) 1997.
Haller, H. et al. Treatment of Chronic Neuropathic Pain After Traumatic Central Cervical Cord Lesion with Gabapentin. Journal of Neural Transmission. 110 (9): 977-981. Sep. 2003.
Herron, L.D. Selective Nerve Root Block in Patient Selection for Lumbar Surgery: Surgical Results. J Spinal Disord. 2 (2): 75-9. (Abstract Only). Jun. 1989.
Higuchi, Yoshinori, et al. Exposure of the Dorsal Root Ganglion in Rats to Pulsed Radiofrequency Currents Activates Dorsal Horn Lamina I and II Neurons. Neurosurgery. 50 (4): 850-856. Apr. 2002.
Holsheimer, J. et al. Effects of Electrode Geometry and Combination on Nerve Fibre Selectivity in Spinal Cord Stimulation. Medical & Biological Engineering & Computing. 33 (5): 676-682. Sep. 1995.
Horsch, S. et al. Epidural spinal cord stimulation in the treatment of severe peripheral arterial occlusive disease; Annals of Vascular Surgery; 8(5): 468-74. Sep. 1994.
Igarashi, T. et al. Lysis of Adhesions and Epidural Injection of Steroid/Local Anaesthetic During Epiduroscopy Potentially Alleviate Low Back and Leg Pain in Elderly Patients With Lumbar Spinal Stenosis. British Journal of Anaesthesia. 93 (2): 181-7.Aug. 2004.
Julius, David et al. Molecular Mechanisms of Nociception. Nature. 413 (6852): 203-210. Sep. 13, 2001.
Kanpolat, Yucel et al. Percutaneo Controlled Radiofrequency Trigeminal Rhizotomy for the Treatment of Idiopathic Trigeminal Neuralgia: 25-Year Experience with 1600 Patients. Neurosurgery. 48 (3): 524-534. Mar. 2001.
Kapadia, N. P. et al. Gabapentin for Chronic Pain in Spinal Cord Injury: A Case Report. Arch Phys Med Rehabil. 81 (10): 1439-41. (Abstract Only). Oct. 2000.
Kapoor, Vibhu et al. Refractory Occipital Neuralgia: Preoperative Assessment With CT-Guided Nerve Block Prior to Dorsal Cervical Rhizotomy. American Journal of Neuroradiology. 24 (10): 2105-10. Nov.-Dec. 2003.
Karai, Laszlo et al. Deletion of Vanilloid Receptor 1-Expressing Primary Afferent Neurons for Pain Control. Journal of Clinical Investigation. 113 (9): 1344-1352. May 2004.
Kline, David G. et al. Management and Results of Sciatic Nerve Injuries: A 24-Year Experience. Journal of Neurosurgery. 89 (1): 13-23. Jul. 1998.
Kobayashi, Shigeru et al. Pathology of Lumbar Nerve Root Compression Part 1: Intraradicular Inflammatory Changes Induced by Mechanical Compression. Journal of Orthopaedic Research. 22 (1): 170-179. Jan. 2004.
Kobayashi, Shigeru et al. Pathology of Lumbar Nerve Root Compression Part 2: Morphological and Immunohistochemical Changes of Dorsal Root Ganglion. Journal of Orthopaedic Research. 22 (1): 180-188. Jan. 2004.
Kocsis et al.; NR2B receptors are involved in the mediation of spinal segmental reflex potentials but not in the cumulative motoneuronal depolarization in vitro; Brain Research Bulletin, Elsevier Science Ltd.; vol. 64; No. 2; pp. 133-138; Aug. 30, 2004.
Koszewski, W. et al. [The DREZ Lesion as an Effective Treatment for Chronic Hypothetically Post-Herpetic Neuropathic Pain. Case Report and Review of Literature]. Neurol Neurochir Pol. 37 (4): 943-53. (Abstract Only). (year of pub. sufficiently earlier than effective US filing date and any foreign priority date) 2003.
Lawrence, Stephen M. et al. Long-Term Biocompatibility of Implanted Polymer-Based Intrafascicular Electrodes. Journal of Biomedical Materials Research. Article first publ. online: 63 (5): 501-506. Jul. 31, 2002.

(56) References Cited

OTHER PUBLICATIONS

Lee, In-Seop et al. Characterization of Iridium Film as a Stimulating Neural Electrode. Biomaterials. 23 (11): 2375-2380. Jun. 2002.
Lew, Henry L. et al. Preganglionic Approach to Transforaminal Epidural Steroid Injections. Am. J. Phys. Med. Rehabil. 83 (5): 378. May 2004.
Lopez et al.; Excitatory and inhibitory effects of serotonin on spinal nociceptive reflexes . . . ; (Database Biosis Biosciences information service, Philadelphia, PA, US, XP002567533, accession No. PREV200100573757); Abstract; (year of pub. sufficiently earlier than effective US filing date and any foreign priority date) 2001.
Ma et al.; Enhanced excitability of dissociated primary sensory neurons after chronic compression of the dorsal root ganglion in the rat; Pain; 113(1-2); pp. 106-112; Jan. 2005.
Maher, C.O. et al. Lateral Exit-Zone Stenosis and Lumbar Radiculopathy. J Neurosurg. 90 (1 Suppl): 52-8. Jan. 1999. (Abstract Only).
Mailley, Sophie et al. Thin Film Platinum Cuff Electrodes for Neurostimulation: In Vitro Approach of Safe Neurostimulation Parameters. Bioelectrochemistry. 63(1-20: 359-364. Jun. 2004.
Masini, Michelle et al. Activated Pyrolytic Carbon Tip Pacing Leads: An Alternative to Steroid-Eluting Pacing Leads? PACE. 19(11 Pt 2): 1832-1835. Nov. 1996.
Mayfield Clinic for Brain & Spine; printed from http://www.mayfieldclinic.com/PE-AnatSpine.htm (last updated Jan. 2013); 7 pages.
medicinenet.com; Definition of Lateral; printed from http://www.medterms.conn/script/main/art.asp?articlekey=6226 (on Jun. 4, 2014); 3 pages.
Medtronic, Inc. Equity Research dated Dec. 18, 2002 by Pacific Growth Equities pp. 1-20.
Medtronic. Analysis of Sales/Earnings-F1Q05: Many Gives and Takes in the Quarter dated Aug. 20, 2004 by Morgan Stanley pp. 1-25.
Methods of Placement of Neurostimulation Lead, Infusion, Catheter, and/or Sensor Via Peripheral Vasculature. From IP.com PriorArtDatabase—Apr. 10, 2003—#000012136 http://www.priorartdatabase.com/IPCOM/000012136.
Modern Ideas: The Gate Control Theory of Chronic Pain. Spine-Health.com: Your Comprehensive Resource for Back Pain. http://www.spine-health.com/topics/cd/pain/chronic_pain_theories/chronic_pain_theory02.html (accessed Feb. 24, 2006); 2 pages.
Mond, Harry G. et al. Implantable Transveno Pacing Leads: The Shape of Things to Come. PACE. 27: 887-893. Jun. 2004.
Monti, Enrico. Peripheral Nerve Stimulation: A Percutaneous Minimally Invasive Approach. Neuromodulation. 7 (3): 193. Jul. 2004. (Abstract Only).
Myles et al.; Effects of different methods of peripheral nerve repair on the number and distribution of muscle afferent neurons in rat dorsal root ganglion; J Neurosurg.; 77(3); pp. 457-462; Sep. 1992.
Nannini et al.; Muscle recruitment with intrafascicular electrodes; IEEE Trans on Biomedical Engineering; vol. 38; No. 8; pp. 769-776; Aug. 1991.
Naples, Gregory G. A Spiral Nerve Cuff Electrode for Peripheral Nerve Stimulation. IEEE Transactions on Biomedical Engineering. 35 (11): 905-916. Nov. 1988.
Narozny, Martin et al. Therapeutic Efficacy of Selective Nerve Root Blocks in the Treatment of Lumbar Radicular Leg Pain. Swiss Med Wkly. 131(5-6): 75-80. Feb. 2001.
Nashold, Blaine S. et al. Peripheral Nerve Stimulation for Pain Relief Using a Multicontact Electrode System. Technical note. Journal of Neurosurgery. 51 (6): 872-873. Dec. 1979.
Nashold, Blaine S. et al. Long-Term Pain Control by Direct Peripheral-Nerve Stimulation. The Journal of Bone and Joint Surgery. 64 (1): 1-10. Jan. 1982.
Neumann, Simona et al. Regeneration of Sensory Axons Within the Injured Spinal Cord Induced by Intraganglionic cAMP Elevation. Neuron. 34 (6): 885-93. Jun. 13, 2002.
Nielson, K.D. et al. Peripheral Nerve Injury From Implantation of Chronic Stimulating Electrodes for Pain Control. Surg Neurol. 5 (1): 51-3. (Abstract Only).Jan. 1976.

North, Richard B. et al. Dorsal Root Ganglionectomy for Failed Back Surgery Syndrome: A 5-Year Follow-Up Study. J Neurosurg. 74(2): 236-242. Feb. 1991.
North, Richard B. et al. Chapter 123: Current Concepts in the Neurosurgical Management of Persistent Pain (pp. 1634-1637). Operative Neurosurgical Techniques 4th Edition (Henry H. Schmidek et al. eds.). Philadelphia: W.B. Saunders Company. Publ. date: Aug. 18, 2000.
Nygaard, Oystein P. et al. The Function of Sensory Nerve Fibers in Lumbar Radiculopathy: Use of Quantitative Sensory Testing in the Exploration of Different Populations of Nerve Fibers and Dermatomes. Spine. 23 (3): 348-352. Feb. 1, 1998.
Obata, K. et al. Activation of Extracellular Signal-Regulated Protein Kinase in the Dorsal Root Ganglion Following Inflammation Near the Nerve Cell Body. Neuroscience. 126 (4): 1011-1021. Accepted Apr. 22, 2004.
Obata, Koichi, et al. Expression of Neurotrophic Factors in the Dorsal Root Ganglion in a Rat Model of Lumbar Disc Herniation. Pain. 99 (1-2): 121-132. Sep. 2002.
Olby, Natasha J. et al. Development of a Functional Scoring System in Dogs With Acute Spinal Cord Injuries. Am J Vet Res. 62(10): 1624-1628. Oct. 2001.
Parlier-Cuau, Caroline et al. Symptomatic Lumbar Facet Joint Synovial Cysts: Clinical Assessment of Facet Joint Steroid Injection After 1 and 6 Months and Long-Term Follow-Up in 30 Patients. Radiology. 210 (2): 509-513. Feb. 1999.
Pedrolli, C. et al. [Dorsolumbar Arachnoid Cysts. A Case Report]. Recenti Prog Med. 81 (11): 699-701. Nov. 1990. (Abstract Only).
The Peripheral Nervous System; http://cnx.org/content/m44751/latest; downloaded Nov. 5, 2013; 7 pgs.
Prats-Galino et al.; Representations of hindlimb digits in rat dorsal root ganglia; J Comp Neurol; 408(1); pp. 137-145; May 24, 1999.
Rodriguez, Francisco J. et al. Polyimide Cuff Electrodes for Peripheral Nerve Stimulation. Journal of Neuroscience Methods. 98 (2): 105-118. Jun. 1, 2000.
Rokugo, Tomoyuki et al. A Histochemical Study of Substance P in the Rat Spinal Cord: Effect of Transcutaneo Electrical Nerve Stimulation. J Nippon Med Sch. 69 (5): 428-433. Oct. 2002.
Romero, E. et al. Neural Morphological Effects of Long-Term Implantation of the Self-Sizing Spiral Cuff Nerve Electrode. Medical & Biological Engineering & Computing. 39 (1): 90-100. Jan. 2001.
Rongstad, K. et al. Popliteal Sciatic Nerve Block for Postoperative Analgesia. Foot Ankle Int. 17 (7): 378-82. Jul. 1996. (Abstract Only).
Ruetten, S. et al. Endoscopic Surgery of the Lumbar Epidural Space (Epiduroscopy): Results of Therapeutic Intervention in 93 Patients. Minim Invasive Neurosurg. 46 (1): 1-4. Feb. 2003. (Abstract Only).
Sairyo, K. et al. A New Endoscopic Technique to Decompress Lumbar Nerve Roots Affected by Spondylolysis. Technical Note. J Neurosurg. 98(3): 290-3. Apr. 2003. (Abstract Only).
Salame, K. et al. Surgical Treatment of Spasticity by Selective Posterior Rhizotomy 30 Years Experience. Isr Med Assoc J. 5 (8): 543-6. Aug. 2003. (Abstract Only).
Saris, S.C. et al. Sacrococcygeal Rhizotomy for Perineal Pain. Neurosurgery. 19 (5): 789-93. Nov. 1986. (Abstract Only).
Sauvage, P.J. et al. Intraspinal Synovial Cysts of the Lumbar Spine: Imaging Findings and Treatment; [Kystes Synoviaux Intraspinaux Lombaires: Imagerie et Traitement Par Infiltration. A Propos De. (year of pub. sufficiently earlier than effective US filing date and any foreign priority date) 2000.
Schwartzman, Robert J. et al. Neuropathic Central Pain: Epidemiology, Etiology, and Treatment Options. Arch Neurol. 58 (10): 1547-1550. Oct. 2001.
Sedan, R. et al. Therapeutic Electrical Neurostimulation. French Language Society of Neurosurgery—28th Annual Congress—Athens, May 29-30, 1978. Neurochirurgie. 24: 3-& Suppl. 1 (in French with English Summary pp. 121-125.).
Sheth, Rishi N. et al. Mechanical Hyperalgesia After an L5 Ventral Rhizotomy or an L5 Ganglionectomy in the Rat. Pain. 96: 63-72. Mar. 2002.
Siddall, Philip J. et al. Persistent Pain as a Disease Entity: Implications for Clinical Management. Anesth Analg. 99: 510-20. Aug. 2004.

(56) References Cited

OTHER PUBLICATIONS

Silvers, H.R. Lumbar Percutaneo Facet Rhizotomy. Spine. 15 (1): 36-40. Jan. 1990. (Abstract Only).
Slappendel, R. et al. The efficacy of Radiofrequency Lesioning of the Cervical Spinal Dorsal Root Ganglion in a Double Blinded Randomized Study: No difference Between 40 Degrees C and 67 Degrees C Treatments. Pain. 73 (2): 159-63. Nov. 1997. (Abstract Only).
Sluijter, Menno E. et al. The Effects of Pulsed Radiofrequency Fields Applied to the Dorsal Root Ganglion—A Preliminary Report. The Pain Clinic. 11 (2): 109-117. (year of pub. sufficiently earlier than effective US filing date and any foreign priority date) 1998.
Smith, H.P. et al. Radiofrequency Neurolysis in a Clinical Model: Neuropathological Correlation. J Neurosurg. 55 (2): 246-53. Aug. 1981. (Abstract Only).
Spaic, M. et al. Drez Surgery on Con Medullaris (After Failed Implantation of Vascular Omental Graft) for Treating Chronic Pain ; Acta Neurochir(Wein). 141(12): 1309-1312. (year of pub. sufficiently earlier than effective US filing date and any foreign priority date) 1999.
Spaic, M. et al. Microsurgical DREZotomy for Pain of Spinal Cord and Cauda Equina Injury Origin: Clinical Characteristics of Pain and Implications for Surgery in a Series of 26 Patients. Acta Neurochir (Wien). 144 (5): 453-462. May 2002.
Stanton-Hicks, M. et al. Stimulation of the Central and Peripheral Nervo System for the Control of Pain. Journal of Clinical Neurophysiology. 14 (1): 46-62. Jan. 1997.
Steinbok, P. et al. Complications After Selective Posterior Rhizotomy for Spasticity in Children With Cerebral Palsy. Pediatr Neurosurg. 28 (6): 300-13. Jun. 1998. (Abstract Only).
Stolker, Robert J. et al. The Treatment of Chronic Thoracic Segmental Pain by Radiofrequency Percutaneo Partial Rhizotomy. J Neurosurg. 80(6): 986-992. Jun. 1994.
Strait, T.A. et al. Intraspinal Extradural Sensory Rhizotomy in Patients With Failure of Lumbar Disc Surgery. J Neurosurg. 54(2): 193-6. Feb. 1981. (Abstract Only).
Taha, J.M. et al. Long-Term Results of Radiofrequency Rhizotomy in the Treatment of Cluster Headache. Headache. 35 (4): 193-6. Apr. 1995. (Abstract Only).
Taub, Arthur at al. Dorsal Root Ganglionectomy for Intractable Monoradicular Sciatica: a Series of 61 Patients. Stereotact Funct Neurosurg. 65 (1-4): 106-110. (year of pub. sufficiently earlier than effective US filing date and any foreign priority date) 1995.
Uematsu, Sumio. Chapter 106: Percutaneo Electrothermocoagulation of Spinal Nerve Trunk, Ganglion, and Rootlets (pp. 1207-1221). Operative Neurosurgical Techniques, Indications, Methods and Results 2nd edition. (Henry H. Schmidek et al. eds.). (year of pub. sufficiently earlier than effective US filing date and any foreign priority date) 1988.
Van Zundert, Jan et al. Pulsed Radiofrequency in Chronic Pain Management: Looking for the Best Use of Electrical Current. World Institute of Pain. 5 (2): 74-76. Jun. 2005.
Van De Kraats, Everine B. et al. Noninvasive Magnetic Resonance to Three-Dimensional Rotational X-Ray Registration of Vertebral Bodies for Image-Guided Spine Surgery. Spine. 29 (3): 293-297. Feb. 2004.
Van Kleef, M. et al. Effects and Side Effects of a Percutaneo Thermal Lesion of the Dorsal Root Ganglion in Patients with Cervical Pain Syndrome. Pain. 52 (1): 49-53. Jan. 1993.
Van Kleef, M. et al. Radiofrequency Lesion Adjacent to the Dorsal Root Ganglion for Cervicobrachial Pain: A Prospective Double Blind Randomized Study. Neurosurgery. 38 (6): 1127-31. Jun. 1996.
Van Kleef, Maarten et al. Chapter 160: Radiofrequency Lesions in the Treatment of Pain of Spinal Origin (pp. 1585-1599). Textbook of Stereotactic and Functional Neurosurgery 1st Edition. (Philip L. Gildenberg et al. eds.). New York: McGraw-Hill. (year of pub. sufficiently earlier than effective US filing date and any foreign priority date) 1998.
Van Zundert, J. et al. Pulsed and Continuous Radiofrequency Current Adjacent to the Cervical Dorsal Root Ganglion of the Rat Induces Late Cellular Activity in the Dorsal Horn. Anesthesiology. 102 (1): 125-31. Jan. 2005.
Vaughan, R. Percutaneous Radiofrequency Gangliotomy in the Treatment of Trigeminal Neuralgia and Other Facial Pain. Aust N Z J Surg. 45 (2): 203-7. May 1975. (Abstract Only).

Viton, J.-M. et al. Short-Term Assessment of Periradicular Corticosteroid Injections in Lumbar Radiculopathy Associated With Disc Pathology. Neuroradiology. 40 (1): 59-62. Jan. 1998.
Viton, J.M. et al. Short-Term Evaluation of Periradicular Corticosteroid Injections in the Treatment of Lumbar Radiculopathy Associated With Disc Disease. Rev Rhum Engl Ed. 65 (3): 195-200. Mar. 1998. (Abstract Only).
Wagner, A.L. et al. Selective Nerve Root Blocks. Tech Vasc Intery Radiol. 5 (4): 194-200. Dec. 2002. (Abstract Only).
Waxman et al.; Sodium channels, excitability of primary sensory neurons, and the molecular basis of pain; Muscle Nerve; 22(9); pp. 1177-1187; Sep. 1999.
Weiner, Richard L. The Future of Peripheral Nerve Neurostimulation. Neurological Research. 22 (3): 299-304. Apr. 2000.
Weiner, Richard L. Peripheral Nerve Neurostimulation. Neurosurgery Clinics of North America. 14 (3): 401-408. Jul. 2003.
Weinstein, James et al. The Pain of Discography. Spine. 13(12):1344-8. Dec. 1988.
Wedley et al. Handbook of Clinical Techniques in the Management of Chronic Pain. Taylor & Francis; pp. 17-19. Nov. 27, 1996.
Wessels et al.; A rostrocaudal somatotopic organization in the brachial dorsal root ganglia of neonatal rats; Clin Neurol Neurosurg; 95 Suppl; pp. S3-S11; (year of pub. sufficiently earlier than effective US filing date and any foreign priority date) 1993.
Wessels et al.; Evidence for a rostrocaudal organization in dorsal root ganglia during development as demonstrated by intra-uterine WGA-HRP injections into the hindlimb of rat fetuses; Brain Res Dev Brain Res; 54(2); pp. 273-281; Jul. 1, 1990.
Wessels at al.; Somatotopic organization in the sensory innervation of the rat hindlimb during development . . . ; Eur J Morphol; 28(2-4); pp. 394-403; (year of pub. sufficiently earlier than effective US filing date and any foreign priority date) 1990.
Wessels et al.; The rostrocaudal organization in the dorsal root ganglia of the rat: a consequence of plexus formation?; Anat Embryol (Berl); 190(1); pp. 1-11; Jul. 1994.
Wetzel, F. Todd et al. Extradural Sensory Rhizotomy in the Management of Chronic Lumbar Radiculopathy: A Minimum 2-Year Follow-up Study. Spine. 22 (19): 2283-2291. Oct. 1, 1997.
Wetzel, F.T. Chronic Benign Cervical Pain Syndromes: Surgical Considerations. Spine. 17 (10 Suppl): S367-74. Oct. 1992. (Abstract Only).
Wetzel, F.T. et al. The Treatment of Chronic Extremity Pain in Failed Lumbar Surgery. The Role of Lumbar Sympathectomy. Spine. 17 (12): 2367-8. Dec. 1992. (Abstract Only).
White, P.F. et al. The Use of a Continuous Popliteal Sciatic Nerve Block After Surgery Involving the Foot and Ankle: Does It Improve the Quality of Recovery? Anesth Analg. 97 (5): 1303-9. Nov. 2003. (Abstract Only).
Whitworth, Louis Anthony et al. Application of Spinal Ablative Techniques for the Treatment of Benign Chronic Painful Conditions. Spine. 27 (22): 2607-2612. Nov. 15, 2002.
Wilkinson, H.A. et al. Sensory Ganglionectomy: Theory, Technical Aspects, and Clinical Experience. J Neurosurg. 95(1): 61-6. Jul. 2001. (Abstract Only).
Wong, C.B. et al. Clinical Outcomes of Revision Lumbar Spinal Surgery: 124 Patient With a Minimum of Two Years of Follow-Up. Chang Gung Med J. 25 (3): 175-82. Mar. 2002. (Abstract Only).
Wright, Robert E. et al. Neurostimulation of the L2 Dorsal Root Ganglion for Intractable Disc Pain: Description of a Novel Technique. Presented at the IFESS. (year of pub. sufficiently earlier than effective US filing date and any foreign priority date) 1998.
Wu, Gang et al. Early Onset of Spontaneous Activity in Uninjured C-Fiber Nociceptors After Injury to Neighboring Nerve Fibers. Journal of Neuroscience. 21 (8): RC140. Apr. 15, 2001.
Yamashita, Toshihiko et al. A Quantitative Analysis of Sensory Function in Lumbar Radiculopathy Using Current Perception Threshold Testing. Spine. 27 (14): 1567-1570. Jul. 15, 2002.
Yoshida, Hirotoshi et al. Lumbar Nerve Root Compression Caused by Lumbar Intraspinal Gas: Report of Three Cases. Spine. Feb. 1, 1997, vol. 22 (3): 348-351.
Young, R.F. Chapter 161: Dorsal Rhizotomy and Dorsal Root Ganglionectomy (pp. 3442-3451). Neurological Surgery 4th Edition. Jan. 15, 1996. (Julian R. Youmans ed.). Philadelphia: W.B. Saunders Company.

* cited by examiner

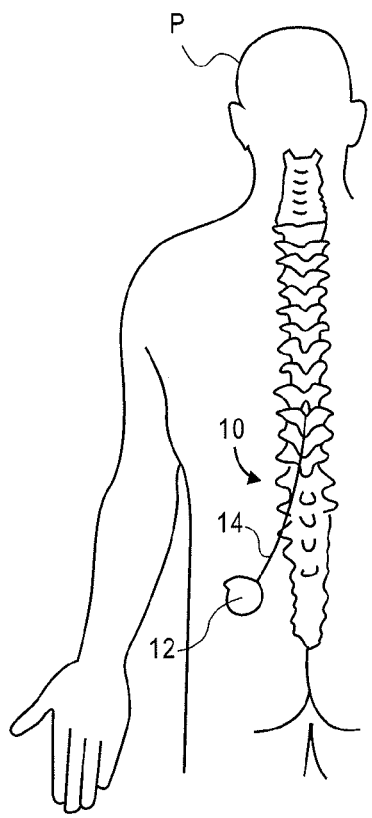 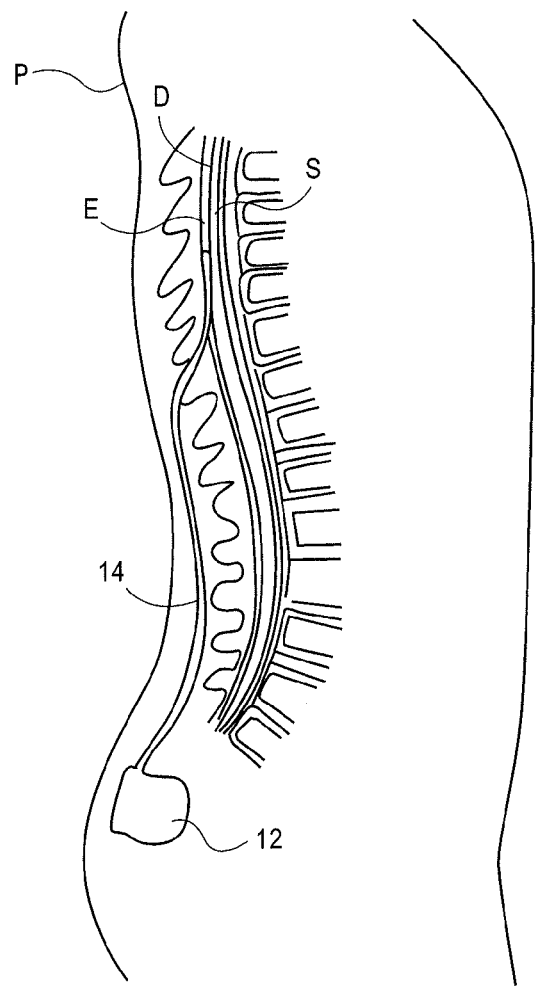
FIG. 1A
(PRIOR ART)
FIG. 1B
(PRIOR ART)

PATIENT NO. 1

| Row No. | Lead No. | Contact 1 | Contact 2 | Contact 3 | Contact 4 | Amplitude (µA) | Pulse Width (µS) | Frequency (Hz) | Affected Body Region |
|---|---|---|---|---|---|---|---|---|---|
| 1 | 2 | N | N | + | - | 800 | 60 | 70 | foot bottom |
| 2 | 2 | N | N | + | - | 1.8 mA | 60 | 70 | calf and foot |
| 3 | 2 | N | N | + | - | 2.25 mA | 60 | 70 | calf, foot and back of knee |
| 4 | 2 | N | N | + | - | 2.75 mA | 60 | 70 | calf, foot, back of knee and hip |
| 5 | 2 | N | N | + | - | 3.0 mA | 60 | 70 | calf, foot, back of knee, hip and buttock |

FIG. 27

PATIENT NO. 2

| Row No. | Lead No. | Contact 1 | Contact 2 | Contact 3 | Contact 4 | Amplitude (µA) | Pulse Width (µS) | Frequency (Hz) | Affected Body Region |
|---|---|---|---|---|---|---|---|---|---|
| 1 | 1 | N | N | + | - | 325 | 120 | 60 | calf light |
| 2 | 1 | N | N | + | - | 350 | 120 | 60 | calf and knee |
| 3 | 1 | N | N | + | - | 425 | 120 | 60 | calf and knee, radiating up to hip |
| 4 | 1 | N | - | + | - | 275 | 120 | 60 | calf to ankle |
| 5 | 1 | N | - | + | - | 625 | 120 | 60 | above knee and to side of thigh |
| 6 | 1 | N | + | - | + | 625 | 120 | 60 | front of calf |
| 7 | 1 | N | + | - | + | 650 | 120 | 60 | front of calf, and knee |
| 8 | 1 | N | + | - | + | 425 | 240 | 60 | calf dull |
| 9 | 1 | N | + | - | + | 525 | 240 | 60 | all calf up to knee radiating up leg |

FIG. 28

SELECTIVE STIMULATION SYSTEMS AND SIGNAL PARAMETERS FOR MEDICAL CONDITIONS

CROSS-REFERENCES TO RELATED APPLICATIONS

This application is a divisional of U.S. patent application Ser. No. 12/607,009, titled "SELECTIVE STIMULATION SYSTEMS AND SIGNAL PARAMETERS FOR MEDICAL CONDITIONS," filed Oct. 27, 2009, which claims priority under 35 U.S.C. 119(e) to U.S. Provisional Patent Application No. 61/108,836, titled "SELECTIVE STIMULATION SYSTEMS AND SIGNAL PARAMETERS FOR PAIN MANAGEMENT", filed Oct. 27, 2008, each of which is herein incorporated by reference in its entirety.

STATEMENT AS TO RIGHTS TO INVENTIONS MADE UNDER FEDERALLY SPONSORED RESEARCH OR DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

BACKGROUND OF THE INVENTION

Pain of any type is the most common reason for physician consultation in the United States, prompting half of all Americans to seek medical care annually. It is a major symptom in many medical conditions, significantly interfering with a person's quality of life and general functioning. Diagnosis is based on characterizing pain in various ways, according to duration, intensity, type (dull, burning, throbbing or stabbing), source, or location in body. Usually if pain stops without treatment or responds to simple measures such as resting or taking an analgesic, it is then called 'acute' pain. But it may also become intractable and develop into a condition called chronic pain in which pain is no longer considered a symptom but an illness by itself.

The application of specific electrical energy to the spinal cord for the purpose of managing pain has been actively practiced since the 1960s. It is known that application of an electrical field to spinal nervous tissue can effectively mask certain types of pain transmitted from regions of the body associated with the stimulated nervous tissue. Such masking is known as paresthesia, a subjective sensation of numbness or tingling in the afflicted bodily regions. Such electrical stimulation of the spinal cord, once known as dorsal column stimulation, is now referred to as spinal cord stimulation or SCS.

FIGS. 1A-1B illustrate conventional placement of an SCS system 10. Conventional SCS systems include an implantable power source or implantable pulse generator (IPG) 12 and an implantable lead 14. Such IPGs 12 are similar in size and weight to cardiac pacemakers and are typically implanted in the buttocks or abdomen of a patient P. Using fluoroscopy, the lead 14 is implanted into the epidural space E of the spinal column and positioned against the dura layer D of the spinal cord S, as illustrated in FIG. 1B. The lead 14 is implanted either through the skin via an epidural needle (for percutaneous leads) or directly and surgically through a mini laminotomy operation (for paddle leads or percutaneous leads). A laminotomy is a neurosurgical procedure that removes part of a lamina of the vertebral arch. The laminotomy creates an opening in the bone large enough to pass one or more leads through.

FIG. 2 illustrates example conventional paddle leads 16 and percutaneous leads 18. Paddle leads 16 typically have the form of a slab of silicon rubber having one or more electrodes 20 on its surface. Example dimensions of a paddle lead 16 are illustrated in FIG. 3. Percutaneous leads 18 typically have the form of a tube or rod having one or more electrodes 20 extending therearound. Example dimensions of a percutaneous lead 18 are illustrated in FIG. 4.

Implantation of a percutaneous lead 18 typically involves an incision over the low back area (for control of back and leg pain) or over the upper back and neck area (for pain in the arms). An epidural needle is placed through the incision into the epidural space and the lead is advanced and steered over the spinal cord until it reaches the area of the spinal cord that, when electrically stimulated, produces a tingling sensation (paresthesia) that covers the patient's painful area. To locate this area, the lead is moved and turned on and off while the patient provides feedback about stimulation coverage. Because the patient participates in this operation and directs the operator to the correct area of the spinal cord, the procedure is performed with conscious sedation.

Implantation of paddle leads 16 typically involves performing a mini laminotomy to implant the lead. An incision is made either slightly below or above the spinal cord segment to be stimulated. The epidural space is entered directly through the opening in the bone and a paddle lead 16 is placed over the region to stimulate the spinal cord. The target region for stimulation usually has been located before this procedure during a spinal cord stimulation trial with percutaneous leads 18.

Although such SCS systems have effectively relieved pain in some patients, these systems have a number of drawbacks. To begin, as illustrated in FIG. 5, the lead 14 is positioned upon the spinal cord dura layer D so that the electrodes 20 stimulate a wide portion of the spinal cord and associated spinal nervous tissue (as indicated by perimeter 21). The spinal cord is a continuous body and three spinal levels of the spinal cord are illustrated. For purposes of illustration, spinal levels are sub-sections of the spinal cord S depicting that portion where the dorsal root DR and ventral root VR join the spinal cord S. The spinal nerve N divides into the dorsal root DR and the dorsal root ganglion DRG and the ventral nerve root VR each of which feed into the spinal cord S. Generally, the dorsal roots DR feed into the posterior side of the spinal cord S and the ventral roots VR feed into the anterior side of the spinal cord S. For simplicity, each level shown illustrates the nerves of only one side and a normal anatomical configuration would have similar nerves on the opposite side of the spinal cord.

FIG. 6 illustrates a cross-sectional view of the lead 14 of FIG. 5 at a spinal level. Thus, as shown, the lead 14 is positioned against the dura layer D near the midline of the spinal cord S. The electrode 20 stimulates a wide portion of the spinal cord. In this example, the lead 14 is a unidirectional paddle lead so the stimulation energy 15 (indicated by perimeter 21) extends to one side of the lead 14. Significant energy 15 is utilized to penetrate the dura layer D and cerebral spinal fluid CSF to activate fibers in the spinal column extending within the posterior side of the spinal cord S, post-synaptically to the dorsal roots. And, in cases of omnidirectional leads, even more energy may be required due to loss of energy that is directed away from the target. Sensory spinal nervous tissue, or nervous tissue from the dorsal nerve roots, transmit pain signals. Therefore, such stimulation is intended to block the transmission of pain signals to the brain with the production of a tingling sensation (paresthesia) that masks the patient's sensation of pain. However, excessive tingling may be considered undesirable. Further, the energy 15 also typically penetrates the anterior side of the spinal cord 5, stimulating the ventral horns, and consequently the ventral roots extending within the anterior side of the spinal cord S. Motor spinal nervous tissue, or nervous tissue from ventral nerve roots, transmits muscle/motor control signals. Therefore, electrical stimulation by the lead 14 often causes undesirable stimulation of the motor nerves in addition to the sensory spinal nervous tissue. The result is undesirable muscle contraction.

Because the electrodes span several levels and because they stimulate medial to spinal root entry points, the generated stimulation energy 15 stimulates or is applied to more than one type of nerve tissue on more than one level. Moreover, these and other conventional, non-specific stimulation systems also apply stimulation energy to the spinal cord and to other neural tissue beyond the intended stimulation targets. As used herein, non-specific stimulation refers to the fact that the stimulation energy is provided to multiple spinal levels including the nerves and the spinal cord generally and indiscriminately. This is the case even with the use of programmable electrode configurations wherein only a subset of the electrodes are used for stimulation. In fact, even if the epidural electrode is reduced in size to simply stimulate only one level, that electrode will apply stimulation energy non-specifically and indiscriminately (i.e. to many or all nerve fibers and other tissues) within the range of the applied energy.

Therefore, improved stimulation systems, devices and methods are desired that enable more precise and effective delivery of stimulation energy. At least some of these objectives will be met by the present invention.

BRIEF SUMMARY OF THE INVENTION

The present invention provides devices, systems and methods for targeted treatment of a variety of conditions, particularly conditions that are associated with or influenced by the nervous system. Examples of such conditions include pain, itching, Parkinson's Disease, Multiple Sclerosis, demylenating movement disorders, spinal cord injury, asthma, chronic heart failure, obesity and stroke (particularly acute ischemia), to name a few. The present invention provides for targeted treatment of such conditions with minimal deleterious side effects, such as undesired motor responses or undesired stimulation of unaffected body regions. This is achieved by directly neuromodulating a target anatomy associated with the condition while minimizing or excluding undesired neuromodulation of other anatomies. In most embodiments, neuromodulation comprises stimulation, however it may be appreciated that neuromodulation may include a variety of forms of altering or modulating nerve activity by delivering electrical or pharmaceutical agents directly to a target area. For illustrative purposes, descriptions herein will be provided in terms of stimulation and stimulation parameters, however, it may be appreciated that such descriptions are not so limited and may include any form of neuromodulation and neuromodulation parameters.

Typically, the systems and devices are used to stimulate portions of neural tissue of the central nervous system, wherein the central nervous system includes the spinal cord and the pairs of nerves along the spinal cord which are known as spinal nerves. The spinal nerves include both dorsal and ventral roots which fuse in the intravertebral foramen to create a mixed nerve which is part of the peripheral nervous system. At least one dorsal root ganglion (DRG) is disposed along each dorsal root prior to the point of mixing. Thus, the neural tissue of the central nervous system is considered to include the dorsal root ganglions and exclude the portion of the nervous system beyond the dorsal root ganglions, such as the mixed nerves of the peripheral nervous system. Typically, the systems and devices of the present invention are used to stimulate one or more dorsal root ganglia, dorsal roots, dorsal root entry zones, or portions thereof, while minimizing or excluding undesired stimulation of other tissues, such as surrounding or nearby tissues, ventral root and portions of the anatomy associated with body regions which are not targeted for treatment. However, it may be appreciated that stimulation of other tissues are contemplated.

In a first aspect of the present invention, a system is provided stimulating at least a portion of a target dorsal root. In some embodiments, the system comprises a lead having at least one electrode, wherein the lead is configured to be positioned so that at least one of the at least one electrodes is able to stimulate the at least a portion of the target dorsal root, and an implantable pulse generator connectable with the lead, wherein the generator provides a stimulation signal to the lead which has an energy below an energy threshold for stimulating a ventral root associated with the target dorsal root while the lead is so positioned. In some embodiments, the at least a portion of the target dorsal root comprises a dorsal root ganglion.

In some embodiments, the stimulation signal has a current amplitude of less than or equal to approximately 4 mA. Optionally, the current amplitude may be less than or equal to approximately 800 µA. In some instances the at least one of the at least one electrodes has an average electrode surface area of less than or equal to approximately 6 mm$^2$. Optionally, the average electrode surface area is less than or equal to approximately 4 mm$^2$.

In some embodiments, the system further comprises a second lead having at least one electrode, wherein the second lead is configured to be positioned so that at least one of its electrodes is able to stimulate at least a portion of a second target dorsal root, and wherein the second lead is connectable to the implantable pulse generator which provides a stimulation signal to the second lead, wherein the stimulation signal to the second lead has an energy below an energy threshold for stimulating a ventral root associated with the second target dorsal root while the second lead is so positioned. In some instances, the target dorsal root and the second target dorsal root are on different spinal levels. Optionally, the stimulation signal to the lead and the stimulation signal to the second lead are different.

In a second aspect of the present invention, a system is provided for stimulating a target neural tissue of the central nervous system. In some embodiments, the system comprises a lead having at least one electrode, wherein the lead is configured to be positioned so that at least one of the at least one electrodes is able to stimulate the target neural tissue, and an implantable pulse generator connectable with the lead, wherein the generator provides a stimulation signal having a current amplitude which is less than 100 µA. Typically, the target spinal neural tissue comprises a dorsal root ganglion.

In a third aspect of the present invention, a system is provided for stimulating at least a portion of a target dorsal root, wherein the system includes a lead having at least one electrode, and wherein the lead is configured to be positioned so that at least one of the at least one electrodes is able to stimulate the at least a portion of the target dorsal root when provided a stimulation signal The system also includes an implantable pulse generator connectable with the lead, wherein the generator provides the stimulation signal which has an energy of less than approximately 100 nJ per pulse. In some embodiments, the stimulation signal has an energy of less than approximately 50 nJ per pulse. Optionally, the stimulation signal may have an energy of less than approximately 10 nJ per pulse. Typically, the at least a portion of the target dorsal root comprises a dorsal root ganglion.

In a fourth aspect of the present invention, a system is provided for stimulating at least a portion of a target dorsal root, wherein the system includes a lead having at least one electrode, wherein the lead is configured to be positioned so that at least one of the at least one electrodes is able to stimulate the at least a portion of the target dorsal root when provided a stimulation signal. The system also includes an implantable pulse generator connectable with the lead, wherein the generator provides a stimulation signal which has a current amplitude of less than 4 mA.

In a fifth aspect of the present invention, a system is provided for stimulating at least a portion of a target dorsal root, wherein the system includes a lead having at least one electrode, and wherein the lead is configured so that at least one of the at least one electrodes is positionable on or near the at least a portion of the target dorsal root. The system also includes an implantable pulse generator connectable with the lead, wherein the generator provides a stimulation signal to the at least one of the at least one electrode which selectively stimulates the at least a portion of the target dorsal root due to at least one signal parameter. In some embodiments, the at least one signal parameter includes current amplitude. In these embodiments, the current amplitude may be less than or equal to approximately 4 mA. Likewise, in some embodiments, the at least one signal parameter includes pulse width and the pulse width is less than 500 µs. Typically, the at least a portion of the target dorsal root comprises a dorsal root ganglion.

In a sixth aspect of the present invention, a system for stimulating a target dorsal root ganglion is provided comprising a lead having at least one electrode, wherein the lead is configured so that at least one of the at least one electrodes is positionable on or near the target dorsal root ganglion. The system also includes an implantable pulse generator connectable with the lead, wherein the generator energizes the at least one of the at least one electrodes which selectively stimulates the target dorsal root ganglion due to its proximity to the target dorsal root ganglion.

In a seventh aspect of the present invention, a system is provided for stimulating a target neural tissue of the central nervous system comprising a lead having at least one electrode, wherein the lead is configured to be positioned so that at least one of the at least one electrodes is able to stimulate the target neural tissue, and an implantable pulse generator connectable with the lead, wherein the generator provides a stimulation signal having a current amplitude which is adjustable in increments of 50 µA or less. In some embodiments, the current amplitude is adjustable in increments of 25 µA or less.

In another aspect of the present invention, a method is provided for stimulating at least a portion of a target dorsal root comprising positioning a lead having at least one electrode so that at least one of the at least one electrodes is on or near the at least a portion of the target dorsal root, and energizing at least one of the at least one electrodes with an energy level below an energy threshold for stimulating a ventral root associated with the target dorsal root while the lead is so positioned. In some embodiments, energizing comprises providing a stimulation signal having a current amplitude of less than or equal to approximately 4 mA. Optionally, the current amplitude is less than or equal to approximately 1.0 mA. In some embodiments, positioning the lead comprises advancing the lead using an epidural approach. In these embodiments, positioning the lead may comprise advancing the lead using an antegrade approach or a retrograde approach. It may also be appreciated that the lead may be positioned by advancing the lead using transforamenal approach from outside of the spinal column. Typically, the at least a portion of the target dorsal root comprises a dorsal root ganglion. In some embodiments, the average electrode surface area is less than or equal to approximately 4 mm².

In some embodiments, the method further comprises positioning a second lead having at least one electrode so that at least one of its at least one electrodes is on or near at least a portion of a second target dorsal root, and energizing at least one of the at least one electrodes of the second lead with an energy level below an energy threshold for stimulating a ventral root associated with the second target dorsal root while the second lead is so positioned. In some embodiments, the target dorsal root and the second target dorsal root are on different spinal levels. Likewise, in some embodiments, the energy level of the lead and the second lead are different.

In another aspect of the present invention, a method of stimulating a target spinal neural tissue within an epidural space is provided comprising positioning a lead having at least one electrode, so that at least one of the at least one electrodes is able to stimulate the target spinal neural tissue, and energizing the at least one of the at least one electrodes with a stimulation signal which has a current amplitude which is less than 100 µA.

In another aspect of the present invention, a method of stimulating at least a portion of a target dorsal root is provided comprising positioning a lead having at least one electrode, so that at least one of the at least one electrodes is able to stimulate the at least a portion of the target dorsal root and energizing the at least one of the at least one electrodes with a stimulation signal which has an energy of less than approximately 100 nJ per pulse.

In another aspect of the present invention, a method for stimulating at least a portion of a target dorsal root is provided comprising positioning a lead having at least one electrode, so that at least one of the at least one electrodes is able to stimulate the at least a portion of the target dorsal root and energizing the at least one of the at least one electrodes with a stimulation signal which has a current amplitude of less than 4 mA.

In another aspect of the present invention, a method for stimulating at least a portion of the target dorsal root is provided comprising positioning a lead having at least one electrode so that at least one of the at least one electrode is on or near the at least a portion of the target dorsal root and energizing at least one of the at least one electrodes with a stimulation signal which selectively stimulates the at least a portion of the target dorsal root due to at least one signal parameter.

In yet another aspect of the present invention, a method is provided for stimulating a target neural tissue of the central nervous system comprising positioning a lead having at least one electrode so that at least one of the at least one electrode is able to stimulate the target neural tissue, and energizing at least one of the at least one electrodes with a stimulation signal having a current amplitude which is adjustable in increments of 50 µA or less.

Due to variability in patient anatomy, pain profiles, pain perception and lead placement, to name a few, signal parameter settings will likely vary from patient to patient and from lead to lead within the same patient. Signal parameters include voltage, current amplitude, pulse width and repetition rate, to name a few. In some embodiments of the stimulation system of the present invention, the voltage provided is in the range of approximately 0-7 volts. In some embodiments, the current amplitude provided is less than approximately 4 mA, particularly in the range of approximately 0.5-2 mA, more particularly in the range of approximately 0.5-1.0 mA, 0.1-1.0 mA, or 0.01-1.0 mA. Further, in some embodiments, the pulse width provided is less than approximately 2000 µs, particularly less than approximately 1000 µs, more particularly less than approximately 500 µs, or more particularly 10-120 µs. And, in some embodiments, the repetition rate is in the range of approximately 2-120 Hz, up to 200 Hz or up to 1000 Hz.

Typically, stimulation parameters are adjusted until satisfactory clinical results are reached. Thus, there is an envelope of stimulation parameter value combinations between the threshold for DRG stimulation and ventral root stimulation for any given lead positioned in proximity to any given DRG per patient. The specific combinations or possible combinations that could be used to successfully treat the patient are typically determined perioperatively in vivo and postoperatively ex vivo and depend on a variety of factors. One factor is lead placement. The closer the desired electrodes are to the DRG the lower the energy required to stimulate the DRG. Other factors include electrode selection, the anatomy of the patient, the pain profiles that are being treated and the psychological perception of pain by the patient, to name a few. Over time, the parameter values for any given lead to treat the patient may change due to changes in lead placement, changes in impedance or other physical or psychological changes. In any case, the envelope of parameter values is exceedingly lower than those of conventional stimulation systems which require energy delivery of at least an order of magnitude higher to treat the patient's pain condition.

Given the lower ranges of parameter values, the granularity of control is also smaller in comparison to conventional stimulation systems. For example, current in a conventional stimulation system is typically adjustable in increments of 0.1 mA. In some embodiments of the present invention, this increment is larger than the entire range of current amplitude values that may be used to treat the patient. Thus, smaller increments are needed to cycle through the signal parameter values to determine the appropriate combination of values to treat the condition. In some embodiments, the system of the present invention provides control of current amplitude at a resolution of approximately 25 µA, particularly when using a current amplitude under, for example, 2 mA, however it may be appreciated that smaller increments may be used such as approximately 10 µA, 5 µA or 1 µA. In other embodiments, control of current amplitude is provided at a resolution of approximately 50 µA, particularly when using a current amplitude of, for example, 2 mA or greater. It may be appreciated that such a change in resolution may occur at other levels, such as 1 mA. Similarly, voltage in a conventional stimulation system is typically adjustable in increments of 100 mV. In contrast, some embodiments of the present invention provide control of voltage at a resolution of 50 mV. Likewise, some embodiments of the present invention provide control of pulse width at a resolution of 10 µs. Thus, it may be appreciated that the present invention provides a high granularity of control of stimulation parameters due to the low ranges of parameter values.

It may be appreciated that in some instances even lower levels of energy may be used to successfully treat a patient using the stimulation system of the present invention. The closer a lead is positioned to a target DRG, the lower the level of energy that may be needed to selectively stimulate the target DRG. Thus, signal parameter values may be lower than those stated herein with correspondingly higher granularity of control.

Such reductions in energy allows a reduction in electrode size, among other benefits. In some embodiments, the average electrode surface area is approximately 1-6 mm$^2$, particularly approximately 2-4 mm$^2$, more particularly 3.93 mm$^2$ whereas conventional spinal cord stimulators typically have a much larger average electrode surface area, such as 7.5 mm$^2$ for some leads or 12.7 mm$^2$ for traditional paddle leads. Likewise, in some embodiments an average electrode length is 1.25 mm whereas conventional spinal cord stimulators typically have an average electrode length of 3 mm. Such reduced electrode sizing allows more intimate positioning of the electrodes in the vicinity of the DRG and allows for IPGs having different control and performance parameters for providing direct and selective stimulation of a targeted neural tissue, particularly the DRG. In addition, in some embodiments the overall dimensions of one or more electrodes and the spacing of the electrodes is selected to match or nearly match the overall dimensions or size of the stimulation target.

Effective treatment of a condition may be achieved by directly stimulating a target anatomy associated with the condition while minimizing or excluding undesired stimulation of other anatomies. When such a condition is limited to or primarily affects a single dermatome, the present invention allows for stimulation of a single dermatome or regions within a dermatome (also referred to as subdermatomal stimulation).

In one aspect of the present invention, a method of treating a condition associated with a spinal neural tissue is provided, wherein the treatment is applied substantially within a single dermatome. In some embodiments, the method comprises positioning a lead having at least one electrode so that at least one of the at least one electrodes is in proximity to the spinal neural tissue within an epidural space, and energizing the at least one of the at least one electrodes so as to stimulate the spinal neural tissue causing a treatment effect within the single dermatome while maintaining body regions outside of the single dermatome substantially unaffected. In some embodiments, energizing the at least one electrode comprises energizing the at least one of the at least one electrode so as to stimulate the spinal neural tissue causing a treatment affect within a particular body region within the single dermatome while maintaining body regions outside of the particular body region substantially unaffected. Typically, the spinal neural tissue comprises a dorsal root ganglion and the treatment effect comprises paresthesia. In some embodiments, the particular body region comprises a foot.

In another aspect of the present invention, a method of treating a condition of a patient is provided, wherein the condition is associated with a portion of a dorsal root ganglion and is not substantially associated with other portions of the dorsal root ganglion. In some embodiments, the method comprises positioning a lead having at least one electrode so that at least one of the at least one electrode resides in proximity to the portion of a dorsal root ganglion, and providing a stimulating signal to the at least one of the at least one electrode so as to stimulate the portion of the dorsal root ganglion in a manner that affects the condition while not substantially stimulating the other portions. In some embodiments, the condition comprises pain. In such embodiments, affecting the condition may comprise alleviating the pain without causing a perceptible motor response.

In some embodiments, the condition is sensed by a patient at a location within a dermatome, and the other portions of the dorsal root ganglion are associated with other locations within the dermatome. It may be appreciated, that the stimulating signal may have a current amplitude of less than or equal to approximately 4 mA. Optionally, the stimulating signal may have current amplitude of less than or equal 1 mA. Typically, positioning the lead comprises advancing the lead using an epidural approach but is not so limited.

In another aspect of the present invention, a method of providing subdermatomal stimulation is provided comprising positioning a lead having at least one electrode so that at least one of the at least one electrode resides near a dorsal root ganglion within a dermatome, and providing a stimulating signal to the at least one of the at least one electrode so as to stimulate the dorsal root ganglion in a manner which affects a condition in a subdermatomal region of the dermatome.

In another aspect of the present invention, a system is provided for stimulating a portion of a dorsal root ganglion, wherein the portion of the dorsal root ganglion is associated with a particular region within a dermatome. In some embodiments, the system comprises a lead having at least one electrode, wherein the lead is configured to be positioned so that at least one of the at least one electrode is able to stimulate the portion of the dorsal root ganglion, and a pulse generator connectable with the lead, wherein the generator provides a stimulation signal to the at least one of the at least one electrode which stimulates the portion of the dorsal root ganglion to cause an effect within the particular region of the dermatome.

In some embodiments, the combination of the at least one of the at least one electrode and the stimulation signal creates an electric field having a shape which allows for stimulation of the portion of the dorsal root ganglion while substantially excluding other portions of the dorsal root ganglion. In some embodiments, the at least one of the at least one electrode comprises two electrodes spaced 0.250 inches apart from approximate center to center of each electrode. In some embodiments, stimulation signal has a current amplitude of less than or equal to approximately 4 mA. Optionally, the stimulating signal may have a current amplitude of less than or equal 1 mA. In some embodiments, the stimulation signal has an energy of less than approximately 100 nJ per pulse.

In another aspect of the present invention, a system for providing subdermatomal stimulation within a patient is provided comprising a lead having at least one electrode, wherein the lead is configured so that the at least one electrode is positionable in proximity to a dorsal root ganglion associated with a dermatome, and a pulse generator connectable with the lead. In some embodiments, the generator provides a first stimulation signal to at least one of the at least one electrode to create a first electric field which stimulates the dorsal root ganglion causing a first effect within a first body region of the dermatome and the generator provides a second stimulation signal to at least one of the at least one electrode to create a second electric field which stimulates the dorsal root ganglion causing a second effect within a second body region of the dermatome. In some instance, the first and second stimulation signals have different stimulation parameters. In some embodiments, the at least one of the at least one electrodes receiving the first stimulation signal differs from the at least one of the at least one electrodes receiving the second stimulation signal.

In some embodiments, the first and second electric fields have different shapes. Likewise, the first and second electric fields may have different sizes. In some embodiments, the first effect comprises relief from pain. In some embodiments, the first body region resides along a foot of the patient and the second body region resides along a back of the patient.

In yet another aspect of the present invention, a method for providing subdermatomal stimulation within a patient is provided comprising positioning a lead having at least one electrode in proximity to a dorsal root ganglion associated with a dermatome, applying a stimulation signal to the at least one electrode which stimulates the dorsal root ganglion causing an effect within a first body region of the dermatome, and repositioning the lead along the dorsal root ganglion so that the application of the stimulation signal to the least one electrode stimulates the dorsal root ganglion to cause a second effect within a second body region of the dermatome. In some embodiments, the first effect comprises relief from pain. In some embodiments, the first body region resides along a foot of the patient and the second body region resides along a back of the patient.

Other objects and advantages of the present invention will become apparent from the detailed description to follow, together with the accompanying drawings.

BRIEF DESCRIPTION OF THE DRAWINGS

FIGS. 1A-1B, 2, 3, 4, 5, 6 illustrate prior art.

FIG. 27 and FIG. 28 provide tables of clinical data from Patient No. 1 and Patient No. 2 respectively.

DETAILED DESCRIPTION OF THE INVENTION

In some embodiments, a target DRG is stimulated with a lead having at least one electrode thereon. The lead is advanced through the patient anatomy so that the at least one electrode is positioned on, near or about the target DRG. The lead is sized and configured so that the electrode(s) are able to minimize or exclude undesired stimulation of other anatomies. Such configuration may include a variety of design features, including signal parameters, which will be described herein.

Figure 7:
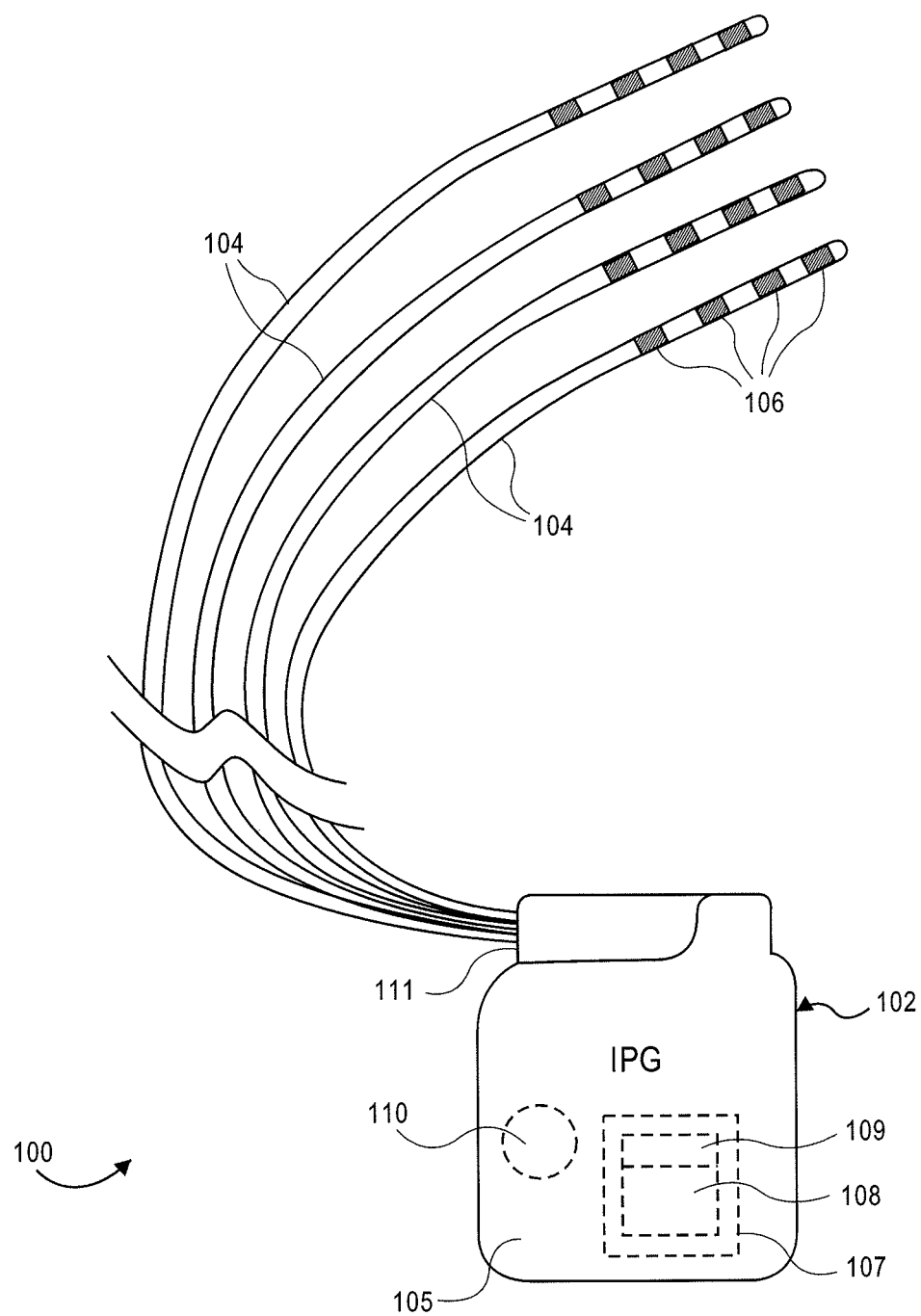
FIG. 7 illustrates an embodiment of a stimulation system of the present invention.

FIG. 7 illustrates an embodiment of an implantable stimulation system 100 of the present invention. The system 100 includes an implantable pulse generator (IPG) 102 and at least one lead 104 connectable thereto. In preferred embodiments, the system 100 includes four leads 104, as shown, however any number of leads 104 may be used including one, two, three, four, five, six, seven, eight, up to 58 or more. Each lead 104 includes at least one electrode 106. In preferred embodiments, each lead 104 includes four electrodes 106, as shown, however any number of electrodes 106 may be used including one, two, three, four five, six, seven, eight, nine, ten, eleven, twelve, thirteen, fourteen, fifteen, sixteen or more. Each electrode can be configured as off, anode or cathode. In some embodiments, even though each lead and electrode are independently configurable, at any given time the software ensures only one lead is stimulating at any time. In other embodiments, more than one lead is stimulating at any time, or stimulation by the leads is staggered or overlapping.

Referring again to FIG. 7, the IPG 102 includes electronic circuitry 107 as well as a power supply 110, e.g., a battery, such as a rechargeable or non-rechargeable battery, so that once programmed and turned on, the IPG 102 can operate independently of external hardware. In some embodiments, the electronic circuitry 107 includes a processor 109 and programmable stimulation information in memory 108.

Figure 8:
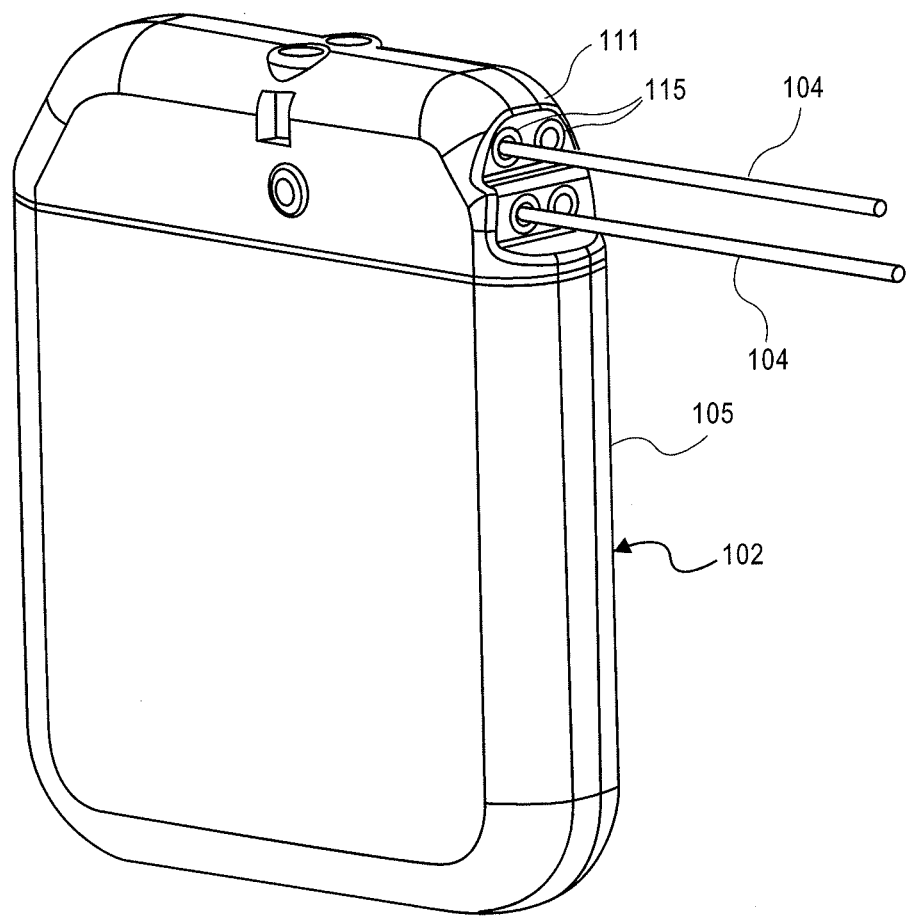
FIG. 8 provides a perspective view of an embodiment of an implantable pulse generator of the present invention.

FIG. 8 provides a perspective view of an embodiment of an IPG 102 of the present invention. Here the electronic circuitry 107 and power supply 110 are enclosed in a housing 105 (also referred to as a "case" or "can"). It may be appreciated, that alternatively, the power supply may be located outside of the housing 105, such as within an external device which supplies power to the IPG 102, such as via inductive coupling, RF or photoactivation. In some embodiments, the IPG 102 as a volume not exceeding approximately 32 cc, a thickness not exceeding approximately 1.2 cm or a weight not exceeding approximately 30 g. It may be appreciated that in other embodiments, the IPG 102 has a volume not exceeding approximately, 0.2, 5, 10, 15, 20, 30, 40, 50, 60 or 70 cc. The IPG 102 may have a variety of shapes, including an oval, circular, rounded square or rounded rectangular shape. In some embodiments, the IPG 102 has a height of approximately 61 mm, a width of approximately 48 mm and a thickness of approximately 11 mm.

In some embodiments, the housing 105 of the IPG 102 is electrically conductive. In such embodiments, the housing 105 can act as an electrode, as explained in more detail below. The at least one electrode 106 is electrically coupled to the electronic circuitry 107 by coupling the lead 104 to a connector 111 of the IPG 102. In this embodiment, each lead 104 is insertable into a separate port 115 in the IPG 102 to provide electrical connection to each lead 104.

Figure 9:
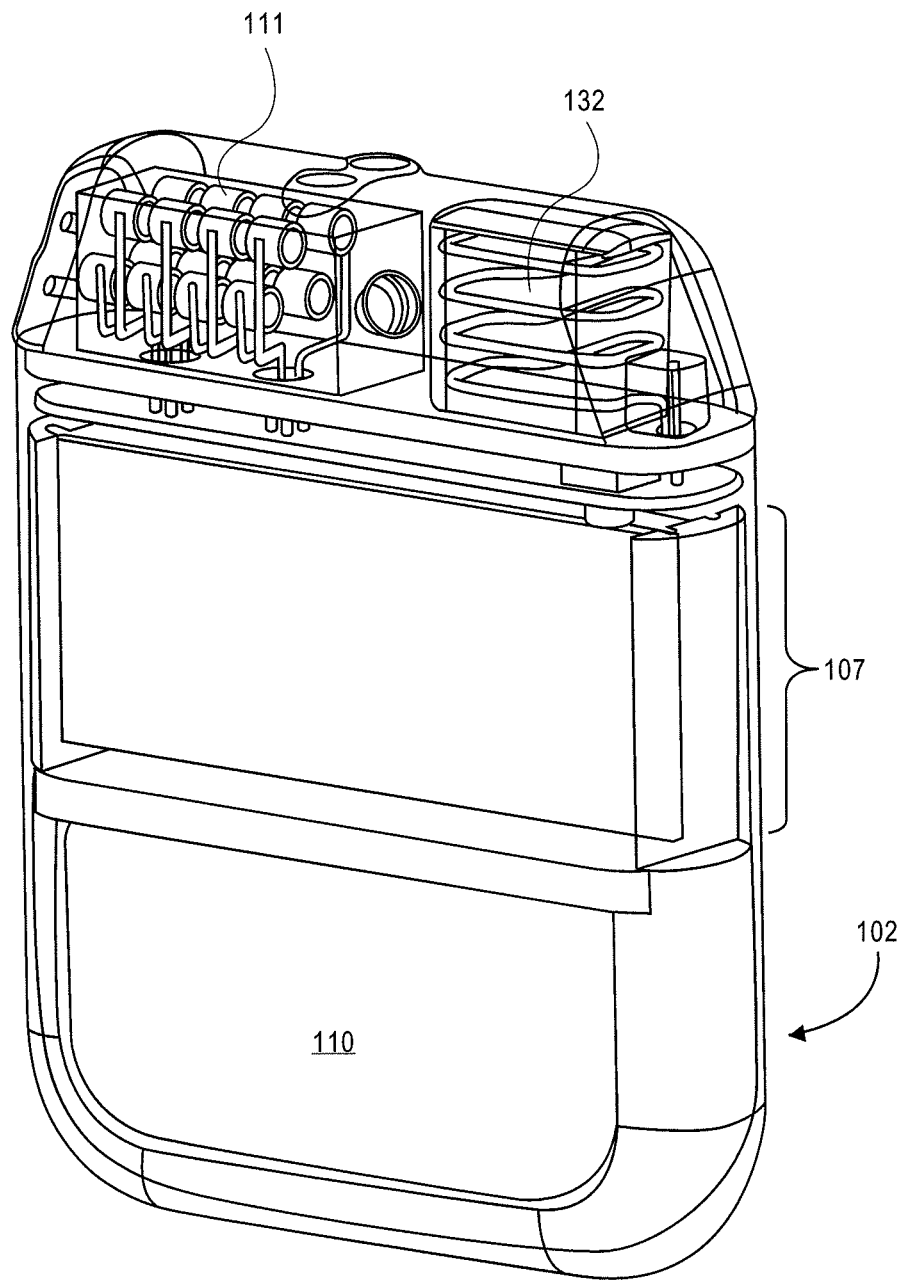
FIG. 9 illustrates the IPG of FIG. 8 with a portion of the housing removed to reveal the internal components.
Figure 10:
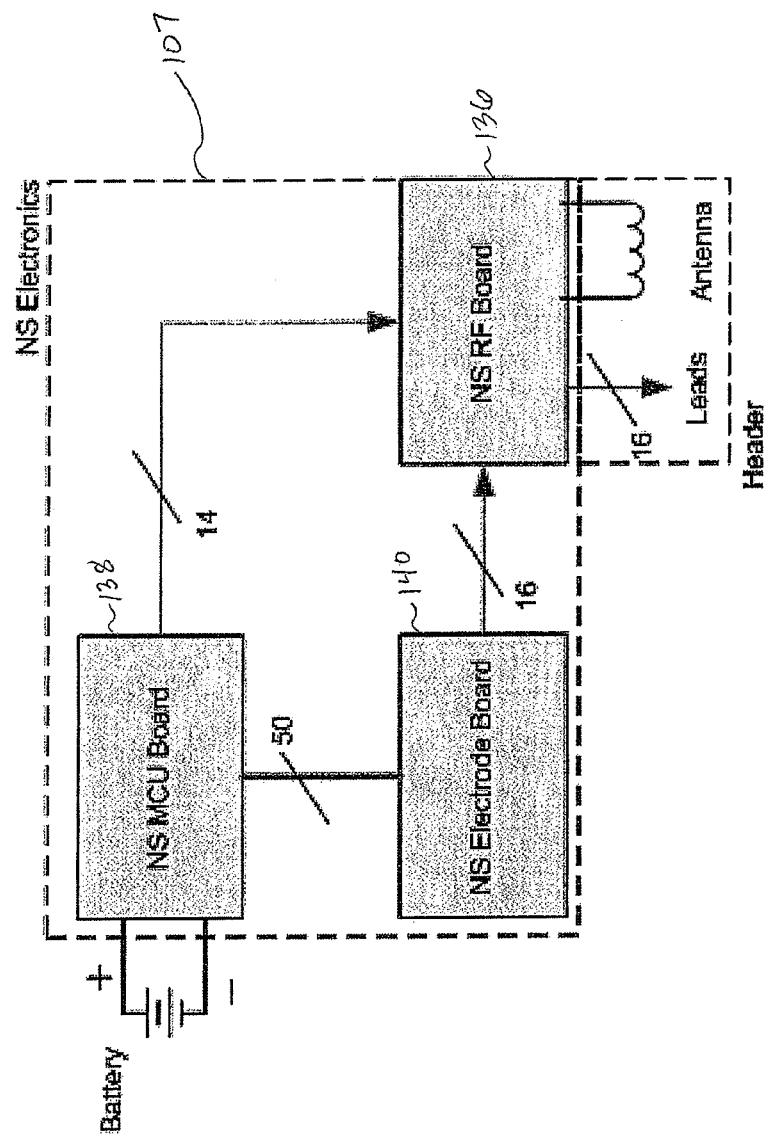
FIG. 10 provides a schematic block diagram of printed circuit boards which are part of the electronic circuitry of one embodiment of the IPG.

FIG. 9 illustrates the components within the IPG 102 of FIG. 8. In this embodiment, the internal components include a power supply 110, electronic circuitry 107, an antenna 132, and a lead connector 111. In this embodiment, the electronic circuitry 107 includes three printed circuit boards to allow the circuitry to reside in a small space. FIG. 10 provides a schematic block diagram of these boards, which include an RF board 136, an MCU board 138 and an electrode board 140. The MCU board includes a microcontroller unit (MCU) which is a small computer on a single integrated circuit comprising a CPU combined with support functions such as a crystal oscillator, timers, serial and analog I/O etc. Program memory, such as in the form of NOR flash or OTP ROM, may also be included on the chip, as well as RAM. It may be appreciated that the electronic circuitry 107 may include other arrangements and components.

Figure 11:
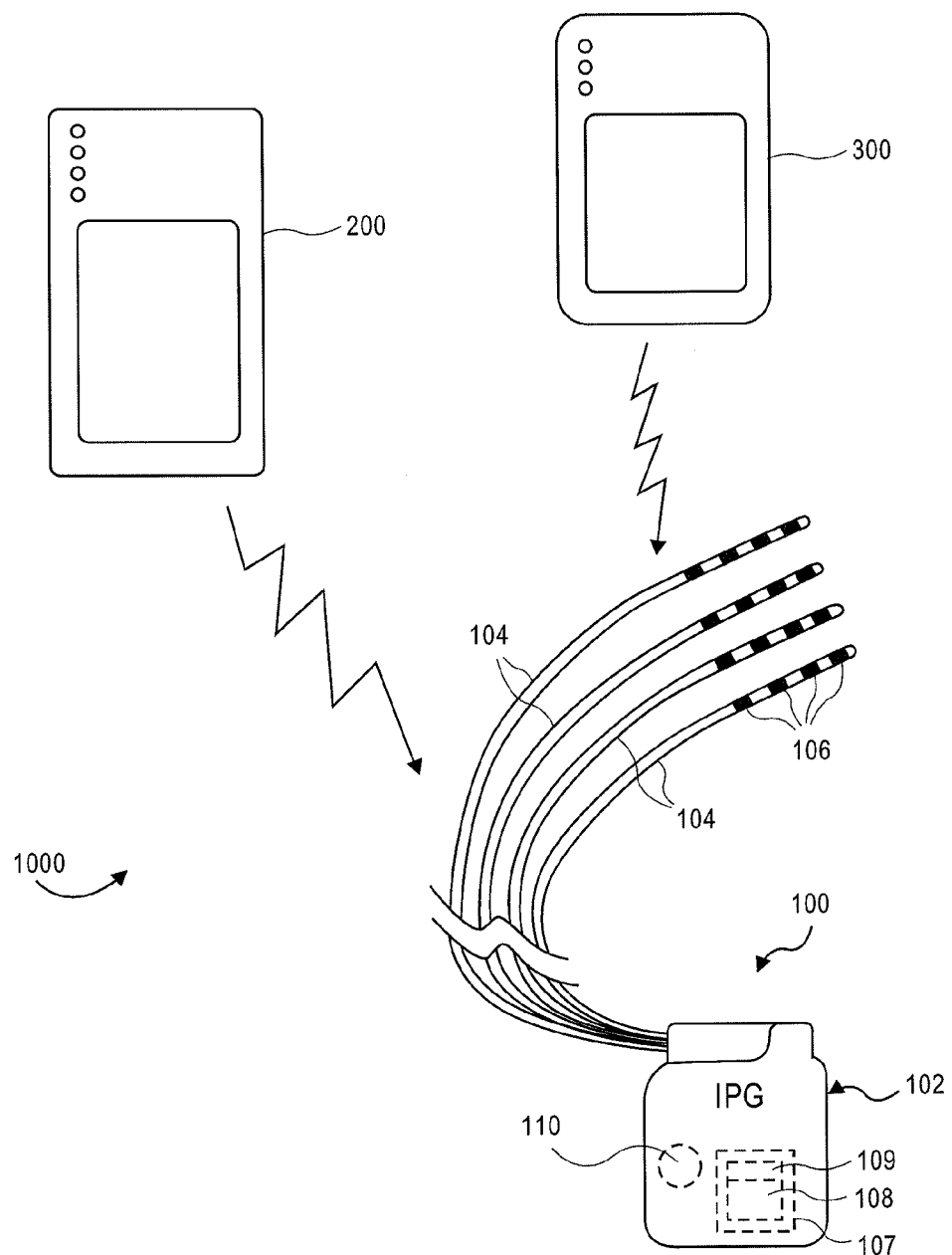
FIG. 11 illustrates at least one external programming device communicating with the IPG using telemetry.

Referring to FIG. 11, the IPG 102 is turned on and off and programmed to generate the desired stimulation pulses from at least one external programming device using telemetry, such as transcutaneous electromagnetic or RF links or a transmitting coil. In some embodiments, an RF link is used which complies with the MICS standard. This standard allocates a 402-405 MHz frequency spectrum intended for implantable medical devices. In other embodiments, the RF link utilizes a frequency of 400 MHz or greater. In still other embodiments, the RF link utilizes a frequency of 2.45 GHz. In some embodiments, telemetry is initiated by a magnet within or associated with the external programmer. The magnet actuates a magnetic sensor in the implanted IPG 102 when placed on the skin directly over the implant or within a suitable range of the implant. In addition, in some embodiments, the IPG 102 sniffs on all channels for communication attempts by external programmers. In some embodiments, such sniffing occurs over at predetermined intervals, such as every 10 min, and such intervals can be programmable. This is a backup communication link should the IPG fail to detect the magnet. Should the IPG detect the presence of an external programmer, the IPG typically responds to the programmer within thirty seconds, 15 seconds or less.

Figure 12:
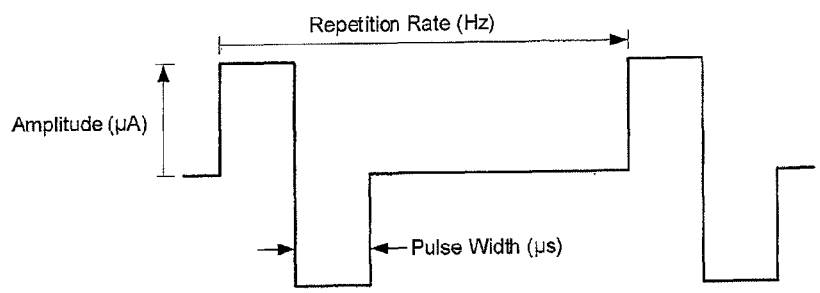
FIG. 12 illustrates an example of possible parameters of a stimulation signal which can be varied.

In some embodiments, the at least one external programming device comprises a clinical programmer 200 and a patient programmer 300. The clinical programmer 200 is used to program the stimulation information of the IPG 102, as determined by the clinician or investigator. The stimulation information includes signal parameters such as voltage, current, pulse width, repetition rate, and burst rates. FIG. 12 illustrates an example of possible parameters of a stimulation signal which may be varied. Using embodiments of the present invention, the amplitude, current, pulse width and repetition rate (also referred to as frequency) which provide the optimal therapeutic result can be determined. It may be appreciated that a constant current with a variable amplitude may be used, or a constant amplitude with a variable current may be used.

Referring back to FIG. 11, the patient programmer 300 allows the patient to adjust the stimulation settings of the IPG 102 within limits preset by the clinician. The patient programmer 300 also allows the patient to turn stimulation off, if necessary. The clinical and patient programmers 200, 300 are portable, hand-held devices that can be plugged into a power outlet or powered by an internal battery. The battery is typically rechargeable using a power supply and a power outlet. In some embodiments, the programmers 200, 300 contain an internal magnet to initiate communication with the IPG 102. The patient programmer 300 is designed to be easy to use and establishes two-way communication with the IPG 102 to control the stimulation. Together the implantable stimulation system 100, clinical programmer 200 and patient programmer 300 form a system 1000 which operates to provide personalized treatment for each patient, as will be described in more detail below.

Figure 13:
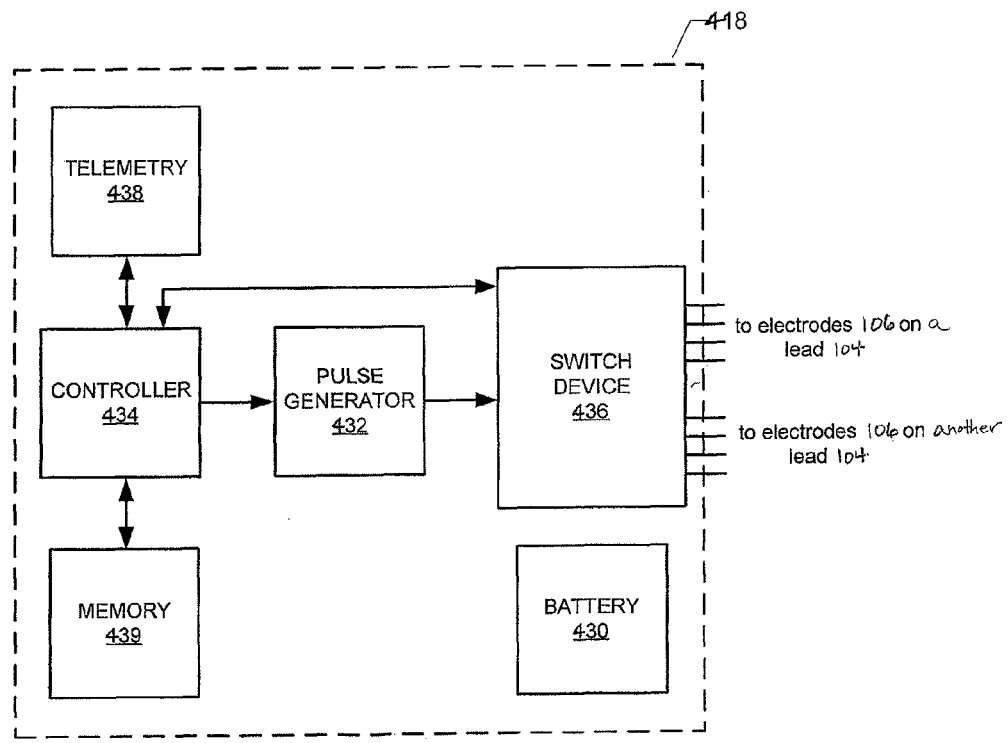
FIG. 13 is a simplified block diagram that illustrates possible components of the electronic circuitry of the IPG.

It may be appreciated that the embodiments of FIGS. 8, 9, 10, 11 are for illustrative purposes, wherein the components may vary. For example, FIG. 13 is a simplified block diagram that illustrates possible components of the electronic circuitry of the IPG. In this embodiment, the electronic circuitry 418 is shown as including a battery 430, pulse generator 432, a controller 434, a switch device 436, telemetry circuitry 438 and memory 439.

The battery 430 can be used to power the various other components of the electronic circuitry 418. Further, the battery 430 can be used to generate stimulation pulses. As such, the battery can be coupled to the pulse generator 432, the controller 434, the switch device 436, the telemetry circuitry 438 and the memory 439. A voltage regulator (not shown) can step up or step down a voltage provided by the battery 430 to produce one or more predetermined voltages useful for powering such components of the electronic circuitry 418. Additional electronic circuitry, such as capacitors, resistors, transistors, and the like, can be used to generate stimulation pulses, as is well known in the art.

The pulse generator 432 can be coupled to electrodes 106 of the lead(s) 104 via the switch device 436. The pulse generator 432 can be a single- or multi-channel pulse generator, and can be capable of delivering a single stimulation pulse or multiple stimulation pulses at a given time via a single electrode combination or multiple stimulation pulses at a given time via multiple electrode combinations. In one embodiment, the pulse generator 432 and the switch device 136 are configured to deliver stimulation pulses to multiple channels on a time-interleaved basis, in which case the switch device 436 time division multiplexes the output of pulse generator 432 across different electrode combinations at different times to deliver multiple programs or channels of stimulation energy to the patient.

The controller 434 can control the pulse generator 432 to generate stimulation pulses, and control the switch device 436 to couple the stimulation energy to selected electrodes. More specifically, the controller 434 can control the pulse generator 432 and the switch device 436 to deliver stimulation energy in accordance with parameters specified by one or more stimulation parameter sets stored within the memory 439. Exemplary programmable parameters that can be specified include the pulse amplitude, pulse width, and pulse rate (also known as repetition rate or frequency) for a stimulation waveform (also known as a stimulation signal). Additionally, the controller 434 can control the switch device 436 to select different electrode configurations for delivery of stimulation energy from the pulse generator 432. In other words, additional programmable parameters that can be specified include which electrodes 106 of which lead(s) 104 are to be used for delivering stimulation energy and the polarities of the selected electrodes 106. Each electrode 106 can be connected as an anode (having a positive polarity), a cathode (having a negative polarity), or a neutral electrode (in which case the electrode is not used for delivering stimulation energy, i.e., is inactive). A set of parameters can be referred to as a stimulation parameter set since they define the stimulation therapy to be delivered to a patient. One stimulation parameter set may be useful for treating a condition in one location of the body of the patient, while a second stimulation parameter set may be useful for treating a condition in a second location. It may be appreciated that each of the electrodes on an individual lead may provide a signal having the same signal parameters or one or more electrodes on the lead may provide a signal having differing signal parameters. Likewise, an individual electrode may provide a signal having differing signal parameters over time.

The controller 434 can include a microprocessor, a microcontroller, a digital signal processor (DSP), an application specific integrated circuit (ASIC), a field-programmable gate array (FPGA), a state machine, or similar discrete and/or integrated logic circuitry. The switch device 436 can include a switch array, switch matrix, multiplexer, and/or any other type of switching device suitable to selectively couple stimulation energy to selected electrodes. The memory 439 can include RAM, ROM, NVRAM, EEPROM or flash memory, but is not limited thereto. Various programs and/or stimulation parameter sets can be stored in the memory 439, examples of which are discussed herein.

Once a desired stimulation parameter set is determined, the IPG 102 can be programmed with the optimal parameters of the set. The appropriate electrode(s) 106 on the lead 104 then stimulate the nerve tissue with the determined stimulation signal.

Figure 14:
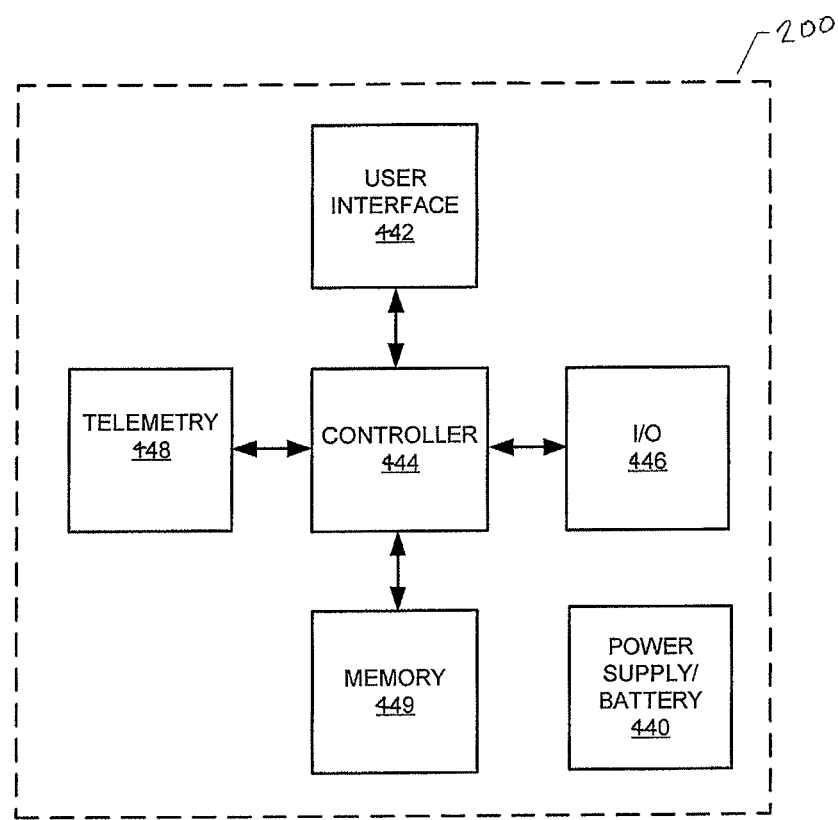
FIG. 14 is a simplified block diagram that illustrates possible components of an external programmer, such as a clinical programmer.

FIG. 14 is a simplified block diagram that illustrates possible components of an external programmer, such as a clinical programmer 200. Referring to FIG. 14, the clinical programmer 200 is shown as including a power supply 440, a user interface 442, a controller 444, input and output (I/O) circuitry 446, telemetry circuitry 448 and memory 449.

The power supply 440, which can include a battery, can be used to power the various other components of the external programmer. As such, the power supply 440 can be coupled to the user interface 442, the controller 444, the input and output (I/O) circuitry 446, the telemetry circuitry 448 and the memory 449. A voltage regulator (not shown) can step up or step down a voltage provided by a battery or an external power source to produce one or more predetermined voltages useful for powering such components of the external programmer.

The clinician or other operator may utilize the clinical programmer 200 to perform a variety of functions. For example, in some embodiments the clinical programmer 200 can be used to:

Turn OFF all stimulation.

Turn stimulation ON for up to four leads and measure lead impedance.

Assign body regions, electrode configurations and stimulation settings for each lead.

Enter patient and lead identification information, clinician and clinic name and contact information, and clinician's notes.

Perform a real time test to assess the patient stimulation response for each lead.

Enable Patient Controlled Therapy and configure Patient Controlled Therapy settings for each lead.

Acquire identification, diagnostic, and historic information about the IPG 102.

Program configured therapy settings, and patient and clinician information into the IPG 102 device.

The clinician may interact with the controller 444 via the user interface 442 in order to test various stimulation parameter sets, input user feedback, select preferred or optimal programs, and the like. The user interface 442 can include a display, a keypad, a touch screen, one or more peripheral pointing devices (e.g., a mouse, touchpad, joystick, trackball, etc.), and the like. The controller 444 can provide a graphical user interface (GUI) via the user interface 442 to facilitate interaction with the clinician. The controller 444 can include a microprocessor, a microcontroller, a digital signal processor (DSP), an application specific integrated circuit (ASIC), a field-programmable gate array (FPGA), a state machine, or similar discrete and/or integrated logic circuitry. The I/O circuitry 446 can include transceivers for wireless communication, ports for wired communication and/or communication via removable electrical media, and/or appropriate drives for communication via removable magnetic or optical media. The telemetry circuitry 448 can be the telemetry circuitry described above, or separate but similar telemetry circuitry.

Figure 15A:
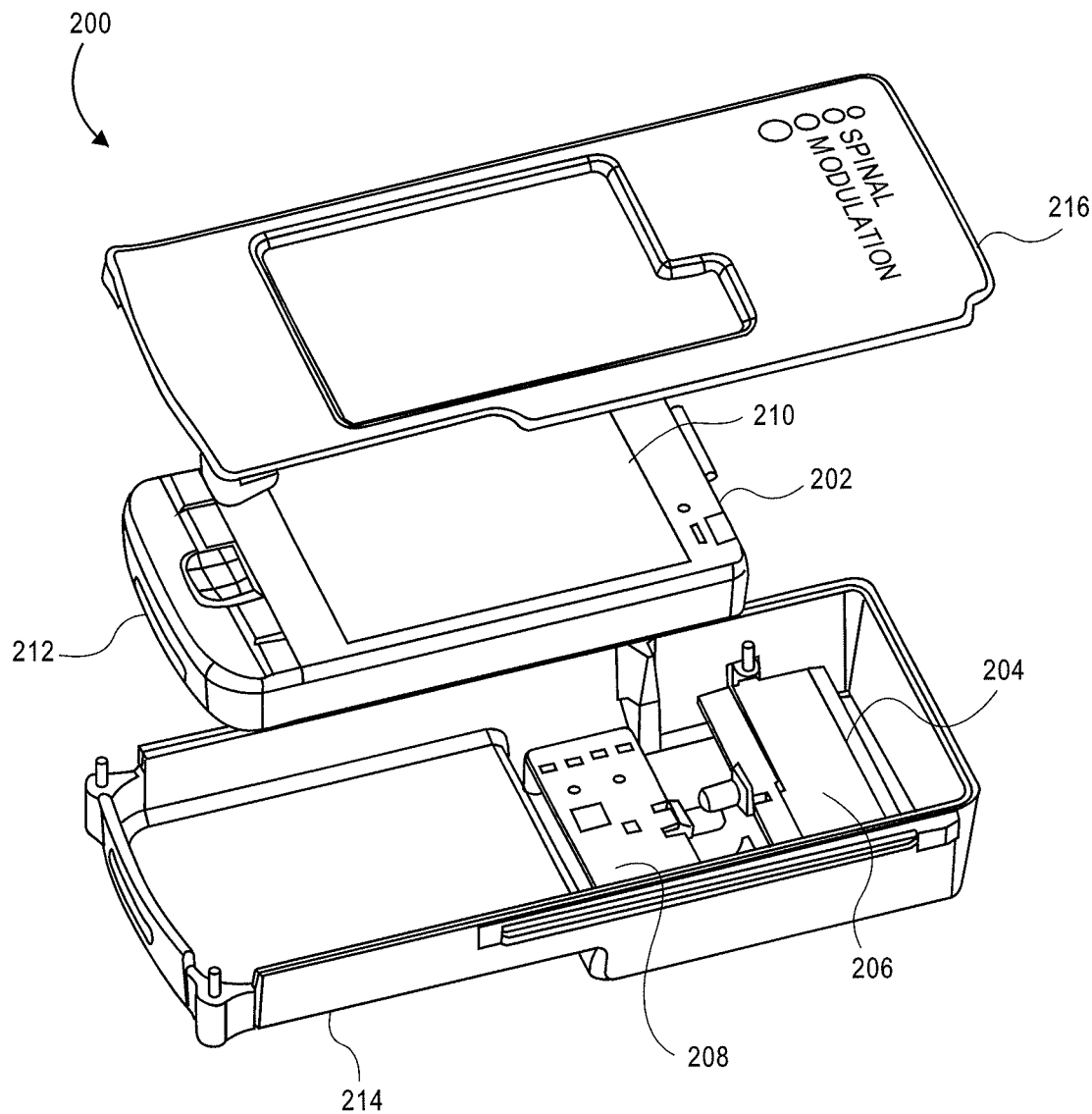
FIG. 15A provides a perspective expanded view of an embodiment of a clinical programmer.

FIG. 15A provides a perspective expanded view of an embodiment of a clinical programmer 200. In this embodiment, the clinical programmer 200 comprises a handheld computer 202, such as a personal digital assistant, an antenna 204, a ground plane 206, and a telemetry controller 208 or "Base Station" (micro) plus RF board. As shown, the handheld computer 202 includes a touch screen user interface 210 and an input and output (I/O) port 212. In this embodiment, these components are disposed within a housing comprising a cradle 214 and a faceplate 216, as shown.

Referring back to FIG. 14, the controller 444 can collect information relating to tested electrode parameters (e.g., combinations) and stimulation signal parameters, and store the information in the memory 449 for later retrieval and review by a clinician or by the controller 444 to facilitate identification of one or more preferred stimulation parameter sets. The controller 444 can send instructions to the IPG 102 via the telemetry circuit 448 to cause the testing of various stimulation parameter sets. For example, the controller 444 can effectuate the testing of stimulation parameter sets created by the controller 444 or clinician to the IPG 102.

The memory 449 can include program instructions that, when executed by the controller 444, cause the programmer 422 to perform at least some of the functions described herein. For example, the controller 444 can execute program instructions that specify protocols for testing various stimulation parameter sets and selecting one or more preferred stimulation parameter sets. The memory 449 can also store one or more stimulation parameter sets determined to treat a particular condition of a patient, along with information about the patient. The memory 449 can include any volatile, non-volatile, fixed, removable, magnetic, optical, or electrical media, such as a RAM, ROM, CD-ROM, hard disk, removable magnetic disk, memory cards or sticks, NVRAM, EEPROM, flash memory, and the like.

Figure 15B:
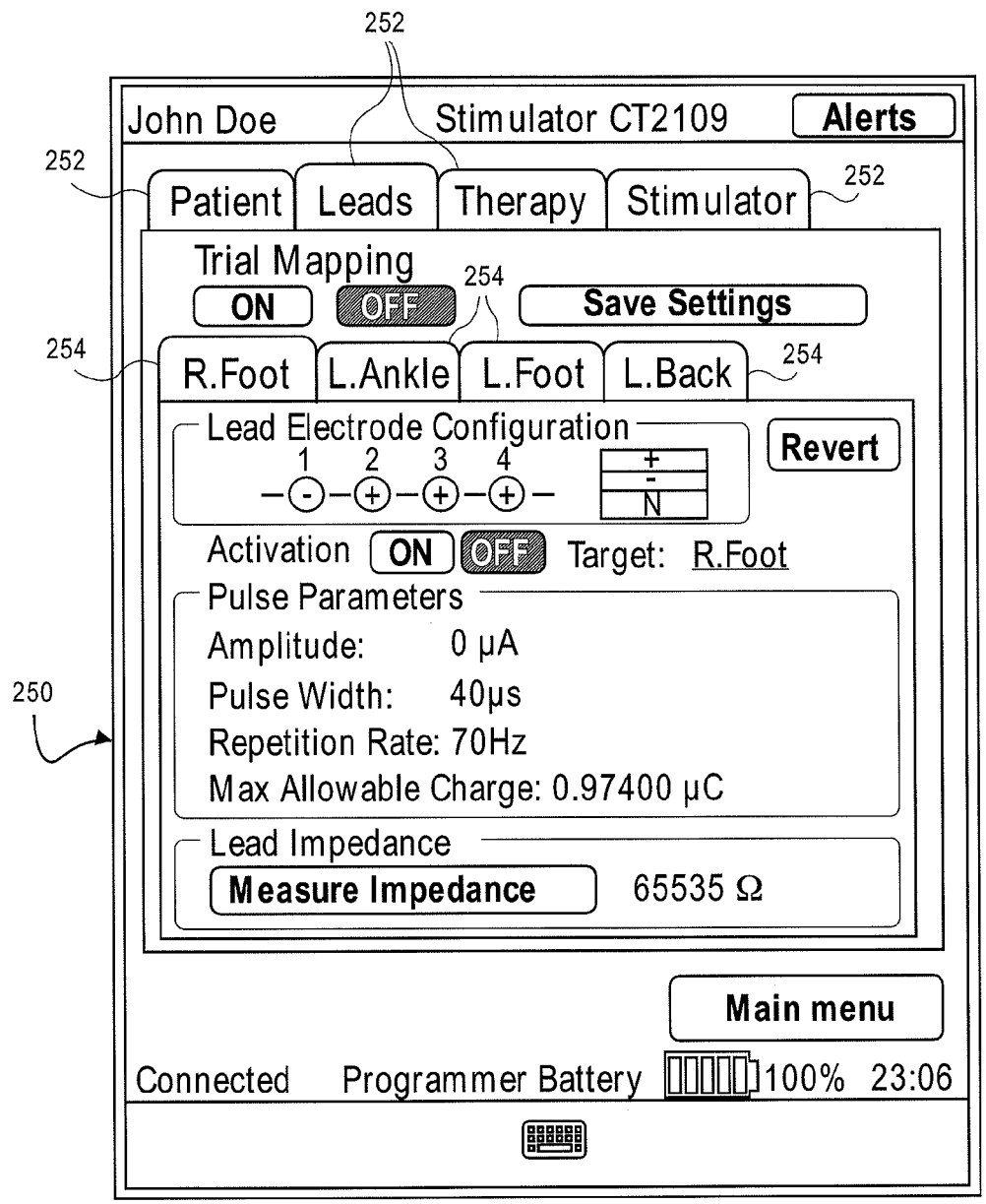
FIG. 15B and FIG. 15C illustrate embodiments of screenshots of a clinical programmer.

In some embodiments, the clinical programmer 200 includes "workspaces" which are used to view and program the therapy settings and to obtain diagnostic information. A record of the programmed settings and diagnostic information is generated after every session. In some embodiments, four workspaces are provided: "Patient", "Leads", "Therapy" and "Stimulator". FIG. 15B provides an example screenshot 250 of the clinical programmer 200. The four workspaces are shown as workspace tabs 252 near the top of the screenshot 250.

In some embodiments, the Patient Workspace is used to: Enter patient identification information; Enter IPG device information; Enter clinician, clinic name and contact information; and Enter clinician's notes. In some embodiments, the Patient Workspace is divided into three tabs: "Patient Information", "Clinician", and "Notes". Under the Patient Information tab, information may be entered such as one or more of the following: Patient Name, Date of Birth, Patient Address, Patient ID Number, Stimulator Serial Number, Date of Implant, Lead Serial Numbers. Under the Clinician tab, information may be entered such as one or more of the following: Physician Name, Clinic Name, Clinic Address, Clinic Phone Number, Clinic Email Address. Under the Notes tab, a text field is provided to enter free text notes. Optionally, any previous information that has been entered in the text field will be erased when the text field is updated.

In some embodiments, the Leads Workspace is used to: Activate (turn on) up to four leads; Adjust electrode configuration; Measure impedance; Set nominal values to begin stimulation; Perform trial mapping; Confirm and assign specific body regions to be stimulated. There is one Lead tab for each lead, each Lead tab may be labeled with the corresponding body region receiving stimulation. Each body region can have stimulation adjusted as described herein. FIG. 15B illustrates four body region tabs 254, one each for right foot, left ankle, left foot, and lower back. As mentioned, in some embodiments each lead has four electrodes. Each of the electrodes can be programmed with a positive or negative pulse, or be programmed as neutral (off). For each lead, the pulse parameters are also programmable. Typically, the pulse parameters include: Pulse Amplitude (µA), Pulse Width (µs), Pulse Repetition Rate (Hz), and Allowed Impedance Range (Ω). The Allowed Impedance Range is dependent on voltage and amplitude combinations. In some embodiments, each pulse parameter is selected from a drop-down table. The parameter choices are specific to a variety of factors, including the anatomical target, and will be described in later sections below.

Typically, each lead has a Maximum Allowable Charge. The calculated value of the maximum allowable charge delivered by each lead may be displayed under its associated Lead tab. This value is calculated based on the assigned pulse parameter settings and the lead's electrode configuration. Thus, combinations of amplitude and pulse width selections are typically limited by the maximum allowable charge. Therefore, for certain amplitude settings, only certain pulse width settings may be selectable. Similarly, for certain pulse width settings, only certain amplitude settings may be selectable.

In some embodiments, a Measure Impedance Button is included. The Measure Impedance Button is activated to measure the lead's impedance. Once activated, the impedance value may be displayed.

Figure 15C:
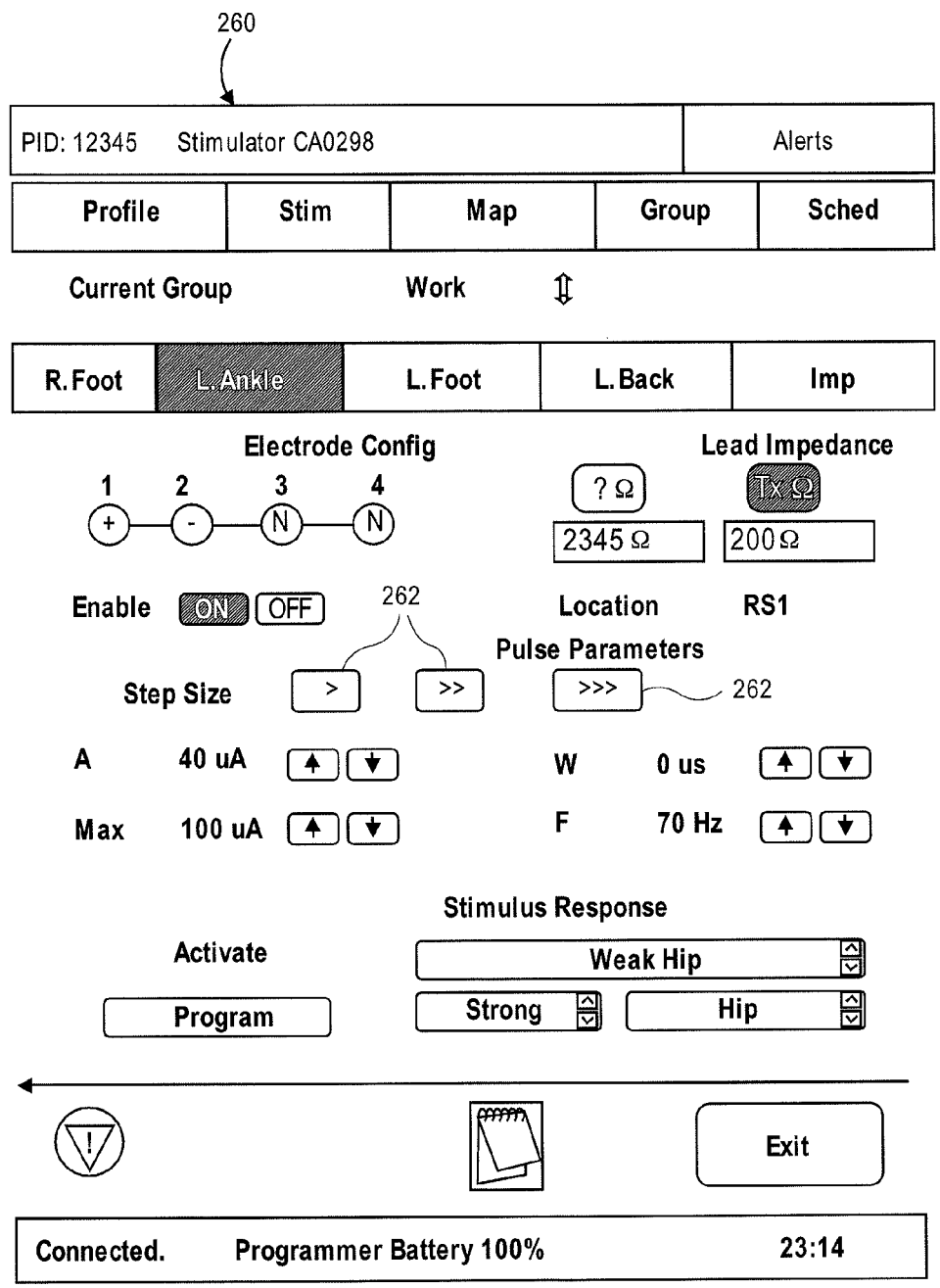

In some embodiments, the clinical programmer 200 is used for Trial Mapping. Trial Mapping allows the clinician to test and confirm patient stimulation response for each lead target or body region in real time. Typically, Trial Mapping starts with the use of signal parameters set to relatively low settings. Parameter settings are increased or decreased by pressing the "Up" or "Down" arrow button respectively. FIG. 15C illustrates an embodiment of a screenshot 260 showing a selectable step size buttons 262 when changing parameter settings. As will be described in later sections, since the parameter values for the system 100 are lower than conventional stimulation systems, the granularity of control or step size is also smaller. Thus, smaller increments are needed to cycle through the signal parameter values to determine the appropriate combination of values to treat the condition. However, the clinician may desire a variety of step sizes to narrow the range of parameter values. For example, the clinician may start with a larger step size (>>>) for gross changes in parameters values and then move to a smaller step size (>>) and even smaller step size (>) when approaching the desired parameter value. Each enabled lead pulse parameter setting is adjusted until a desired response is achieved. The actual step sizes corresponding to the selectable step size buttons 262 are preprogrammed into the programmer 200. It may be appreciated that as the clinician scrolls through different ranges of the parameter values, the step size will automatically change to a granularity appropriate for the range. The settings are then saved to memory in preparation for programming of the IPG. The Trial Mapping process is then repeated for each activated body region.

In some embodiments, the Therapy workspace is used to: Enable or disable patient controlled therapy for each lead; and Set maximum current amplitude accessible for adjustment by the patient. Selecting "ON" enables Patient Controlled therapy. This allows the patient to adjust therapy settings using their Patient Programmer. Selecting "OFF" disables and blocks patient access to Patient Controlled therapy. When setting Maximum Stimulation Amplitude Settings, the clinician typically enters the maximum stimulation amplitude from a clinically set amplitude, such as up to 4.0 mA, that the patient is allowed to set for each lead.

In some embodiments, the Stimulator Workspace is used to: Acquire identification, diagnostic, and historic information about the IPG; Program the IPG with therapy settings; and Program patient and clinician information. In some embodiments, the Stimulator Workspace has two tabs, "Information" and "Program". When the "Information" tab is selected, the screen displayed is read only and may display one or more of the following: Neurostimulator Serial Number (displays the serial number for the IPG); NS Firmware Version (displays the Stimulator firmware version); Lead Serial Numbers (Displays each lead's serial number; Neurostimulator Clock Information (displays the time when the IPG was first queried for that specific therapy session); and Implant Battery Information.

The "Program" tab is used to program the IPG with the configured settings including Leads settings and Patient Controlled therapy settings. In some embodiments, Patient and Stimulator Identification Information is displayed under the "Program" tab. Such information may include Patient Name; Patient Date of Birth; Stimulator Serial Number; and Stimulation Therapy Summary Table. The Stimulation Therapy Summary Table, also referred to as "Stimulator Settings", displays configured stimulation therapy settings. In some embodiments, there are three columns: the first lists the parameter names; the second lists the retained values in the Clinical Programmer; the third lists the programmed values in the IPG. Optionally, stimulation therapy parameters may be highlighted, such as using red text, to indicate parameters that have been modified since the last stimulation therapy was programmed to the IPG. Data may be presented in this order: Patient, Leads, and Therapy. Use of the vertical scroll bar may be used to display the different parameters.

Additionally, in some embodiments, a "Program Stimulator" button is provided under the "Program" tab. The "Program Stimulator" button is used to transfer the programmed values to the IPG. A table below the "Program Stimulator" button displays a summary of the configured stimulation therapy settings. A confirmation window may be displayed to confirm whether it is desired to program the IPG. Selecting a "Yes" button programs the settings displayed. Selecting a "No" button cancels programming the IPG.

Typically, the patient programmer 300 that is to be used by the patient is specifically bound to the patient's IPG in order for the patient to be able to minimally adjust the stimulation settings. Likewise, the patient programmer 300 may be bound to multiple IPGs within a patient if the patient has been implanted with more than one IPG.

Figure 16:
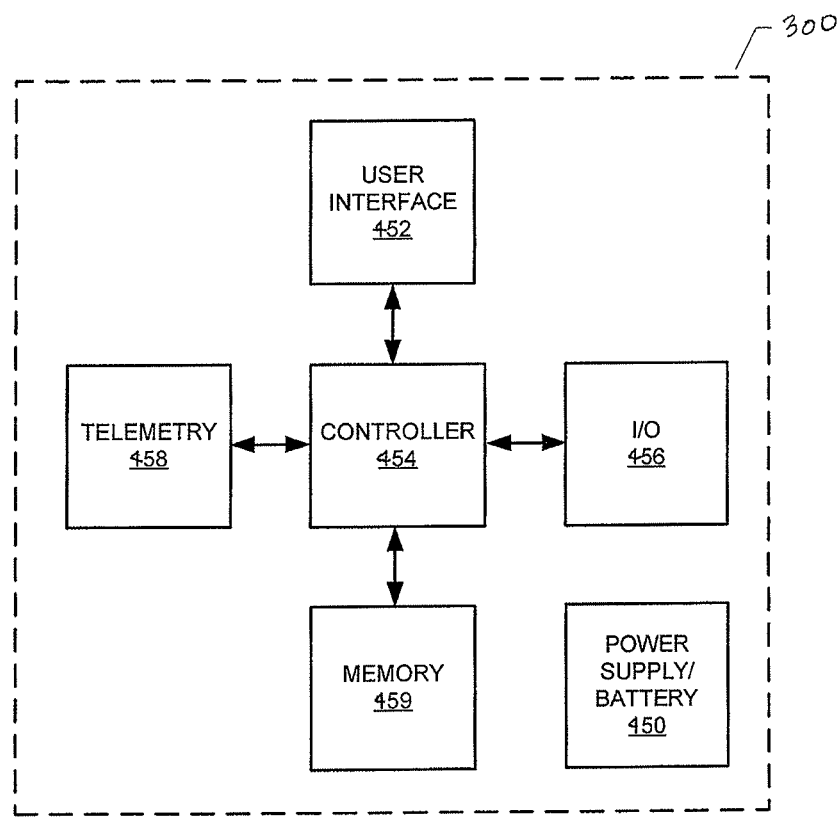
FIG. 16 is a simplified block diagram that illustrates possible components of another external programmer, such as a patient programmer.

FIG. 16 is a simplified block diagram that illustrates possible components of an external programmer, such as a patient programmer 300. Referring to FIG. 16, the patient programmer 300 is shown as including a power supply 450, a user interface 452, a controller 454, input and output (I/O) circuitry 456, telemetry circuitry 458 and memory 459. The power supply 450, which can include a battery, can be used to power the various other components of the patient programmer 300. As such, the power supply 450 can be coupled to the user interface 452, the controller 454, the input and output (I/O) circuitry 456, the telemetry circuitry 458 and the memory 459. A voltage regulator (not shown) can step up or step down a voltage provided by a battery or an external power source to produce one or more predetermined voltages useful for powering such components of the patient programmer 300.

A patient can interact with the controller 454 via the user interface 452 in order to select, modify or otherwise control delivery of stimulation therapy. For example, the patient may be able to select among various stimulation parameter sets that are stored in the memory 459. Additionally, or alternatively, the patient may be able to increase or decrease specific stimulation signal parameters, such as amplitude, to tailor the therapy to the symptoms being experienced at the time. The user interface 442 can include a display, a keypad, a touch screen, one or more peripheral pointing devices (e.g., a mouse, touchpad, joystick, trackball, etc.), and the like. The controller 454 can provide a graphical user interface (GUI) via the user interface 452 to facilitate interaction with a patient. The controller 454 can include a microprocessor, a microcontroller, a digital signal processor (DSP), an application specific integrated circuit (ASIC), a field-programmable gate array (FPGA), a state machine, or similar discrete and/or integrated logic circuitry. The I/O circuitry 446 can include transceivers for wireless communication, ports for wired communication and/or communication via removable electrical media, and/or appropriate drives for communication via removable magnetic or optical media.

In some embodiments, the memory 459 can store data related to stimulation parameter sets that are available to be selected by the patient for delivery of stimulation therapy to the patient using the IPG 102 implanted within the patient. In some embodiments, the controller 454 can record usage information and store usage information in the memory 459. The memory 459 can include program instructions that, when executed by the controller 454, cause the patient programmer 426 to perform functions ascribed to the patient programmer 300. The memory 459 can include any volatile, non-volatile, fixed, removable, magnetic, optical, or electrical media, such as a RAM, ROM, CD-ROM, hard disk, removable magnetic disk, memory cards or sticks, NVRAM, EEPROM, flash memory, and the like. Memory in IPG can record impedance data, current, voltage, time of day, time of therapy changes, built in circuit testing, battery data, to name a few. Upon connection with an external programmer, the programmer can record the IPG recorded data. This data can then be used to reprogram the IPG.

The telemetry circuitry 458 allows the controller to communicate with IPG 102, and the input/output circuitry 456 may allow the controller 454 to communicate with the clinician external programmer 200. The controller 454 can receive selections of, or adjustments to, stimulation parameter sets made by the patient via the user interface 452, and can transmit the selection or adjustment to the IPG 102 via telemetry circuitry 458. Where the patient programmer 300 stores data relating to stimulation parameter sets in the memory 459, the controller 454 can receive such data from the clinician programmer 200 via the input/output circuitry 456 during programming by a clinician or physician. Further, the patient programmer 300 can transmit data relating to stimulation parameter sets to the IPG 102 via the telemetry circuitry 458.

The patient may utilize the patient programmer 300 to perform a variety of functions. For example, in some embodiments the patient programmer 300 can be used to:

Turn OFF all stimulation, if desired.

Turn stimulation ON or OFF for each body region to be stimulated.

Adjust the amount of stimulation for each body region.

View the IPG identification information including the stimulator serial number, each lead's serial number, and the date when the IPG was last programmed.

View the patient's name (optionally, the study ID number).

View the lead placement date.

View the clinician name, clinic name and contact information.

Typically, the patient programmer 300 includes a Main Menu which displays two main functions: Adjust Stimulation Settings and Programmer Setup. The Adjust Stimulation Settings allows the user to set up communication with the IPG and adjust stimulation settings. The Programmer Setup allows the patient to set the Patient Programmer date and time, and to view information about the IPG and Patient Programmer controls. Often the Main Menu has some basic information identifying the device. In addition, the physician, clinic and the clinic phone number are typically displayed, along with the Programmer Serial Number, Software Version and Base Station Firmware Version. Further, the Main Menu may include the IPG connection status, the battery charge level and the time.

In some embodiments, the patient can cause the IPG to check for communication from the patient programmer 300 with the use of a magnet within or associated with the patient programmer 300. The patient may place the magnet near the IPG, such as within 6 feet, for a period of time, such as 5 seconds or more.

When four leads are implanted and programmed by the clinician for use, the patient can turn stimulation therapy ON or OFF for up to four areas of the body and adjust the amount of stimulation any of those areas are receiving as allowed by the clinical programmer. It may be appreciated that such functionality applies to any number of leads which are implanted and programmed for use. To turn stimulation therapy ON or OFF, the Patient Programmer 300 may display the names of one to four designated body regions that the leads have been placed to stimulate and the patient individually turns stimulation of each region on or off.

In some embodiments, when stimulation is ON, the patient may adjust the amount of stimulation to the body region. For example, once the correct tab has been selected for the specific body region to be adjusted, the patient may press the "Down" button to decrease the stimulation level or press the "Up" button to increase the stimulation level. In some embodiments, a stimulation level indicator between the "Up" and "Down" buttons moves up or down as the patient changes the stimulation level for the selected body region. Further, the stimulation level indicator may also show the current stimulation level and where it is compared to the maximum set by the clinician. The adjustments may then be saved and the patient can continue to adjust stimulation to other specific body regions.

Figure 17:
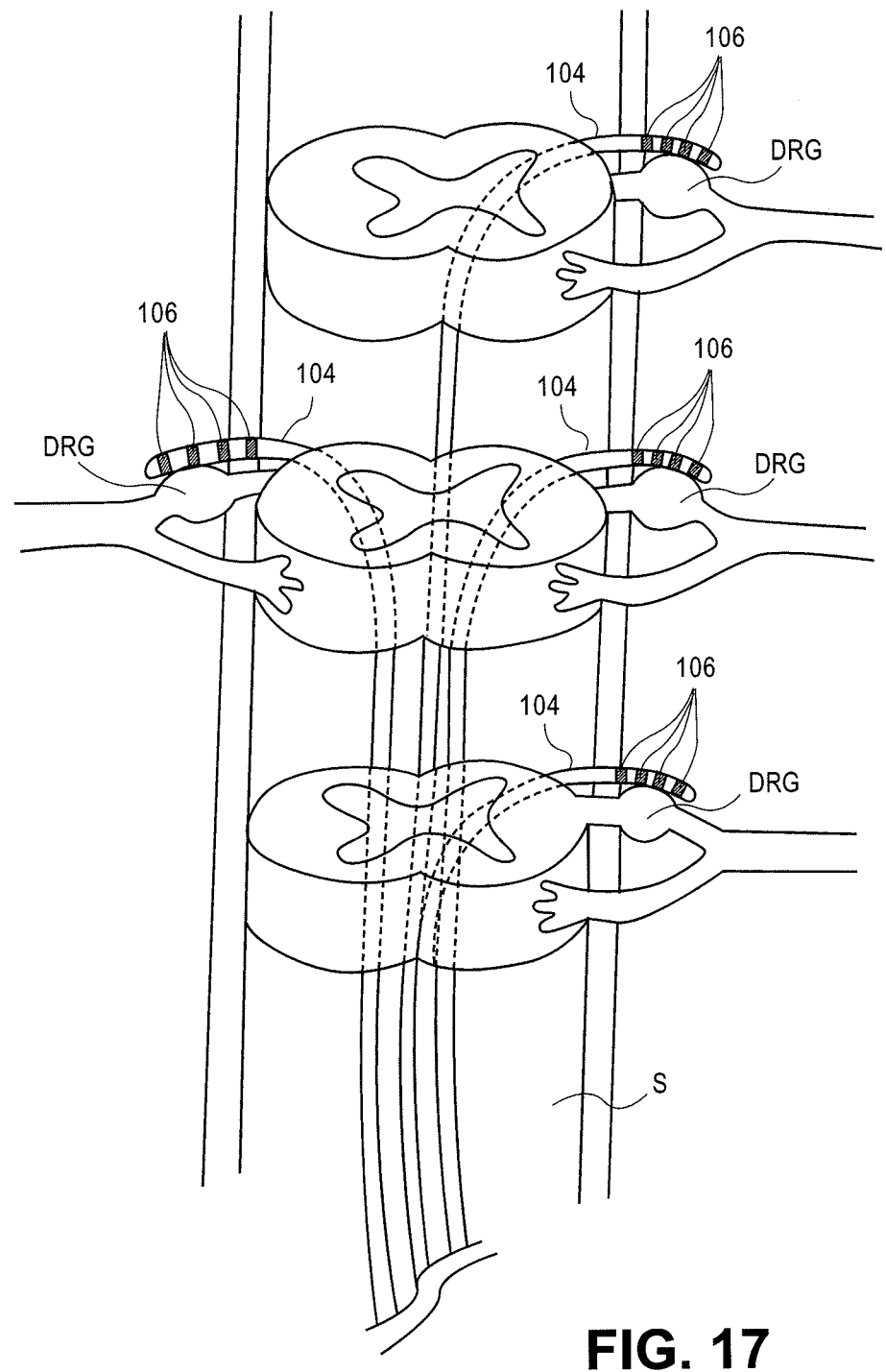
FIG. 17 illustrates example placement of the leads of the embodiment of FIG. 7 within the patient anatomy.

The above described implantable stimulation system 100 can be used to stimulate a variety of anatomical locations within a patient's body. In preferred embodiments, the system 100 is used to stimulate one or more dorsal roots, particularly one or more dorsal root ganglions. FIG. 17 illustrates example placement of the leads 104 of the embodiment of FIG. 7 within the patient anatomy. In this example, each lead 104 is individually advanced within the spinal column S in an antegrade direction. Each lead 104 has a distal end which is guidable toward a target DRG and positionable so that its electrodes 106 are in proximity to the target DRG. Specifically, each lead 104 is positionable so that its electrodes 106 are able to selectively stimulate the DRG, either due to position, electrode configuration, electrode shape, electric field shape, stimulation signal parameters or a combination of these as will be discussed in more detail in a later section. FIG. 17 illustrates the stimulation of four DRGs, each DRG stimulated by one lead 104. These four DRGs are located on three levels, wherein two DRGs are stimulated on the same level. It may be appreciated that number of DRGs and any combination of DRGs may be stimulated with the stimulation system 100 of the present invention. It may also be appreciated that more than one lead 104 may be positioned so as to stimulate an individual DRG and one lead 104 may be positioned so as to stimulate more than one DRG.

Figure 18:
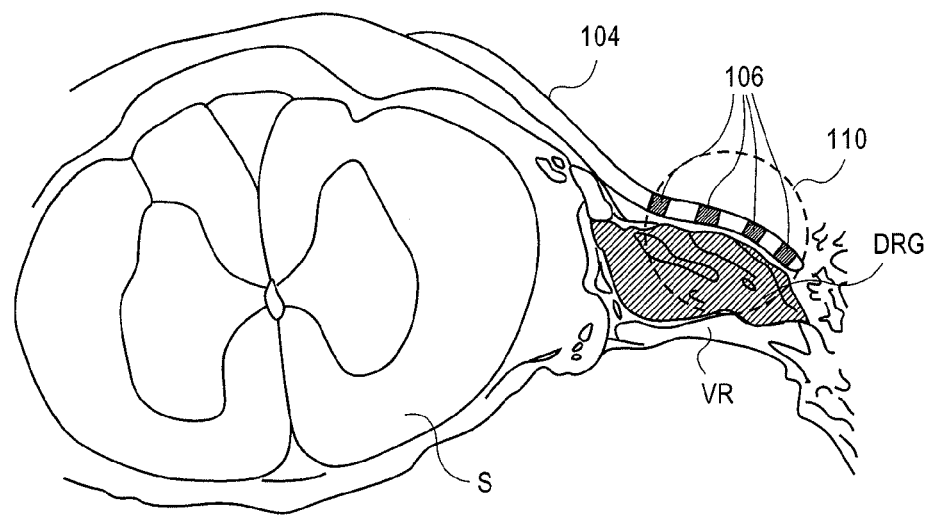
FIG. 18 illustrates a cross-sectional view of an individual spinal level showing a lead of the stimulation system positioned near a target DRG.

FIG. 18 illustrates an example cross-sectional view of an individual spinal level showing a lead 104 of the stimulation system 100 positioned on, near or about a target DRG. The lead 104 is advanced along the spinal cord S to the appropriate spinal level wherein the lead 104 is advanced laterally toward the target DRG. In some instances, the lead 104 is advanced through or partially through a foramen. At least one, some or all of the electrodes 106 are positioned on, about or in proximity to the DRG. In preferred embodiments, the lead 104 is positioned so that the electrodes 106 are disposed along a surface of the DRG opposite to the ventral root VR, as illustrated in FIG. 18. It may be appreciated that the surface of the DRG opposite the ventral root VR may be diametrically opposed to portions of the ventral root VR but is not so limited. Such a surface may reside along a variety of areas of the DRG which are separated from the ventral root VR by a distance.

In some instances, such electrodes 106 may provide a stimulation region indicated by dashed line 110, wherein the DRG receives stimulation energy within the stimulation region and the ventral root VR does not as it is outside of the stimulation region. Thus, such placement of the lead 104 may assist in reducing any possible stimulation of the ventral root VR due to distance. However, it may be appreciated that the electrodes 106 may be positioned in a variety of locations in relation to the DRG and may selectively stimulate the DRG due to factors other than or in addition to distance, such as due to stimulation profile shape and stimulation signal parameters, to name a few. It may also be appreciated that the target DRG may be approached by other methods, such as a retrograde epidural approach. Likewise, the DRG may be approached from outside of the spinal column wherein the lead 104 is advanced from a peripheral direction toward the spinal column, optionally passes through or partially through a foramen and is implanted so that at least some of the electrodes 106 are positioned on, about or in proximity to the DRG.

In order to position the lead 104 in such close proximity to the DRG, the lead 104 is appropriately sized and configured to maneuver through the anatomy. Such maneuvering includes atraumatic epidural advancement along the spinal cord S, through a sharp curve toward a DRG, and optionally through a foramen wherein the distal end of the lead 104 is configured to then reside in close proximity to a small target such as the DRG. Consequently, the lead 104 is significantly smaller and more easily maneuverable than conventional spinal cord stimulator leads. Example leads and delivery systems for delivering the leads to a target such as the DRG are provided in U.S. Provisional Patent Application No. 61/144, 690, filed Jan. 14, 2009 entitled "STIMULATION LEAD, DELIVERY SYSTEM AND METHODS OF USE" by Fred I. Linker et al. and is incorporated herein by reference for all purposes.

In addition, by positioning the electrodes 106 in close proximity to the target tissue, less energy is required for stimulation. This reduction in energy allows a reduction in electrode size, among other benefits. In some embodiments, the average electrode surface area is approximately 1-6 mm$^2$, particularly approximately 2-4 mm$^2$, more particularly 3.93 mm$^2$ whereas conventional spinal cord stimulators typically have a much larger average electrode surface area, such as 7.5 mm$^2$ for some leads or 12.7 mm$^2$ for traditional paddle leads. Likewise, in some embodiments an average electrode length is 1.25 mm whereas conventional spinal cord stimulators typically have an average electrode length of 3 mm. Such reduced electrode sizing allows more intimate positioning of the electrodes in the vicinity of the DRG and allows for IPGs having different control and performance parameters for providing direct and selective stimulation of a targeted neural tissue, particularly the DRG. In addition, in some embodiments, the overall dimensions of one or more electrodes and the spacing of the electrodes is selected to match or nearly match the overall dimensions or size of the stimulation target. In an embodiment where the targeted neural tissue is a substantial portion of a dorsal root ganglion, the electrode or electrodes arrayed along the lead are sized and spaced so that a majority of the electrodes lie along the overall dimensions of the dorsal root ganglion. For example, if there are 4 electrodes on a lead to stimulate a dorsal root ganglion having a length of about 8 mm, then the overall length of the electrode portion of the lead should be between about 6-10 mm. FIG. 18 illustrates one example where all 4 of the electrodes on the lead are within the lateral dimension of the DRG as shown. The size and spacing of the electrodes may align with other DRG dimensions as well. In one specific aspect, the spacing of the electrodes is such that when placed near the targeted dorsal root ganglion two or more electrodes are in position to provide therapeutic energy to the targeted dorsal root ganglion. Since the size of the ganglion depends on the spinal level and other factors, a variety of different electrode sizes and spacing may be used to tailor the electrode portion to selected dorsal root ganglia. It may also be appreciated that in some embodiments, the electrodes 106 are directional so as to provide direct and selective stimulation and further decrease energy required for stimulation.

In some embodiments, the electrodes 106 are spaced 5 mm apart along the distal end of the lead 104. In other embodiments, the electrodes 106 are spaced 0.250 inches apart, from center to center, and 0.200 inches apart, from inside edge to inside edge. In most patients, the DRG has a size of 5-10 mm. Therefore, typical spacing would allow two electrodes 106 to be in contact with the target DRG while the remaining two electrodes are in the vicinity of the target DRG. In some instances, the two electrodes 106 in contact with the DRG are used to stimulate the DRG while the remaining two electrodes 106 do not provide stimulation energy. In other instances, all four electrodes 106 provide stimulation energy to the DRG, two electrodes providing energy to the DRG at a distance somewhat closer to the DRG than the other two electrodes. It may be appreciated that any combination of electrodes 106 may provide stimulation energy and each electrode 106 may provide a different level or type of stimulation signal. Consequently, a variety of electric field shapes may be generated, each shape potentially causing a different treatment effect. In many embodiments, the electric field shape will be elliptical. Likewise, the position of the electric field in relation to the anatomy may also be adjusted to potentially cause different treatment effects. Such effects will be described in greater detail below. It may also be appreciated that the electrodes 106 providing stimulation energy may change over time. For example, if a lead 104 has migrated, a different combination of electrodes 106 may be used to stimulate the target DRG in the new lead position.

As mentioned above, the intimate positioning of the leads 104 of the present invention allows the stimulation system 100 to have a variety of additional beneficial features. For example, positioning the leads 104 in such close proximity to the target tissue allows for smaller stimulation regions. This in turn allows for smaller electrode surface areas and reduced energy requirements. A reduction in energy requirements allows for smaller battery size, increased battery longevity and the possibility of the elimination of battery replacement or recharging altogether. Typically, patients with conventional systems either have an IPG with a standard battery wherein the IPG is surgically replaced when the battery wears out or they have an IPG with a rechargeable battery wherein the battery is recharged by an external device worn for a few hours every two or three weeks. In contrast, the system 100 of the present invention draws such low energy that the battery longevity is sufficient for the life of the device. Thus, the patient will not need to undergo additional surgeries to replace the battery, therefore reducing any risks of surgical complications. The patient will also not need to recharge the battery which increases quality of life and provides for more continuous therapy. In both cases, less clinical follow-up may be necessary which reduces costs and increases patient satisfaction. However, it may be appreciated that rechargeable batteries may be used.

The energy requirement for the stimulation system 100 of the present invention is exceptionally low, particularly in comparison to conventional spinal cord stimulation systems. Energy is the work done in moving an electric charge (q) between two points with a potential difference (v) between them. Recall that if (q) is the electric charge, which varies with time (t), then the resulting current is given by i=dq/dt. The unit of current is the ampere. Power is the rate in which work is done. Consider a charge (dq) moving from point A to point B in a time interval (dt) and let the potential difference between A and B be (v). Then the work done on the charge (dq) is $$dw=vdq=v(idt)$$

Then the power is given by $$p=dw/dt=vi$$

The unit of power is the watt. One watt equals 1 joule/second. As mentioned, energy is the work done in moving an electric charge (q) between two points with a potential difference between them. Since power equals the derivative of energy, energy equals the integral of power. The energy delivered or received by a component at time (t) is therefore given by $$w(t)=\int p(t)dt$$

The unit of energy is joules. The movement of electric charge (q) between these two points depends on the resistance R.

$$R=v(t)/i(t)$$

A unit of resistance is the ohm ($\Omega$). Therefore, one ohm equals 1 volt/amp. And, therefore:

$$p(t)=R[i(t)]^2$$

Thus, energy delivered or received by a component at a time (t) is also related to resistance.

Figure 19A:
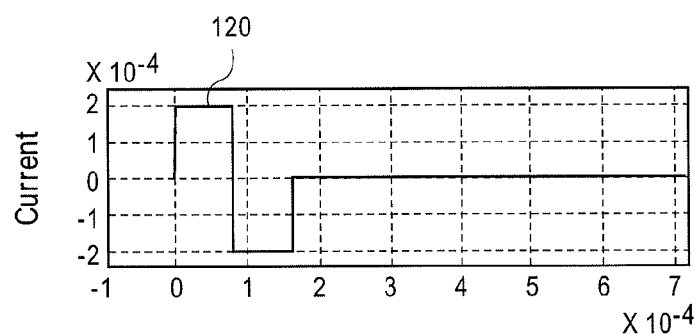
FIG. 19A illustrates an embodiment of a trace representing a stimulation signal of the present invention and FIG. 19B illustrates an embodiment of a corresponding trace showing the voltage response to a complex impedance stimulating biological tissue.
Figure 19B:
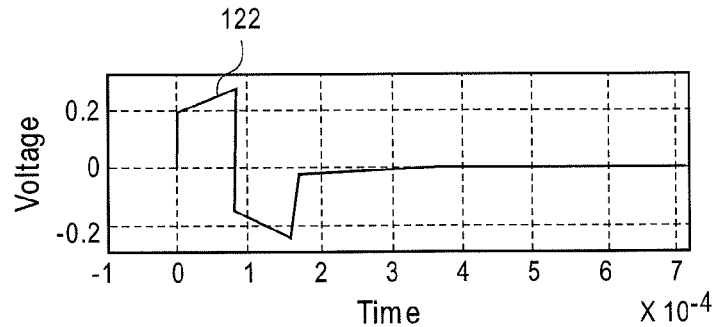

To determine the differences in energy requirement between the stimulation system 100 of the present invention and conventional spinal cord stimulation systems, the respective stimulation signals can be compared. In one embodiment, the stimulation signal of the present invention has a rectangular waveform, such as illustrated by a trace 120 shown in FIG. 19A, wherein the pulse width is approximately 80 µs and the current amplitude is approximately 200 µA. The integral of this curve (i.e. the area under this curve) is the total charge, corresponding to the energy and related to tissue impedance. In this example, the charge delivered is (200 µA)×(80 µs)=16 nC per pulse. FIG. 19B illustrates an embodiment of a trace 122 showing the voltage response to a complex impedance stimulating biological tissue. Thus, the total energy used is 7 nJ, wherein the Warburg resistance is 650$\Omega$, the Warburg capacitance is 0.2 µF and the tissue resistance is 1000 $\Omega$.

Figure 20A:
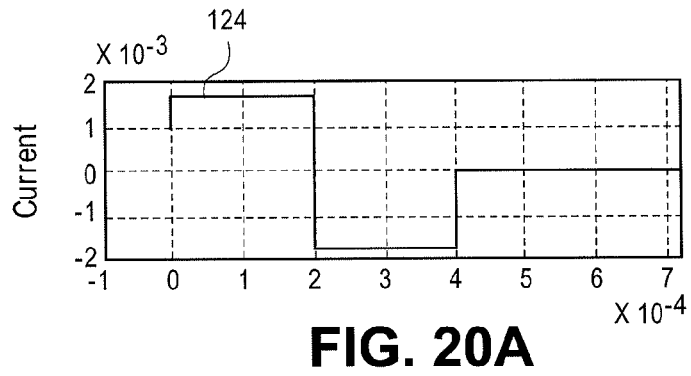
FIG. 20A illustrates an embodiment of a trace representing an example stimulation signal of a conventional spinal cord stimulator and FIG. 20B illustrates an embodiment of a corresponding trace showing the voltage response to a complex impedance stimulating biological tissue.
Figure 20B:
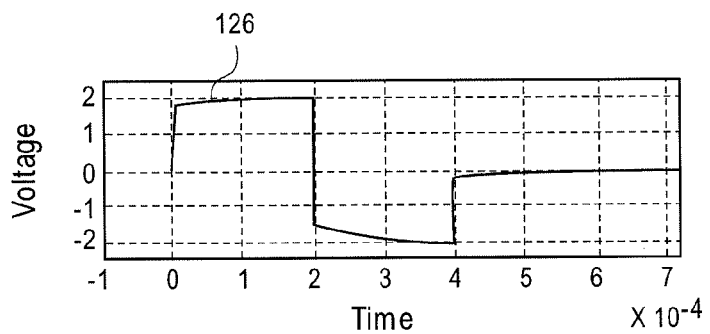

FIG. 20A illustrates a trace 124 representing an example stimulation signal of a conventional spinal cord stimulator. Here the pulse width is approximately 200 µs and the current amplitude is approximately 1.7 mA (or 1700 µA) which is around an order of magnitude greater than the current amplitude of the stimulation system 100 of the present invention. Thus, the charge delivered is (200 µs)×(1.7 mA)=340 nC. FIG. 20B illustrates an embodiment of a trace 126 representing the voltage response to a complex impedance stimulating biological tissue. Thus, the total energy used is 1294 nJ, wherein the Warburg resistance is 200$\Omega$, the Warburg capacitance is 0.5 µF and the tissue resistance is 1000$\Omega$. In this example, the energy supplied by the stimulation system 100 of the present invention is 0.54% (7 nJ/1294 nJ) of the energy supplied by conventional stimulation systems. This significant reduction in energy is due to the lower energy requirements of selectively stimulating the target anatomy, particularly the DRG. Typically, the energy supplied by the stimulation system 100 of the present invention is less than 10% of conventional systems, particularly less than 5%, more particularly less than 1%.

Figure 21:
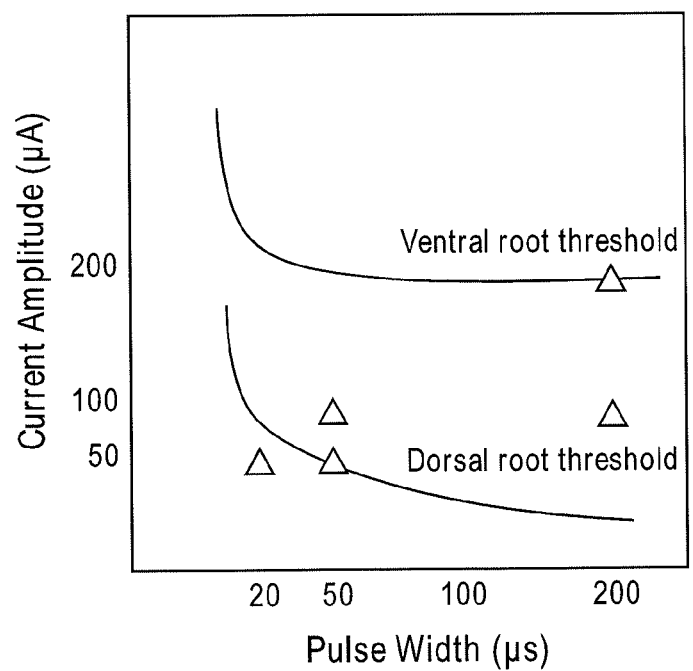
FIG. 21 illustrates data indicating the stimulation signal parameters which selectively targeted the DRG wherein there is an energy threshold in which the DRG is stimulated which is below the energy threshold in which the ventral root is stimulated.

It may be appreciated that the above example is for illustrative purposes. FIG. 21 illustrates additional data indicating the stimulation signal parameters which selectively targeted the DRG. As shown, there is an energy threshold in which the DRG is stimulated which is below the energy threshold in which the ventral root is stimulated. By providing stimulation signals below the ventral root threshold, the patient's pain sensations may be blocked without the negative side effects of ventral root stimulation.

Due to variability in patient anatomy, pain profiles, pain perception and lead placement, to name a few, signal parameter settings will likely vary from patient to patient and from lead to lead within the same patient. Signal parameters include voltage, current amplitude, pulse width and repetition rate, to name a few. In some embodiments of the stimulation system 100 of the present invention, the voltage provided is in the range of approximately 0-7 volts. In some embodiments, the current amplitude provided is less than approximately 4 mA, particularly in the range of approximately 0.5-2 mA, more particularly in the range of approximately 0.5-1.0 mA, 0.1-1.0 mA, or 0.01-1.0 mA. Further, in some embodiments, the pulse width provided is less than approximately 2000 µs, particularly less than approximately 1000 µs, more particularly less than approximately 500 µs, or more particularly 10-120 µs. And, in some embodiments, the repetition rate is in the range of approximately 2-120 Hz, up to 200 Hz or up to 1000 Hz.

Typically, stimulation parameters are adjusted until satisfactory clinical results are reached. Thus, there is an envelope of stimulation parameter value combinations between the threshold for DRG stimulation and ventral root stimulation for any given lead positioned in proximity to any given DRG per patient. The specific combinations or possible combinations that could be used to successfully treat the patient are typically determined perioperatively in vivo and postoperatively ex vivo and depend on a variety of factors. One factor is lead placement. The closer the desired electrodes are to the DRG the lower the energy required to stimulate the DRG. Other factors include electrode selection, the anatomy of the patient, the pain profiles that are being treated and the psychological perception of pain by the patient, to name a few. Over time, the parameter values for any given lead to treat the patient may change due to changes in lead placement, changes in impedance or other physical or psychological changes. In any case, the envelope of parameter values is exceedingly lower than those of conventional stimulation systems which require energy delivery of at least an order of magnitude higher to treat the patient's pain condition.

Given the lower ranges of parameter values for the system 100 of the present invention, the granularity of control is also smaller in comparison to conventional stimulation systems. For example, current in a conventional stimulation system is typically adjustable in increments of 0.1 mA. In some embodiments of the present invention, this increment is larger than the entire range of current amplitude values that may be used to treat the patient. Thus, smaller increments are needed to cycle through the signal parameter values to determine the appropriate combination of values to treat the condition. In some embodiments, the system 100 of the present invention provides control of current amplitude at a resolution of approximately 25 µA, particularly when using a current amplitude under, for example, 2 mA, however it may be appreciated that smaller increments may be used such as approximately 10 µA, 5 µA or 1 µA. In other embodiments, control of current amplitude is provided at a resolution of approximately 50 µA, particularly when using a current amplitude of, for example, 2 mA or greater. It may be appreciated that such a change in resolution may occur at other levels, such as 1 mA. Similarly, voltage in a conventional stimulation system is typically adjustable in increments of 100 mV. In contrast, some embodiments of the present invention provide control of voltage at a resolution of 50 mV. Likewise, some embodiments of the present invention provide control of pulse width at a resolution of 10 µs. Thus, it may be appreciated that the present invention provides a high granularity of control of stimulation parameters due to the low ranges of parameter values.

It may be appreciated that in some instances even lower levels of energy may be used to successfully treat a patient using the stimulation system 100 of the present invention. The closer a lead is positioned to a target DRG, the lower the level of energy that may be needed to selectively stimulate the target DRG. Thus, signal parameter values may be lower than those stated herein with correspondingly higher granularity of control.

Utilizing these signal parameter values, the stimulation profile is customized for the patient and programmed into the memory 108 of the IPG 102. As mentioned above, the IPG 102 is typically programmed through a computerized programming station or programming system. This programming system is typically a self-contained hardware/software system, or can be defined predominately by software running on a standard personal computer (PC). The PC or custom hardware can have a transmitting coil attachment or antenna to allow for the programming of implants, or other attachments to program external units. Patients are generally provided hand-held programmers (patient programmer 300) that are more limited in scope than are the physician-programming systems (clinical programmer 200), with such handheld programmers still providing the patient with some control over selected parameters. Thus, this allows for easy changes to the stimulation profile over time, as needed.

Figure 22:
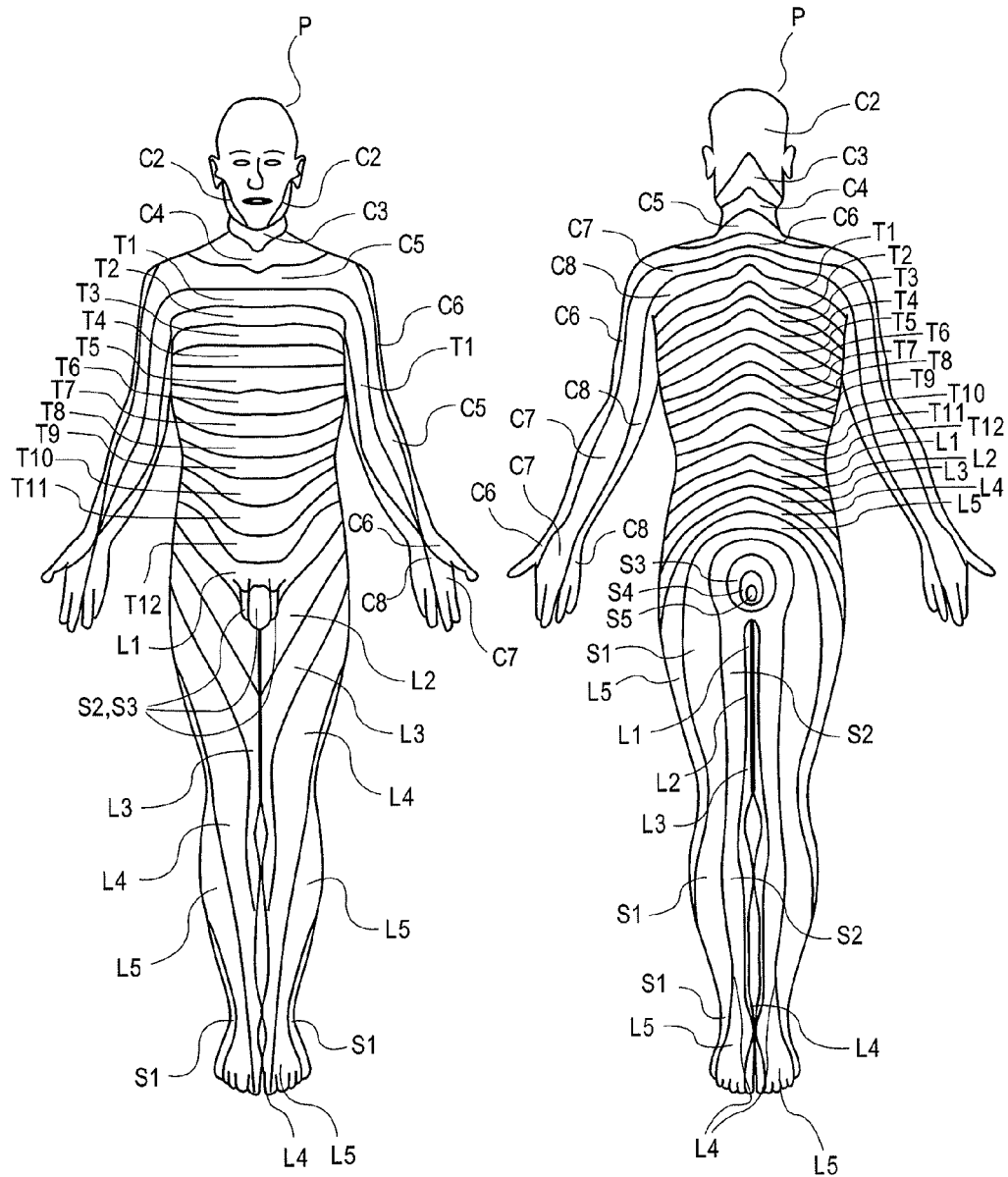
FIG. 22 illustrates the dermatomal arrangement or "map" of dermatomes along a patient.

As mentioned previously, effective treatment of a condition may be achieved by directly stimulating a target anatomy associated with the condition while minimizing or excluding undesired stimulation of other anatomies. When such a condition is limited to or primarily affects a single dermatome, the present invention allows for stimulation of a single dermatome or regions within a dermatome (also referred to as subdermatomal stimulation). A dermatome is considered the body region that is innervated by a single spinal level. FIG. 22 illustrates the dermatomal arrangement or "map" of dermatomes along a patient P. The dermatomes form into bands around the trunk but in the limbs their organization is more complex as a result of the dermatomes being "pulled out" as the limb buds form and develop into the limbs during embryological development. Each dermatome is labeled according to its associated spinal level. Upper bodily regions are innervated by nerves traveling in the cervical spinal segments and as the innervation pattern progresses caudally so do the spinal segments innervating the dermatome. Thus, regions in the middle of the body (thorax, etc) are innervated by thoracic spinal segments and lower bodily regions are innervated by lumbar and sacral spinal segments.

The nerves innervating a dermatome originate from DRGs on the associated spinal level Since each dermatome is supplied by a single pair of DRGs, stimulation of one or both of these DRGs will substantially effect a single dermatome. Referring back to FIG. 17, the present invention provides for stimulation of a single DRG or a pair of DRGs on a single spinal level independently of other DRGs or nerve tissues in the surrounding area. This allows for a single dermatome to be stimulated. It may be appreciated that there is overlap of innervation between adjacent dermatomes. However, stimulation of one or more DRGs on a spinal level will largely affect the directly associated dermatome with significantly lesser affects in adjacent dermatomes. Likewise, stimulation of a single DRG on, for example, the right side of the spinal column will largely affect the right side of the body within the directly associated dermatome. Thus, stimulation of a single DRG may stimulate a portion of a single dermatome. This is not the case with conventional spinal stimulation systems which simultaneously stimulate multiple dermatomes. By design, such conventional systems cannot isolate a single dermatome or a portion of a dermatome for treatment and such stimulation will substantially affect more than one dermatome.

Figure 23:
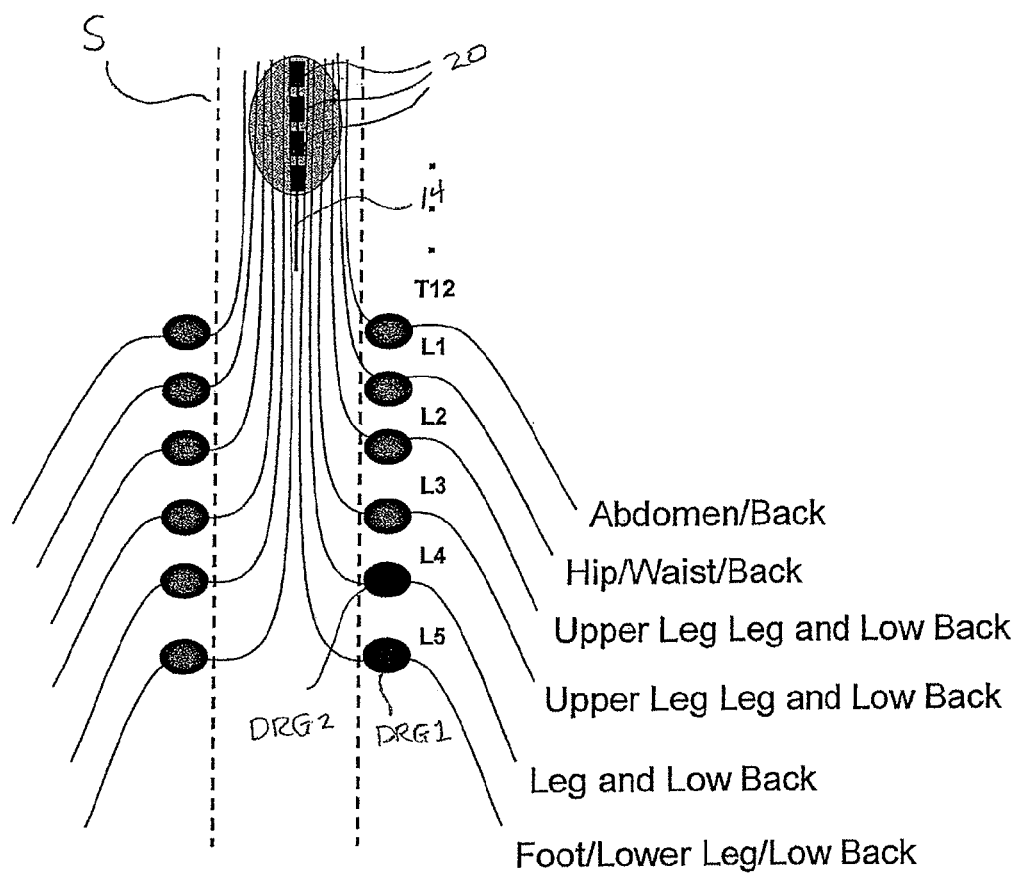
FIG. 23 schematically illustrates DRGs on various spinal levels with associated body regions that may be affected by selective stimulation of the individual DRGs.
Figure 24B:
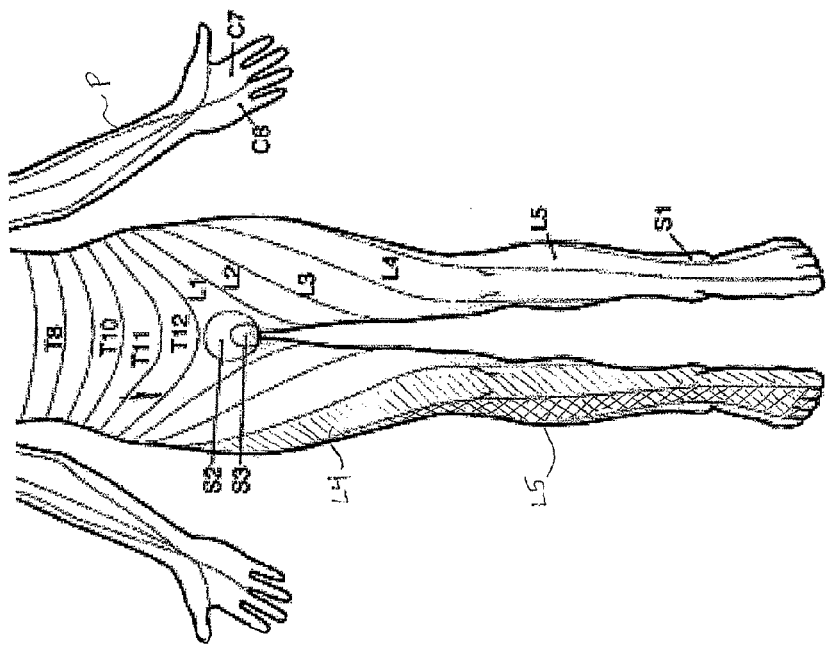
FIG. 24B illustrates the patient from the front, including the dermatomes of the lower body.
Figure 24A:
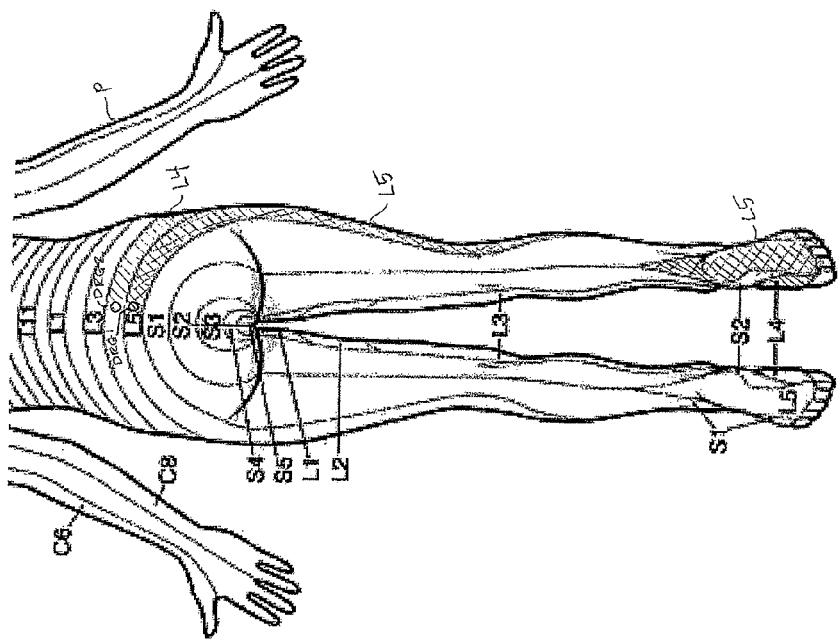
FIG. 24A illustrates the patient from the back, including the dermatomes of the lower body and a schematic representation of the general area of the DRGs.

FIG. 23 schematically illustrates DRGs on various spinal levels with associated body regions that may be affected by selective stimulation of the individual DRGs. For example, stimulation of DRG1 on the right side of L5 may affect the foot, lower leg and/or low back on the right side of the patient. Likewise, stimulation of DRG2 on the right side of L4 may affect the leg and/or low back on the right side of the patient. FIGS. 24A-24B illustrate these body regions along the dermatomes of the patient P. FIG. 24A illustrates the patient P from the back, including the dermatomes of the lower body and a schematic representation of the general area of the DRGs. The region of the L5 dermatome that is likely affected by stimulation of DRG1 is indicated by double-hatched lines. Likewise, FIG. 24B illustrates the patient P from the front, including the dermatomes of the lower body. Again, the region of the L5 dermatome that is likely affected by stimulation of DRG1 is indicated by double-hatched lines. This portion of the dermatome extends along the bottom of the right foot, the top of the right foot, along the lower leg and up to the low back. Similarly, the region of the L4 dermatome that is likely affected by stimulation of DRG2 is indicated by hatched lines in both FIG. 24A and FIG. 24B. This portion of the dermatome mainly extends along the front of the lower leg and up to the low back. Thus, for patients having pain or another condition in these body regions, DRG1 and DRG2 may be stimulated so as to treat such conditions while minimally or not affecting other body regions.

Figure 2:
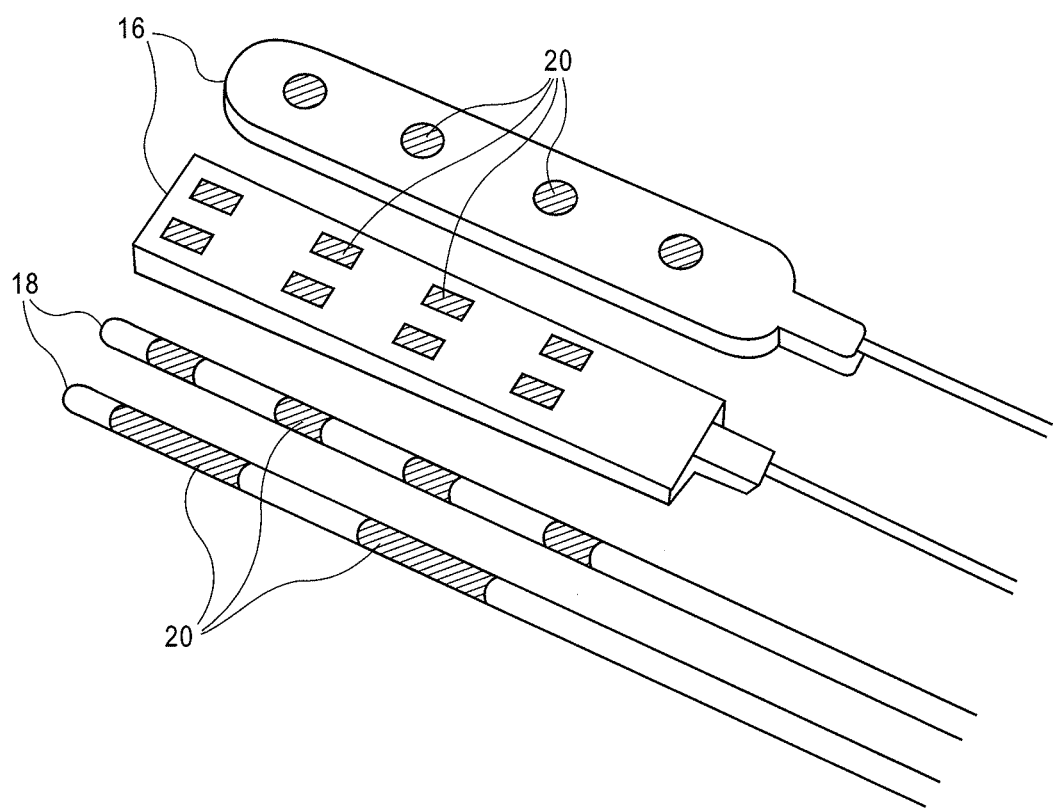
Figure 3:
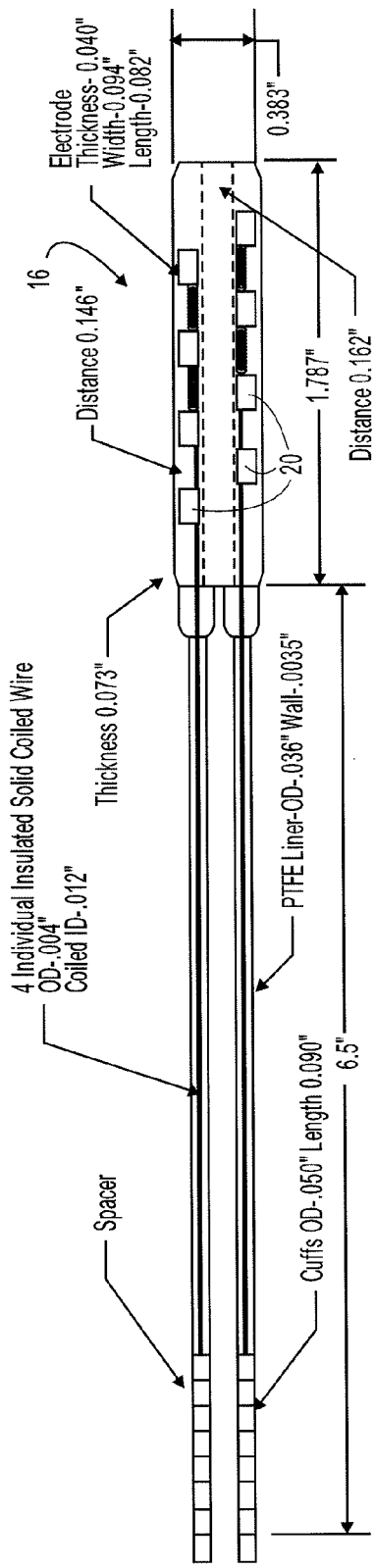
Figure 4:
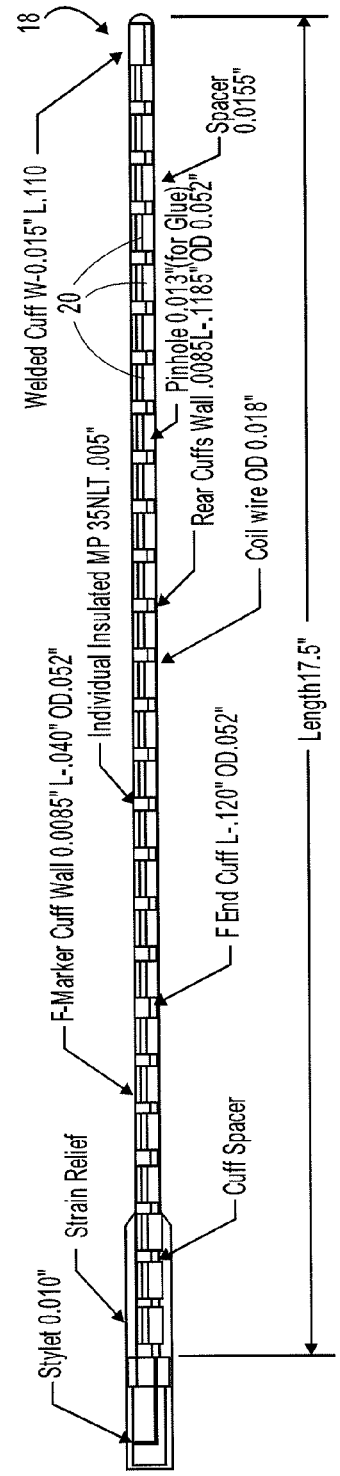
Figure 5:
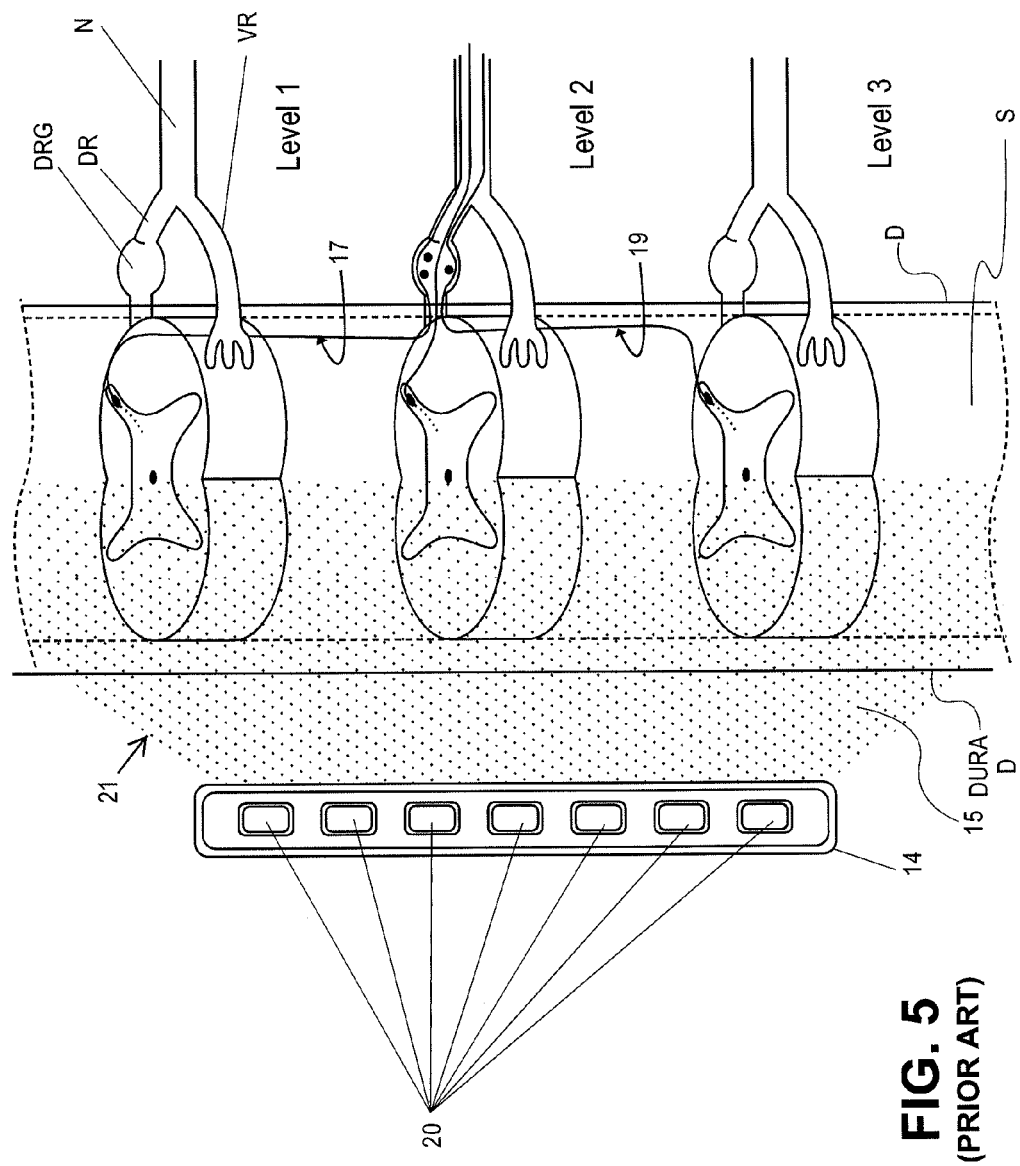
Figure 6:
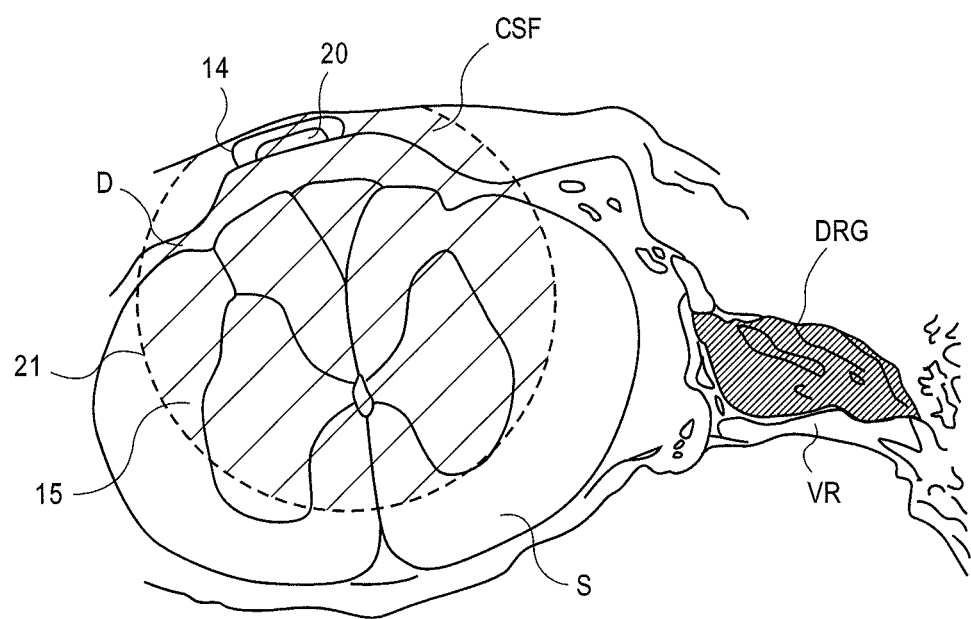

Referring back to FIG. 23, traditional placement of a conventional spinal stimulation system (such as illustrated in FIG. 5) is also illustrated wherein the lead 14 is positioned along the midline of the spinal column S so that the electrodes 20 are aligned with the saggittal and parasaggittal midline. Such placement causes the electrodes 20 to stimulate many neural fibers innervating body regions unassociated and unaffected by the condition for which treatment is desired. In this example, stimulation by the electrodes 20 would affect the T12, L1, L2, L3, L4, L5 dermatomes on both sides of the patient's body.

Figure 25:
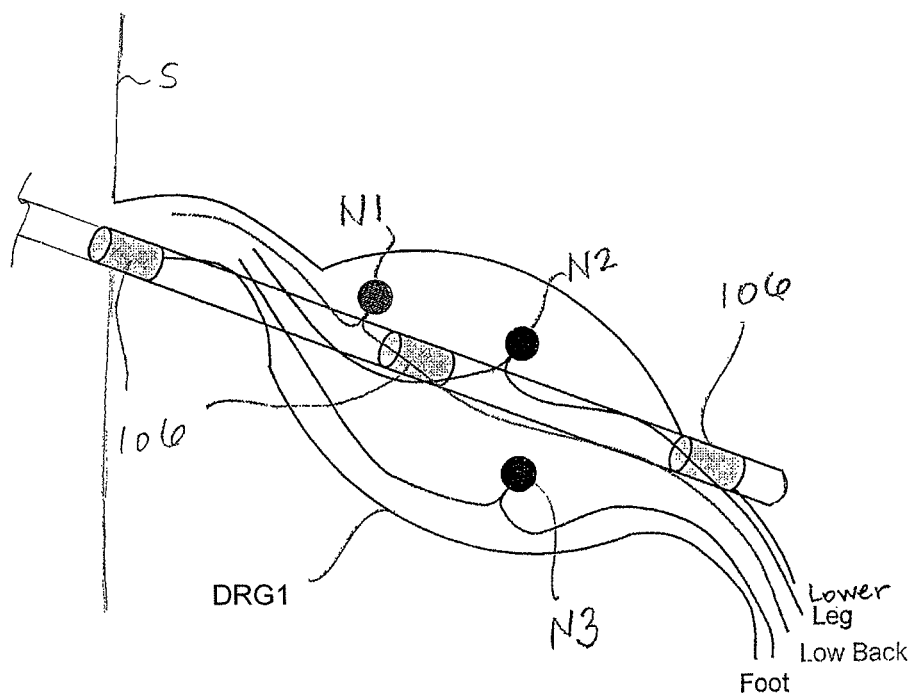
FIG. 25 schematically illustrates selective stimulation of a DRG according to aspects of the present invention.

FIG. 25 schematically illustrates selective stimulation of DRG1 according to aspects of the present invention. As shown, a lead 104 is positioned so that at least one of the at least one electrode 106 is positioned on, near or about the target DRG (DRG1). Different body regions associated with DRG1 (foot, lower leg, low back) may be traced to specific sensory neurons within the DRG1. In particular, each sensory neuron includes a cell body or soma which may be targeted to stimulate the sensory neuron independently of other surrounding neurons. In this example, the lower leg is associated with soma N1, the low back is associated with soma N2, and the foot is associated with soma N3. It has been suggested by a variety of scientific studies that there is a specific somatotopic orientation of neurons (and associated somas) within the DRG subserving sensory function to distinct anatomy.

A somatotopic map is an anatomically specific orientation of sensory integration. It is well-known that once sensory information has traveled into the central nervous system, a "somatotopic" map is organized in the cortex of the brain. Thus, specific regions of the somatosensory cortex are involved in sensory processing from specific anatomical regions. Thus, stimulation of various regions of specific subregions of the somatosensory cortex will result in the perception of sensory input from specific anatomical regions. In addition, research has suggested that not only are there somatotopic maps within the central nervous system, but also in spinal neural structures such as the dorsal root ganglion. Typically, such mapping has been completed in animal studies by injecting tracer chemicals in peripheral anatomical structures and then looking at labeled cells in the DRG to see the relative distribution of those labeled cells. The dorsal root ganglion is a special neural structure that contains the cell bodies (soma) of the neurons that are innervating specific dermatomes. The understanding of a somatotopic map for the dorsal root ganglion may allow for the targeting of portions of the DRG to provide therapy to one or more specific regions within the dermatome associated with that DRG. Thus, sub-dermatomal targeting may allow very specific therapeutic application in the treatment of pain and other conditions.

Referring again to FIG. 25, portions of the DRG may be selectively stimulated to affect specific regions within a dermatome. In this embodiment, soma N1, soma N2, or soma N3 may be stimulated to cause different treatment effects. Likewise, two or more of the somas N1, N2, N3 may be stimulated in combination to cause further treatment effects. Each soma may be selectively stimulated by manipulation of one or more of the following features: position of the electrode(s) 106 in relation to the DRG, selection of the electrode combinations for stimulation, and programming of the stimulation signal parameters, such as pulse width, amplitude, and frequency. By such manipulation, a desired electrical field is generated and positioned relative to the DRG to stimulate a particular portion of the DRG in three-dimensional space. This particular portion typically includes the one or more somas which are targeted to influence the desired treatment effect.

Figure 26A:
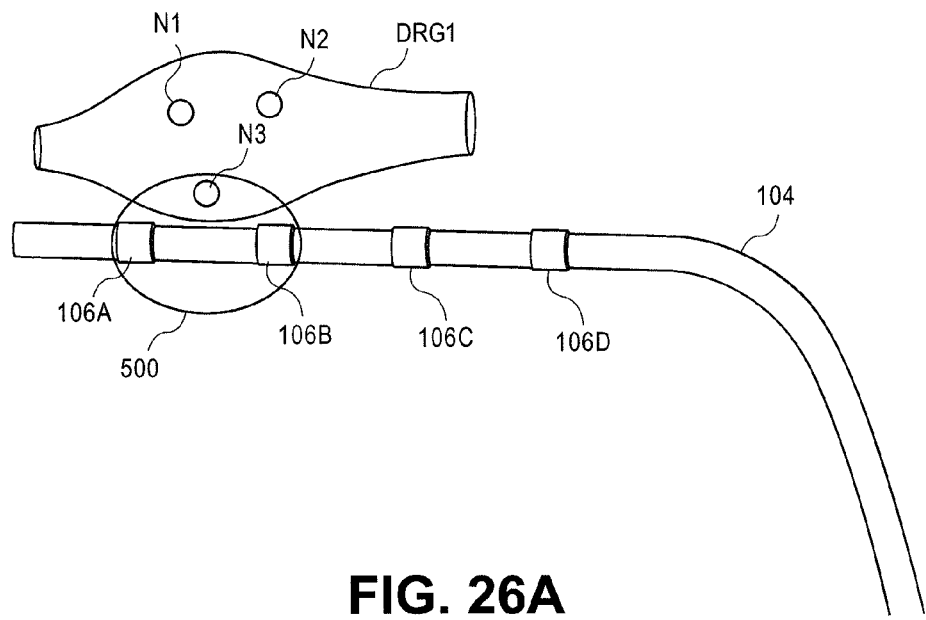
FIGS. 26A, 26B, 26C, 26D illustrate perspective views of a lead stimulating a portion of a DRG to affect a specific region within a dermatome.
Figure 26B:
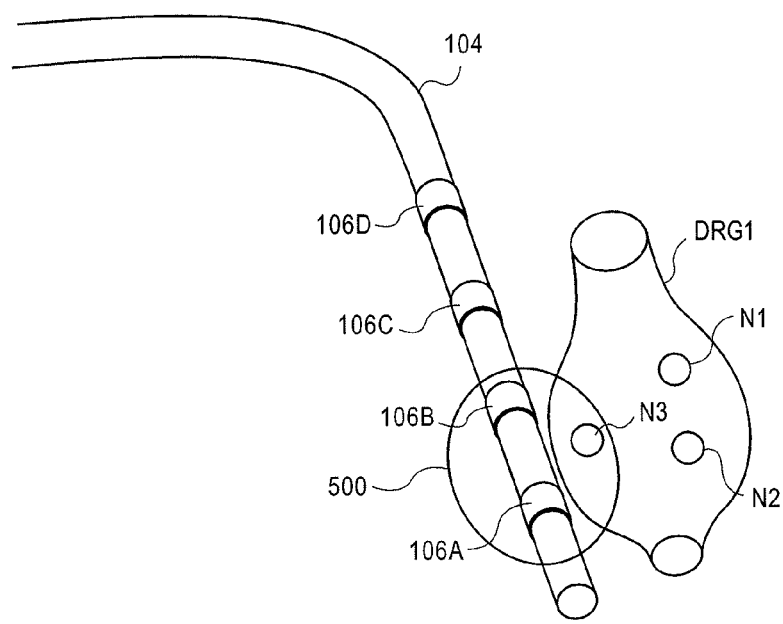
Figure 26C:
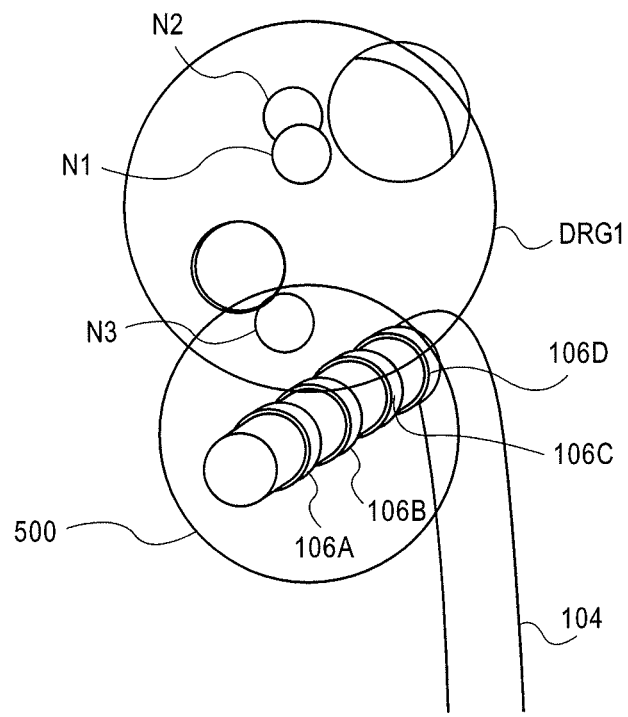
Figure 26D:
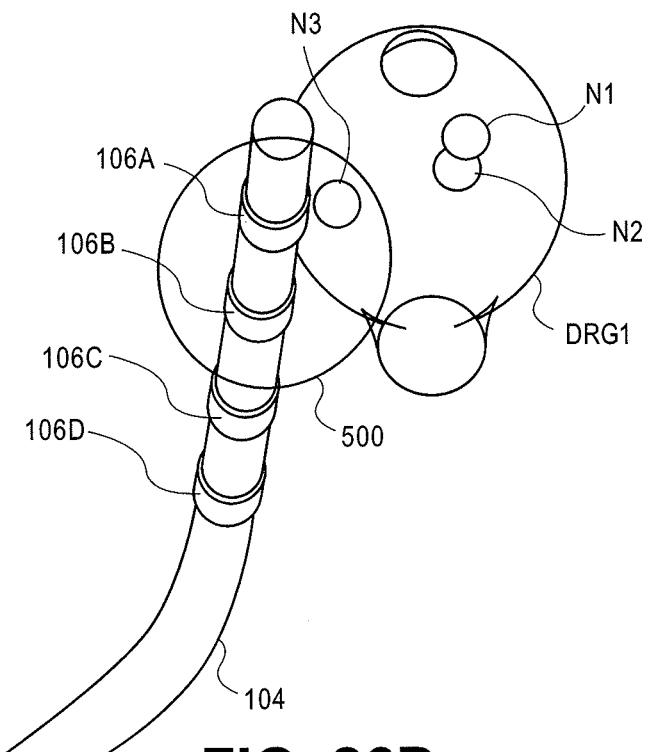

FIGS. 26A-26D illustrate perspective views of a lead 104 stimulating a portion of DRG1 to affect a specific region within a dermatome. Referring to FIG. 26A, DRG1 is shown to include soma N1, soma N2, and soma N3. The lead 104 is positioned on, near or about the DRG1 according to the methods of the present invention. In this example, two electrodes 106a, 106b are selected for stimulation while the remaining two electrodes 106c, 106d are neutral. An electric field 500 is generated by the two electrodes 106a, 106b according to chosen stimulation signal parameters so as to stimulate soma N3 while providing minimal or no stimulation to soma N1 and soma N2. In this embodiment, soma N3 is associated with the body region of the foot whereas soma N1 is associated with the low back and soma N2 is associated with the lower leg. Thus, the patient will have a targeted treatment effect in the foot without a treatment effect in the low back and lower leg within the same dermatome. FIG. 26B rotates the view of FIG. 26A to illustrate the three-dimensional electric field 500 and its inclusion of soma N3 along with exclusion of soma N1 and soma N2. Likewise, FIG. 26C rotates the view of FIG. 26A to provide a perspective end view, wherein again the three-dimensional electric field 500 is shown to include soma N3 while excluding soma N1 and soma N2. And further, FIG. 25D rotates the view of FIG. 25A to provide a perspective bottom view of the lead 104 in proximity to the DRG1 so that the electric field 500 stimulates soma N3 while excluding soma N1 and soma N2.

Different somas may be selectively stimulated by physically moving the lead 104 in relation to the DRG1. For example, by moving the lead 104 along the surface of the DRG1, the electric field 500 can be moved to select different somas, such as soma N1 while excluding somas N2, N3. Or, the lead 104 can remain stationary in relation to the DRG1, and different electrodes 106 may be utilized for stimulation to move the electric field 500. Likewise, the shape of the electric field 500 can be changed by changing the electrode combination and/or changing the stimulation signal parameters. For example, the electric field 500 may be increased in size by changing stimulation signal parameters, such as increasing the amplitude. Or, the size of the electric field 500 may be increased by changing the electrode combination, such as by utilizing an additional electrode for stimulation. In this example, the size of the electric field 500 may be increased to include both soma N3 and soma N1, while substantially excluding soma N2. This would cause the patient to have a targeted treatment effect in the foot and low back without a treatment effect in the lower leg within the same dermatome. Similarly, the size of the electric field 500 may be increased to include somas N1, N2, N3. This would cause the patient to have a targeted treatment effect in the foot, low back and lower leg within the same dermatome.

FIGS. 27-28 provide clinical data which illustrate the correlation between changes in electrode combination and/or signal parameters and the resultant changes in affected body region. The clinical data was gathered during a clinical trial in which the patient subjects were implanted with one or more leads 104 in accordance with the present invention. Each lead 104 was positioned so that at least one of its one or more electrodes 106 was on, near or about a DRG, such as illustrated in FIGS. 17-18.

FIG. 27 provides a table of clinical data from Patient No. 1, wherein one lead (Lead No. 2) was implanted so as to stimulate a DRG on level L5. As shown in Row 1 of the table, each electrode or contact along the lead is labeled by number (1, 2, 3, 4) wherein there were four electrodes present. Contact 1 and Contact 2 were configured as Off or Neutral (N). And, Contact 3 was configured as an anode (+) while Contact 4 was configured as a cathode (−). The signal parameters were set as follows: amplitude=800 μA, pulse width=60 μs, frequency=70 Hz. It may be appreciated that this clinical data was gathered in an effort to map body regions affected by stimulation of portions of the associated DRG. Therefore, the parameter settings were not necessarily within the desired ranges for treatment. At these signal parameter settings, the bottom of the patient's foot was affected by the stimulation. As shown in Row 2 of the table, the amplitude was raised to 1.8 mA while all other variables remained the same. Consequently, both the patient's foot and calf were affected by the stimulation. Thus, the electric field provided by Contact 3 and Contact 4 was enlarged causing additional sensory neurons to be stimulated. Further, Row 3 of the table shows that when the amplitude was raised to 2.25 mA, the affected body region was expanded to include the back of the knee. Likewise, Row 4 of the table shows that when the amplitude was raised to 2.75 mA, the affected body region was expanded to include the hip and Row 5 of the table shows that when the amplitude was raised to 3.0 mA, the affected body region was expanded to include the buttock. Thus, as the electric field provided by Contact 3 and Contact 4 changed shape, additional sensory neurons were stimulated causing additional body regions of the dermatome to be affected. This illustrates that subdermatomal stimulation may be achieved by manipulating the electric field and signal parameters.

FIG. 28 provides a table of clinical data from a different patient, Patient No. 2, wherein one lead (Lead No. 1) was implanted so as to stimulate a DRG on level L4. As shown in Row 1 of the table, each electrode or contact along the lead is labeled by number (1, 2, 3, 4) wherein there were four electrodes present. Contact 1 and Contact 2 were configured as Off or Neutral (N). And, Contact 3 was configured as an anode (+) while Contact 4 was configured as a cathode (−). The signal parameters were set as follows: amplitude=325 μA, pulse width=120 μs, frequency=60 Hz. Again, it may be appreciated that this clinical data was gathered in an effort to map body regions affected by stimulation of portions of the associated DRG. Therefore, the parameter settings were not necessarily within the desired ranges for treatment. At these signal parameter settings, the patient's calf was affected by the stimulation. As shown in Row 2 of the table, the amplitude was raised to 350 µA while all other variables remained the same. Consequently, both the patient's calf and knee were affected by the stimulation. Thus, the electric field provided by Contact 3 and Contact 4 was enlarged causing additional sensory neurons to be stimulated. Further, Row 3 of the table shows that when the amplitude was raised to 425 µA, the affected body region was expanded to include the hip. Thus, as the electric field provided by Contact 3 and Contact 4 was enlarged, additional sensory neurons were stimulated causing additional body regions of the dermatome to be affected.

Row 4 of the table of FIG. 28 shows a change in the electrode configuration. Here, Contact 1 remained Off or Neutral (N) while Contact 2 was configured as a cathode (−), Contact 3 was configured as an anode (+) and Contact 4 was configured as a cathode (−). The signal parameters were set as follows: amplitude=275 µA, pulse width=120 µs, frequency=60 Hz. Consequently, at these signal parameter settings, the patient's calf to ankle was affected by the stimulation. Thus, in comparison to Row 1, although the amplitude was lowered, the altered shape of the electric field provided by the new electrode configuration allowed for additional sensory neurons to be stimulated.

A comparison of Row 5 and Row 6 illustrate the effect of changing electrode configuration while other variables remain the same. As shown in Row 5 of the table, Contact 1 was Off or Neutral (N) while Contact 2 was configured as a cathode (−), Contact 3 was configured as an anode (+) and Contact 4 was configured as a cathode (−). The signal parameters were set as follows: amplitude=625 µA, pulse width=120 µs, frequency=60 Hz. At these signal parameter settings, affected body regions were above the knee and to the side of the thigh. While keeping the same signal parameter settings, the electrode configuration was changed so that Contact 1 was Off or Neutral (N) while Contact 2 was configured as an anode (+), Contact 3 was configured as an cathode (−) and Contact 4 was configured as an anode (+), as shown in Row 6 of the table. This change in the electric field caused the affected body region to change to the front of the calf. Raising the amplitude, as shown in Row 7, increased the affected body region to include the knee. Row 8 shows a change in both amplitude and pulse width, which creates a different affect within the dermatome. And, again, raising the amplitude, as shown in Row 9, increases the affected body region. This further illustrates that subdermatomal stimulation may be achieved by manipulating the electric field and signal parameters to affect particular body regions while leaving other body regions substantially unaffected.

It may be appreciated that in some embodiments subdermatomal stimulation is achieved by factors other than or in addition to somatotopic mapping of the DRG. In these embodiments, body regions that are considered as focal areas of the condition for which the patient is being treated were preferentially affected by the stimulation. For example, when the condition being treated is pain, body regions that the patient considered to be painful are preferentially affected by the stimulation. This suggests that DRG stimulation therapy preferentially neuromodulates neural elements that are involved in the pain condition specific to the area of pain. This corroborates with basic neurophysiologic data that suggest both small diameter soma and large diameter neurons residing in the DRG involved in the neural transduction of pain and other somatosensory signals undergo physiologic changes that affect the biophysics of the cell membrane. This suggests that neurons become hyperexcitable possibly through the altered function of transmembrane integral membrane proteins—in particular ion channels. This altered biophysical function of the cells involved in the processing of pain information would provide a basis for enhanced ability to neuromodulate the cell function with electrical fields. This, in turn, would underlie the ability to preferentially generate pain relief and paresthesias in the selected anatomically painful regions.

A variety of pain-related conditions are treatable with the systems, methods and devices of the present invention. In particular, the following conditions may be treated:
1) Failed Back Surgery syndrome
2) Chronic Intractable Low Back Pain due to:
   A) Unknown Etiology
   B) Lumbar facet disease as evidenced by diagnostic block(s)
   C) Sacroiliac Joint disease as evidenced by diagnostic block(s)
   D) Spinal Stenosis
   E) Nerve root impingement—non-surgical candidates
   F) Discogenic Pain—discography based or not
4) Complex Regional Pain Syndrome
5) Post-Herpetic Neuralgia
6) Diabetic Neuropathic Pain
7) Intractable Painful Peripheral Vascular Disease
8) Raynaud's Phenomenon
9) Phantom Limb Pain
10) Generalized Differentiation Pain Conditions
11) Chronic, Intractable Angina
12) Cervicogenic Headache
13) Various Visceral Pains (pancreatitis, etc.)
14) Post-Mastectomy Pain
15) Vuvlodynia
16) Orchodynia
17) Painful Autoimmune Disorders
18) Post-Stroke Pain with limited painful distribution
19) Repeated, localized sickle cell crisis
20) Lumbar Radiculopathy
21) Thoracic Radiculopathy
22) Cervical Radiculopathy
23) Cervical axial neck pain, "whiplash"
24) Multiple Sclerosis with limited pain distribution Each of the above listed conditions is typically associated with one or more DRGs wherein stimulation of the associated DRGs provides treatment or management of the condition.

Likewise, the following non-painful indications or conditions are also treatable with the systems, methods and devices of the present invention:
1) Parkinson's Disease
2) Multiple Sclerosis
3) Demylenating Movement Disorders
4) Physical and Occupational Therapy Assisted Neurostimulation
5) Spinal Cord Injury—Neuroregeneration Assisted Therapy
6) Asthma
7) Chronic Heart Failure
8) Obesity
9) Stroke—such as Acute Ischemia Again, each of the above listed conditions is typically associated with one or more DRGs wherein stimulation of the associated DRGs provides treatment or therapy. In some instances, Neuroregeneration Assisted Therapy for spinal cord injury also involves stimulation of the spinal column.

It may be appreciated that the systems, devices and methods of the present invention may alternatively or additionally be used to stimulate ganglia or nerve tissue. In such instances, the condition to be treated is associated with the ganglia or nerve tissue so that such stimulation provides effective therapy. The following is a list of conditions or indications with its associated ganglia or nerve tissue:
1) Trigeminal Neuralgia (Trigeminal Ganglion)
2) Hypertension (Carotid Sinus Nerve/Glossopharangyl Nerve)
3) Facial Pain (Gasserian Ganglion)
4) Arm Pain (Stellate Ganglion)
5) Sympathetic Associated Functions (Sympathetic Chain Ganglion)
6) Headache (Pterygoplatine Ganglion/Sphenopalatine Ganglion)

It may also be appreciated that the systems and devices of the present invention may also be used to stimulate various other nerve tissue including nerve tissue of the peripheral nervous system, somatic nervous system, autonomic nervous system, sympathetic nervous system, and parasympathetic nervous system, to name a few. Various features of the present invention may be particularly suited for stimulation of portions of these nervous systems. It may further be appreciated that the systems and devices of the present invention may be used to stimulate other tissues, such as organs, skin, muscle, etc.

It may be appreciated that although the lead is described herein as positionable so that the at least one electrode is on, near or about a target anatomy, at least one of the at least one electrode may optionally be positioned in the target anatomy.

Although the foregoing invention has been described in some detail by way of illustration and example, for purposes of clarity of understanding, it will be obvious that various alternatives, modifications, and equivalents may be used and the above description should not be taken as limiting in scope of the invention which is defined by the appended claims.

What is claimed is:

1. A method of treating a condition of a patient, wherein the condition is associated with a portion of a dorsal root ganglion and is not substantially associated with other portions of the dorsal root ganglion, the method comprising:
   positioning a lead having at least one electrode so that at least one of the at least one electrode resides in proximity to the portion of a dorsal root ganglion; and
   providing a stimulating signal to the at least one of the at least one electrode so as to stimulate the portion of the dorsal root ganglion in a manner that affects the condition while not substantially stimulating the other portions, wherein an amplitude of the stimulation signal is incrementally adjusted below and above a specified level of amplitude in response to user inputs accepted by an external programmer;
   wherein the external programmer is configured such that, when said amplitude of the stimulation signal is at least the specified level, said amplitude is adjusted in the first increments of 50 µA or less in response to user inputs accepted by the external programmer, and when said amplitude is less than the specified level, said amplitude is adjusted in second increments of 25 µA or less in response to user inputs accepted by the external programmer;
   wherein the second increments are less than the first increments;
   wherein the first and second increments enable adjustments to the amplitude in small enough increments to identify a magnitude for the amplitude that stimulates the target dorsal root ganglion, to achieve the targeted treatment, without stimulating a ventral root associated with the target dorsal root ganglion.

2. A method as in claim 1, wherein the condition comprises pain.

3. A method as in claim 1, wherein affecting the condition comprises alleviating the pain without causing a perceptible motor response.

4. A method as in claim 1, wherein the condition is sensed by a patient at a location within a dermatome, and wherein the other portions of the dorsal root ganglion are associated with other locations within the dermatome.

5. A method as in claim 1, wherein positioning the lead comprises advancing the lead using an epidural approach.

6. A method as in claim 1, further comprising:
   storing a therapeutic amplitude value in a pulse generator implanted in the patient wherein the therapeutic amplitude value is determined during the providing.

7. A method as in claim 1, further comprising:
   mapping activated body regions for sensory responses for a plurality of amplitudes employed during the providing.

8. A method as in claim 7, further comprising:
   switching active electrodes applying the stimulation signal to the patient during the mapping.

9. A method as in claim 7, further comprising:
   stimulating multiple dorsal root ganglion during the mapping.

* * * * *